US008609669B2

(12) United States Patent
Xu et al.

(10) Patent No.: US 8,609,669 B2
(45) Date of Patent: Dec. 17, 2013

(54) POTASSIUM CHANNEL MODULATORS

(75) Inventors: Xiangdong Xu, Buffalo Grove, IL (US); Jennifer Van Camp, Lake Forest, IL (US); Marc J. Scanio, Lindenhurst, IL (US); William H. Bunnelle, Mundelein, IL (US); Lei Shi, Gurnee, IL (US); Augustine T. Osuma, Lindenhurst, IL (US); David DeGoey, Salem, WI (US); Arturo Perez-Medrano, Grayslake, IL (US); Sridhar Peddi, Schaumburg, IL (US); Jyoti R. Patel, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 50 days.

(21) Appl. No.: 13/287,635

(22) Filed: Nov. 2, 2011

(65) Prior Publication Data

US 2012/0122888 A1    May 17, 2012

Related U.S. Application Data

(60) Provisional application No. 61/414,275, filed on Nov. 16, 2010.

(51) Int. Cl.
*A01N 43/90* (2006.01)
*A61K 31/519* (2006.01)
*C07D 487/00* (2006.01)

(52) U.S. Cl.
USPC ........................................ 514/259.3; 544/281

(58) Field of Classification Search
None
See application file for complete search history.

(56) References Cited

U.S. PATENT DOCUMENTS

| | | | |
|---|---|---|---|
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2012/0190665 | A1* | 7/2012 | Gibbons et al. .......... 514/210.18 |

FOREIGN PATENT DOCUMENTS

| | | |
|---|---|---|
| WO | WO9507271 A1 | 3/1995 |
| WO | WO9710223 A1 | 3/1997 |
| WO | WO0140231 A1 | 6/2001 |
| WO | WO2004060893 A1 | 7/2004 |
| WO | WO2005090333 A1 | 9/2005 |
| WO | WO2005099353 A2 | 10/2005 |
| WO | WO2006008754 A1 | 1/2006 |
| WO | WO2007027454 A1 | 3/2007 |
| WO | WO2010112486 A1 | 10/2010 |
| WO | WO2011003065 A2 | 1/2011 |

OTHER PUBLICATIONS

Coenen V.M., et al., "Syntheses with Trichloracetonitril," Journal for Practical Chemistry, 1965, vol. 27 (5-6), pp. 239-250 (English abstract).
Bennett G.J., et al., "A Peripheral Mononeuropathy in Rat that Produces Disorders of Pain Sensation like those Seen in Man," Pain, 1988, vol. 33 (1), pp. 87-107.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blackburn-Munro G., et al., "Retigabine: Chemical Synthesis to Clinical Application," CNS Drug Reviews, 2005, vol. 11 (1), pp. 1-20.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Chaplan S.R., et al., "Quantitative Assessment of Tactile Allodynia in the Rat Paw," Journal of Neuroscience Methods , 1994, vol. 53, pp. 55-63.
Chiche L., et al., "Opening of Dichlorocyclopropanes in the Presence of Nucleophilic Internal. Intramolecular Absence of Participation. Rearrangement Concerted out of Allyl Chlorides," Canadian Journal of Chemistry, 1981, vol. 59 (1), pp. 164-174.
Coenen V.M., et al., "Syntheses with Trichloracetonitril," Journal for Practical Chemistry, 1965, vol. 27 (5-6), pp. 239-250.

(Continued)

*Primary Examiner* — Jeffrey Murray

(57) ABSTRACT

Disclosed herein are KCNQ potassium channels modulators of formula (I)

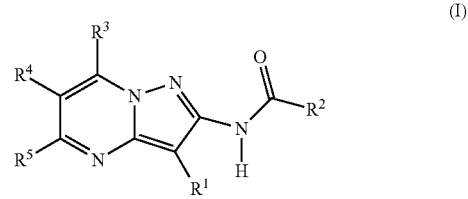

wherein $R^1$, $R^2$, $R^3$, $R^4$, and $R^5$ are as defined in the specification. Compositions comprising such compounds; and methods for treating conditions and disorders using such compounds and compositions are also described.

40 Claims, No Drawings

(56) References Cited

OTHER PUBLICATIONS

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Dalby-Brown W., et al., "K(V)7 Channels: Function, Pharmacology and Channel Modulators," Current Topics in Medicinal Chemistry, 2006, vol. 6 (10), pp. 999-1023.
Dixon W.J., "Efficient Analysis of Experimental Observations," Annual Review of Pharmacology and Toxicology, 1980, vol. 20, pp. 441-462.
Foster, A. B. et al., "Deuterium Isotope Effects in the Metabolism of Drugs and Xenobiotics: Implications for Drug Design," Advances in Drug Research, 1985, vol. 14, pp. 2-36.
Hansen H.H., et al., "Kv7 Channels: Interaction with Dopaminergic and Serotonergic Neurotransmission in the CNS," The Journal of Physiology, 2008, vol. 586 (7), pp. 1823-1832.
Hansen H.H., et al., "The KCNQ Channel Opener Retigabine Inhibits the Activity of Mesencephalic Dopaminergic Systems of the Rat," The Journal of Pharmacology and Experimental Therapeutics, 2006, vol. 318 (3), pp. 1006-1019.
Jentsch T.J., "Neuronal KCNQ Potassium Channels: Physiology and Role in Disease," Nature Reviews Neuroscience, 2000, vol. 1 (1), pp. 21-30.
Joshi S. K., et al., "Comparison of Antinociceptive Actions of Standard Analgesics in Attenuating Capsaicin and Nerve-Injury-Induced Mechanical Hypersensitivty ," Neuroscience, 2006, vol. 143, pp. 587-596.
Kato, S. et al., "Synthesis of Deuterated Mosapride Citrate," Journal of Labelled Compounds and Radiopharmaceuticals, 1995, vol. 36 (10), pp. 927-932.
Kim S.H., et al., "An Experimental Model for Peripheral Neuropathy Produced by Segmental Spinal Nerve Ligation in the Rat," Pain, 1992, vol. 50 (3), pp. 355-363.
Kushner, et al., "Pharmacological uses and perspectives of heavy water and deuterated compounds," Canadian Journal of Physiology and Pharmacology, 1999, vol. 77 (2), pp. 79-88.
Lizondo, J. et al., "Linezolid: Oxazolidinone antibacterial," Drugs of the Future, 1996, vol. 21 (11), pp. 1116-1123.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Miceli F., et al., "Molecular Pharmacology and Therapeutic Potential of Neuronal Kv7-Modulating Drugs," Current Opinion in Pharmacology , 2008, vol. 8 (1), pp. 65-74.
Munro G., et al. , "Kv7 (KCNQ) Channel Modulators and Neuropathic Pain," Journal of Medicinal Chemistry, 2007, vol. 50 (11), pp. 2576-2582.
Poste G. et al., "Lipid Vesicles as Carriers for Introducing Biologically Active Materials into Cells," Methods in Cell Biology, 1976, vol. 14, pp. 33-71.
Roeloffs R., et al., "In Vivo Profile of ICA-27243 [N-(6-Chloro-pyridin-3-yl)-3,4-difluoro-benzamide], a Potent and Selective KCNQ2/Q3(Kv7.2/Kv7.3) Activator in Rodent Anticonvulsant Models," The Journal of Pharmacology and Experimental Therapeutics, 2008, vol. 326 (3), pp. 818-828.
Roza C., et al., "Retigabine, the Specific KCNQ Channel Opener, Blocks Ectopic Discharges in Axotomized Sensory Fibres," Pain, 2008, vol. 138 (3), pp. 537-545.
Settepani J.A., et al., "Heterocyclic Amines. II. Synthesis of 3,5-Diaminopyrazole," Journal of Organic Chemistry, 1968, vol. 33, pp. 2606.
Sotty F., et al., "Antipsychotic-Like Effect of Retigabine [N-(2-Amino-4-(Fluorobenzylamino)-Phenyl)Carbamic Acid Ester], A Kcnq Potassium Channel Opener, Via Modulation of Mesolimbic Dopaminergic Neurotransmission," The Journal of Pharmacology and Experimental Therapeutics, 2009, vol. 328 (3), pp. 951-962.
Streng T., et al., "Urodynamic Effects of the K+ Channel (KCNQ) Opener Retigabine in Freely Moving, Conscious Rats ," The Journal of Urology, 2004, vol. 172 (5 pt 1), pp. 2054-2058.
Thomson, J.F., "Physiological Effects of D20 in Mammals," Annals of the New York Academy of Sciences, 1960, vol. 84, pp. 736-744.
Wickenden A.D., et al., "Retigabine, A Novel Anti-Convulsant, Enhances Activation of KCNQ2/Q3 Potassium Channels," Molecular Pharmacology, 2000, vol. 58 (3), pp. 591-600.
Wu, Y.J., et al., "Fluorine Substitution Can Block Cyp3a4 Metabolism-Dependent Inhibition: Identification of (S)-N-[1-(4-Fluoro-3-Morpholin-4-Ylphenyl)Ethyl]-3-(4-Fluorophenyl)Acrylamide as an Orally Bioavailable KCNQ2 Opener Devoid of Cyp3a4 Metabolism-Dependent Inhibition," The Journal of Medicinal Chemistry, 2003, vol. 46 (18), pp. 3778-3781.
Wu Y.J., et al., "(S)-N-[1-(3-Morpholin-4-Ylphenyl)Ethyl]-3-Phenylacrylamide: An Orally Bioavailable KCNQ2 Opener with Significant Activity in a Cortical Spreading Depression Model of Migraine," The Journal of Medicinal Chemistry, 2003, vol. 46 (15), pp. 3197-3200.

* cited by examiner

POTASSIUM CHANNEL MODULATORS

CROSS-REFERENCE TO RELATED APPLICATIONS

This application claims the benefit of provisional application Ser. No. 61/414,275 filed Nov. 16, 2010, which is hereby incorporated by reference as if set forth in its entirety.

TECHNICAL FIELD AND BACKGROUND

Compounds that are potassium channel modulators, compositions comprising such compounds, and methods of treating conditions and disorders using such compounds and compositions are disclosed.

Potassium channels are membrane-bound proteins responsible for regulating the flow of potassium ions through a cell membrane. The KCNQ (or $K_v7$) family is an important class of potassium channel that plays a key role in the process of neuronal excitability. There are five recognized subtypes of KCNQ channel: KCNQ1, KCNQ2, KCNQ3, KCNQ4, and KCNQ5. The KCNQ2-KCNQ5 subtypes represent the neuronal KCNQ subtypes. Miceli, *Curr. Op. Pharmacol.*, 2008, 8, 65. Functional KCNQ channels are formed by the assemblage of four individual subunits into a homotetramer or heterotetramer. The KCNQ2/3 channel is composed of a heterotetrameric assemblage of the KCNQ2 and KCNQ3 proteins.

The neuronal KCNQ channels are voltage-gated potassium channels that control cellular excitability by hyperpolarizing membrane potential, reducing action potential firing, and decreasing neurotransmitter release. Jentsch, *Nature Reviews Neurosci.*, 2000, 1, 21; Dalby-Brown, *Curr. Top. Med. Chem.*, 2006, 6, 999; Munro, *J. Med. Chem.*, 2007, 50, 2576. Neuronal KCNQ channels become activated on cellular depolarization (i.e., a change in voltage). See, Roza et al., *Pain*, 2008, 138, 537; Wickenden et al., *Mol. Pharmacol.*, 2000, 58, 591.

Activation of KCNQ channels by KCNQ openers causes an outflow of potassium ions from the cell, reducing the membrane potential (i.e., hyperpolarization), and thereby decreasing cellular excitability and action potential generation. Miceli, *Curr. Op. Pharmacol.*, 2008, 8, 65. In view of the role that KCNQ channels play in controlling cellular excitability and their distribution throughout the nervous system, KCNQ channel openers have been reported to have therapeutic utility in the treatment of a number of disorders characterized by abnormal neuronal excitability including: epilepsy, pain, migraine, anxiety, and overactive bladder. Dalby-Brown, *Curr. Top. Med. Chem.*, 2006, 6, 999; Streng, *J. Urol.*, 2004, 172, 2054. The dampening effect on neuronal excitability of KCNQ opening has also been implicated as a mechanism to inhibit the release of neurotransmitters (e.g., dopamine and serotonin) involved in schizophrenia, anxiety, and substance abuse. Hansen, *J. Physiol.* 2008, 1823.

A number of KCNQ openers, including flupirtine and retigabine, have been reported to be efficacious in treating various pain states in humans or rodents. These pain states include neuropathic pain (including diabetic polyneuropathy), inflammatory pain, persistent pain, cancer pain, and postoperative pain. Munro, *J. Med. Chem.*, 2007, 50, 2576; Dalby-Brown, *Curr. Top. Med. Chem.*, 2006, 6, 999. Thus, KCNQ openers have utility in treating a variety of painful conditions including, but not limited to, the foregoing types of pain.

The utility of KCNQ openers in the treatment of epilepsy is shown by the anticonvulsant and antiseizure activity of flupirtine, retigabine, and ICA-27243. Roeloffs, *J. Pharmacol. Exp. Ther.*, 2008, 326, 818; Miceli, *Curr. Op. Pharmacol.*, 2008, 8, 65; Blackburn-Munro, *CNS Drug Rev.*, 2005, 11, 1.

The utility of KCNQ openers in the treatment of migraine is indicated by the activity of KCNQ openers in an animal model of migraine. Wu, *J. Med. Chem.*, 2003, 46, 3197; Wu, *J. Med. Chem.*, 2003, 46, 3778.

The utility of KCNQ openers as anxiolytics is indicated by the activity of retigabine in animal models of anxiety. Dalby-Brown, *Curr. Top. Med. Chem.*, 2006, 6, 999.

The utility of KCNQ openers in the treatment of schizophrenia is indicated by the ability of retigabine to inhibit the activity of dopaminergic systems (Hansen, *J. Pharmacol. Exp. Ther.*, 2006, 318, 1006; Hansen, *J. Physiol.* 2008, 1823; Sotty, *J. Pharmacol. Exp. Ther.*, 2009, 328, 951) and by retigabine's efficacy in animal models of schizophrenia. Sotty, *J. Pharmacol. Exp. Ther.*, 2009, 328, 951.

Flupirtine and retigabine both possess liabilities in terms of adverse effects, including: asthenia, ataxia, insomnia, headache, drowsiness, dizziness, somnolence, dry mouth, nausea, vomiting, gastric and abdominal discomfort, sedation or loss of motor coordination. Miceli, *Curr. Op. Pharmacol.*, 2008, 8, 65; Munro, *J. Med. Chem.*, 2007, 50, 2576; Blackburn-Munro, *CNS Drug Rev.*, 2005, 11, 1. These adverse effects can be related to activation of one or more KCNQ subtypes not primarily responsible for the desirable therapeutic response. Thus, there is a need for KCNQ openers with efficacy in one or more of the foregoing disorders, states, or conditions, but without the side-effects of flupirtine or retigabine. KCNQ openers that selectively activate a particular subtype or subtypes can possess such efficacy with reduced side-effects.

SUMMARY

Provided herein are compounds of formula (I)

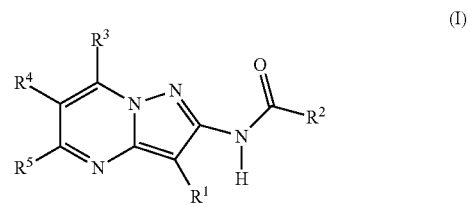

(I)

or a pharmaceutically acceptable salts, solvates, salts of solvates, or combinations thereof, wherein $R^1$ is alkyl, alkenyl, alkynyl, haloalkyl, $C(O)OR^{1a}$, $S(O)_2 G^1$, or $G^{1a}$; wherein each of the alkyl, alkenyl, haloalkyl, and alkynyl radical is independently unsubstituted or substituted with 1, 2, or 3 substituents independently selected from the group consisting of $OR^{1a}$, $NR^{1b}R^{1c}$, $N(R^{1b})S(O)_2R^{1d}$, $SR^{1a}$, $SO_2R^{1d}$, $S(O)_2NR^{1b}R^{1c}$, $C(O)NR^{1b}R^{1c}$, $C(O)OR^{1a}$, and $G^{1b}$;

$R^{1a}$, $R^{1b}$ and $R^{1c}$, at each occurrence, are each independently hydrogen, alkyl, haloalkyl, alkenyl, alkynyl, $G^{1b}$, or —($C_1$-$C_6$ alkylenyl)-$G^{1b}$;

$R^{1d}$, at each occurrence, are each independently alkyl, haloalkyl, alkenyl, alkynyl, $G^{1b}$, or —($C_1$-$C_6$ alkylenyl)-$G^{1b}$;

$G^1$, $G^{1a}$, and $G^{1b}$, at each occurrence, are each independently cycloalkyl, cycloalkenyl, heterocycle, heteroaryl, or aryl;

$R^2$ is —$C(R^{2x})$=$C(R^{2y})(R^{2z})$, alkyl, haloalkyl, alkenyl, alkynyl, $OR^{2a}$, $NR^{2a}R^{2b}$, or $G^{2a}$, wherein the alkyl, haloalkyl, alkenyl, and alkynyl are each independently unsubstituted or substituted with 1, 2, or 3 substituents independently selected from the group consisting of $OR^{2a}$, $NR^{2b}R^{2c}$, $SR^{2a}$, $S(O)R^{2d}$, $SO_2R^{2d}$, and $G^{2b}$;

$R^{2x}$ is hydrogen, alkyl, or haloalkyl;

$R^{2y}$ and $R^{2z}$, together with the carbon atom to which they are attached, form a cycloalkyl or heterocycle ring;

$R^{2a}$, $R^{2b}$, and $R^{2c}$, at each occurrence, are each independently hydrogen, alkyl, haloalkyl, alkenyl, alkynyl, $G^{2b}$, or —($C_1$-$C_6$ alkylenyl)-$G^{2b}$;

$R^{2d}$, at each occurrence, is independently alkyl, haloalkyl, alkenyl, alkynyl, $G^{2b}$, or —($C_1$-$C_6$ alkylenyl)-$G^{2b}$;

$G^{2a}$ is cycloalkyl, cycloalkenyl, heterocycle, heteroaryl, or bicyclic aryl;

$G^{2b}$, at each occurrence, is each independently cycloalkyl, cycloalkenyl, heterocycle, heteroaryl, or aryl;

$G^1$, $G^{1a}$, $G^{1b}$, $G^{2a}$, and $G^{2b}$, and the ring formed by $R^{2y}$, $R^{2z}$, and the carbon atom to which they are attached, are each independently unsubstituted or substituted with 1, 2, 3, 4, or 5 substituents independently selected from the group consisting of halogen, alkyl, alkenyl, alkynyl, haloalkyl, oxo, $NO_2$, CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —($C_1$-$C_6$ alkylenyl)-$OR^f$, —($C_1$-$C_6$ alkylenyl)-$OC(O)R^f$, —($C_1$-$C_6$ alkylenyl)-$OC(O)N(R^f)_2$, —($C_1$-$C_6$ alkylenyl)-$S(O)_2R^e$, —($C_1$-$C_6$ alkylenyl)-$S(O)_2N(R^f)_2$, —($C_1$-$C_6$ alkylenyl)-$C(O)R^f$, —($C_1$-$C_6$ alkylenyl)-$C(O)OR^f$, —($C_1$-$C_6$ alkylenyl)-$C(O)N(R^f)_2$, —($C_1$-$C_6$ alkylenyl)-$N(R^f)_2$, —($C_1$-$C_6$ alkylenyl)-$N(R^f)C(O)R^f$, —($C_1$-$C_6$ alkylenyl)-$N(R^f)S(O)_2R^e$, —($C_1$-$C_6$ alkylenyl)-$N(R^f)C(O)O(R^e)$, —($C_1$-$C_6$ alkylenyl)-$N(R^f)C(O)N(R^f)_2$, and —($C_1$-$C_6$ alkylenyl)-CN;

$R^f$, at each occurrence, is independently hydrogen, $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^e$, at each occurrence, is independently $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^g$, at each occurrence, is independently hydrogen, $C_1$-$C_4$ alkyl, $C_1$-$C_4$ haloalkyl, monocyclic cycloalkyl, or —($C_1$-$C_6$ alkylenyl)-(monocyclic cycloalkyl); wherein the monocyclic cycloakyl, alone or as part of the group, is optionally substituted with 1, 2, 3, 4, or 5 substituents independently selected from the group consisting of alkyl, haloalkyl, oxo, OH, and alkoxy;

$G^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy; and $R^3$, $R^4$, and $R^5$ are each independently hydrogen, halogen, alkyl, or haloalkyl.

Compounds described herein or pharmaceutically acceptable salts or solvates thereof are modulators of KCNQ potassium channels and are thus useful in the treatment of diseases, disorders, or conditions of a subject that are responsive to the modulation of the potassium channels.

Compounds of formula (I) are openers of KCNQ potassium channels and are useful in the treatment of conditions or disorders that are responsive to the opening of the KCNQ potassium channels, including pain.

Another aspect is related to pharmaceutical compositions comprising therapeutically effective amounts of one or more compound(s) described herein or pharmaceutically acceptable salts or solvates thereof, in combination with one or more pharmaceutically acceptable carrier(s). Such compositions can be administered in accordance with a method of the invention, typically as part of a therapeutic regimen for treatment or prevention of conditions and disorders related to the modulation of KCNQ channels. More particularly, the methods are useful for treating disorders or conditions related to pain such as neuropathic pain (including diabetic polyneuropathy), nociceptive pain, persistent pain, osteoarthritic pain, cancer pain, inflammatory pain, postoperative pain, fibromyalgia, chronic widespread pain, musculoskeletal pain, myofascial pain, and temporomandibular joint (TMJ) pain, as well as epilepsy, migraine, overactive bladder, schizophrenia, anxiety, and substance abuse.

Further provided herein are the use of the present compounds or pharmaceutically acceptable salts or solvates thereof, in the manufacture of a medicament for the treatment of the disease conditions described above, alone or in combination with one or more pharmaceutically acceptable carrier(s), particularly for the treatment or alleviation of disorders or conditions related to neuropathic pain (including diabetic polyneuropathy), nociceptive pain, persistent pain, osteoarthritic pain, cancer pain, inflammatory pain, migraine pain, postoperative pain, fibromyalgia, chronic widespread pain, musculoskeletal pain, myofascial pain, temporomandibular joint (TMJ) pain, epilepsy, migraine, overactive bladder, schizophrenia, anxiety, and substance abuse.

The compounds, compositions comprising the compounds or pharmaceutically acceptable salts or solvates thereof, and methods for treating or preventing conditions and disorders by administering the compounds or compositions thereof are further described herein.

These and other objectives are described in the following paragraphs. These objectives should not be deemed to narrow the scope of the invention.

DETAILED DESCRIPTION

Provided herein are compounds of formula (I)

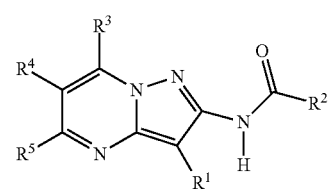

(I)

wherein $R^1$, $R^2$, $R^3$, $R^4$, and $R^5$ are as defined above in the Summary and below in the Detailed Description. Compositions comprising such compounds and methods for treating conditions and disorders using such compounds and compositions are also disclosed.

In various embodiments, there can be variables that occur more than one time in any substituent or in the compound or any other formulae herein. Definition of a variable on each occurrence is independent of its definition at another occurrence. Further, combinations of variables or substituents are permissible only if such combinations result in stable compounds. Stable compounds are compounds that can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of alkenyl include buta-2,3-dienyl, ethenyl (vinyl), 3,3-dimethylbut-1-en-1-yl, 2-propenyl, prop-1-en-1-yl, 2-methyl-2-propenyl, 3-butenyl, 4-pentenyl, 5-hexenyl, 2-heptenyl, 2-methyl-1-heptenyl, and 3-decenyl.

The term "alkenylene" or "alkenylenyl" means a divalent group derived from a straight or branched chain hydrocarbon of 2 to 4 carbon atoms and contains at least one carbon-carbon double bond. Representative examples of alkenylene and alkenylenyl include, but are not limited to, —CH═CH— and —CH$_2$CH═CH—.

The term "alkoxy" as used herein, means an alkyl group, as defined herein, appended to the parent molecular moiety through an oxygen atom. 1Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_1$-$C_4$ alkyl" means a straight or branched chain, saturated hydrocarbon containing 1 to 4 carbon atoms. Examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 2,2-dimethylethyl, 2,2-dimethylpropyl, 1-methylpropyl, 2-methylpropyl, 1-ethylpropyl, 2,2-dimethylbutyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain, for example, of 1 to 10 carbon atoms or of 1 to 6 carbon atoms. Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means a straight or branched chain hydrocarbon group containing from 2 to 4 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (e.g. 2,3-dihydro-1H-indenyl), indenyl, naphthyl, dihydronaphthalenyl, and tetrahydronaphthalenyl. The bicyclic aryl is attached to the parent molecular moiety through any carbon atom contained within the bicyclic ring system and can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms, and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring such as, for example, bicyclo[3.1.0]hexyl. Tricyclic cycloalkyls are exemplified by a bicyclic cycloalkyl fused to a monocyclic cycloalkyl. The monocyclic, bicyclic, and tricyclic cycloalkyls can have one or two alkylene bridges, each of 1, 2, 3, or 4 carbon atoms, and each linking two non-adjacent carbon atoms of the ring system. Non-limiting examples of cycloalkyls having one or two alkylene bridges include, but not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The cycloalkyls of the present application can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic and the bicyclic cycloalkenyl rings can contain one or two alkylene bridges, each consisting of one, two, or three carbon atoms and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five, or six hydrogen atoms are replaced by halogen. The term "$C_1$-$C_4$ haloalkyl" means a $C_1$-$C_4$ alkyl group, as defined herein, in which one, two, three, four, five, or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloalkoxy" as used herein, means an alkoxy group, as defined herein, in which one, two, three, four, five or six hydrogen atoms are replaced by halogen. Representative examples of haloalkoxy include, but are not limited to, 2-fluoroethoxy, 2,2,2-trifluoroethoxy, trifluoromethoxy, and difluoromethoxy.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contain zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, and 2,3-dihydrobenzothienyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic, bicyclic, and tricyclic heterocycle groups of the present application can have one or two alkylene bridges of 1, 2, 3, or 4 carbon atoms, or one or two alkenylene bridges of two, three, or four carbon atoms, or combinations thereof. Examples of the heterocycles having such alkylene or alkenylene bridge(s) include, but are not limited to, azabicyclo[3.2.1]octane, azabicyclo[2.2.1]heptyl (including 2-azabicyclo[2.2.1]hept-2-yl), 2,3-dihydro-1H-indolyl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The heterocycles of the present application can be unsubstituted or substituted, and are connected to the parent molecular moiety through any substitutable carbon atom or any substitutable nitrogen atom contained within the rings. The nitrogen and sulfur heteroatoms in the heterocycle rings can optionally be oxidized and the nitrogen atoms can optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring can contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any substitutable carbon atom or any substitutable nitrogen atom contained within the ring systems.

The term "heteroatom" as used herein, means a nitrogen, oxygen, or sulfur atom.

The term "hydroxyl" or "hydroxy" means a —OH group.

The term "oxo" as used herein, means a =O group.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "modulate" refers to the ability of a compound to increase or decrease the function, or activity, of KCNQ channels. "Modulation", as used herein in its various forms, is intended to encompass antagonism, agonism, partial antagonism and/or partial agonism of the activity associated with KCNQ channels. KCNQ channel activators are compounds that, e.g., bind to, stimulate, increase, open, activate, or facilitate KCNQ channels such as, but not limited to, KCNQ2, and/or KCNQ3, and/or KCNQ2/3 potassium channels. Activation of KCNQ channels encompasses either or both of: (1) increasing current through a KCNQ channel; or (2) shifting the half-activation potential of KCNQ channels to lower voltages (i.e. a hyperpolarizing shift of the V1/2 for activation).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. Compounds

KCNQ channel modulators have formula (I) as described above.

Particular values of variable groups in compounds of formula (I) are as follows. Such values can be used where appropriate with any of the other values, definitions, claims or embodiments defined hereinbefore or hereinafter.

$R^3$, $R^4$, and $R^5$ have values as disclosed in the Summary. In certain embodiments, $R^3$, $R^4$, and $R^5$ are each independently hydrogen or alkyl (e.g. $C_1$-$C_6$ alkyl such as, but not limited to, methyl). In certain embodiments, $R^3$, $R^4$, and $R^5$ are hydrogen. In certain embodiments, $R^3$ and $R^5$ are alkyl (e.g. $C_1$-$C_6$ alkyl such as, but not limited to, methyl), and $R^4$ is hydrogen. In certain embodiments, $R^3$ and $R^5$ are hydrogen, and $R^4$ is alkyl (e.g. $C_1$-$C_6$ alkyl such as, but not limited to, methyl). In certain embodiments, $R^3$ and $R^4$ are hydrogen, and $R^5$ is alkyl (e.g. $C_1$-$C_6$ alkyl such as, but not limited to, methyl). In certain embodiments, $R^4$ and $R^5$ are hydrogen, and $R^3$ is alkyl (e.g. $C_1$-$C_6$ alkyl such as, but not limited to, methyl).

In compounds of formula (I), $R^1$ has values as disclosed in the Summary.

In certain embodiments, $R^1$ is alkyl, alkenyl, alkynyl, haloalkyl, C(O)OR$^{1a}$, or G$^{1a}$; wherein each of the alkyl, alkenyl, and alkynyl radical is independently unsubstituted or substituted with one substituent selected from the group consisting of N(R$^{1b}$)S(O)$_2$R$^{1d}$, C(O)NR$^{1b}$R$^{1c}$, C(O)OR$^{1a}$, and G$^{1b}$. In certain embodiments, $R^1$ is alkyl, alkenyl, alkynyl, haloalkyl, C(O)OR$^{1a}$, or G$^{1a}$; wherein each of the alkyl, alkenyl, and alkynyl radical is independently unsubstituted or substituted with a $G^{1b}$ group. $R^{1a}$, $R^{1b}$, $R^{1c}$, $R^{1d}$, $G^{1a}$, and $G^{1b}$ are as disclosed in the Summary and embodiments herein below.

In certain embodiments, $R^1$ is alkyl (e.g. $C_3$-$C_6$ alkyl such as, but not limited to, isopropyl, tert-butyl, 2,2-dimethylpropyl), haloalkyl, alkenyl (e.g. $C_2$-$C_6$ alkenyl such as, but not limited to, 3,3-dimethylbut-1-en-1-yl, vinyl, prop-1-en-1-yl), or alkynyl (e.g. $C_2$ alkynyl). In other embodiments, $R^1$ is alkyl (e.g. $C_3$-$C_6$ alkyl such as, but not limited to, isopropyl, tert-butyl, 2,2-dimethylpropyl), alkenyl (e.g. $C_2$-$C_6$ alkenyl such as, but not limited to, 3,3-dimethylbut-1-en-1-yl, vinyl, prop-1-en-1-yl), or alkynyl (e.g. $C_2$ alkynyl). In certain embodiments, $R^1$ is alkyl (e.g. $C_3$-$C_6$ alkyl such as, but not limited to, isopropyl, tert-butyl, 2,2-dimethylpropyl), alkenyl, or haloalkyl. In certain embodiment, $R^1$ is alkyl (e.g. $C_3$-$C_6$ alkyl such as, but not limited to, isopropyl, tert-butyl, 2,2-dimethylpropyl). The alkyl, alkenyl, and the alkynyl groups of $R^1$ are each optionally substituted as described in the Summary and embodiments herein below. In certain embodiments, the alkyl and the alkenyl groups of $R^1$ are unsubstituted.

In certain embodiments, $R^1$ is alkyl (e.g. methyl, ethyl), alkenyl (e.g. vinyl) or alkynyl (e.g. ethynyl), each of which is independently substituted with one $G^{1b}$ group wherein $G^{1b}$ is as defined in the Summary and embodiments herein. For example, $G^{1b}$ is cycloalkyl (e.g. monocyclic cycloalkyl such as, but not limited to, cyclohexyl), heteroaryl (e.g. monocyclic heteroaryl such as, but not limited to, pyridinyl, pyrimidinyl), or aryl (e.g. phenyl, naphthyl). In certain embodiments, $G^{1b}$ is aryl. In certain embodiments, $G^{1b}$ is phenyl. In certain embodiments, $G^{1b}$ is monocyclic heteroaryl (for example, but not limited to, pyridinyl, pyrimidinyl). In certain embodiments, $G^{1b}$ is monocyclic cycloalkyl (for example, but not limited to, cyclohexyl).

In the embodiments wherein $R^1$ is $COOR^{1a}$, $R^{1a}$ is as disclosed in the Summary and embodiments herein. For example, in certain embodiments, $R^{1a}$ is alkyl such as, but not limited to, methyl.

In the embodiments wherein $R^1$ is $G^{1a}$, $G^{1a}$ is as described in the Summary and embodiments herein. For example, in certain embodiments, $G^{1a}$ is cycloalkyl (e.g. monocyclic cycloalkyl such as, but not limited to, cyclohexyl), heterocycle (e.g. monocyclic heterocycle such as, but not limited to, morpholinyl, tetrahydropyranyl), heteroaryl (e.g. monocyclic heteroaryl such as, but not limited to, pyridinyl, pyrimidinyl), or aryl (e.g. phenyl, naphthyl). In certain embodiments, $G^{1a}$ is cycloalkyl (e.g. monocyclic cycloalkyl such as, but not limited to, cyclohexyl), heteroaryl (e.g. monocyclic heteroaryl such as, but not limited to, pyridinyl, pyrimidinyl), or aryl (e.g. phenyl, naphthyl). In certain embodiments, $G^{1a}$ is phenyl. In certain embodiments, $G^{1a}$ is monocyclic heteroaryl (for example, but not limited to, pyridinyl, pyrimidinyl). In certain embodiments, $G^{1a}$ is monocyclic cycloalkyl (for example, but not limited to, cyclohexyl). In certain embodiments, $G^{1a}$ is monocyclic heterocycle (e.g. morpholinyl, tetrahydropyranyl).

Each of the foregoing $G^{1a}$ and $G^{1b}$ groups are independently unsubstituted or substituted as described in the Summary. In certain embodiments, the optional substituents of $G^{1a}$ and $G^{1b}$ groups, for example, are independently alkyl (e.g. $C_1$-$C_6$ alkyl such as, but not limited to, methyl, ethyl), halogen (e.g. Cl, F), haloalkyl (e.g. trifluoromethyl), —C(O)OR$^f$, —C(O)N(R$^f$)$_2$, —(C$_1$-$C_6$ alkylenyl)-C(O)OR$^f$, and —OR$^f$ wherein R$^f$ is as disclosed in the Summary. In the embodiments where $G^{1b}$ and $G^{1a}$ are optionally substituted with —OR$^f$, C(O)OR$^f$, —C(O)N(R$^f$)$_2$, and —(C$_1$-$C_6$ alkyle-nyl)-C(O)OR$^f$, R$^f$, for example, is hydrogen, $C_1$-$C_4$ alkyl (e.g. methyl), or $C_1$-$C_4$ haloalkyl (e.g. trifluoromethyl).

In compounds of formula (I), $R^2$ has values as disclosed in the Summary. In certain embodiments, $R^2$ is —C(R$^{2x}$)=C(R$^{2y}$)(R$^{2z}$), alkyl, alkenyl, haloalkyl, OR$^{2a}$, or NR$^{2a}$R$^{2b}$, wherein the alkyl and the alkenyl group is independently unsubstituted or substituted with a substituent selected from the group consisting of OR$^{2a}$, SR$^{2a}$, S(O)R$^{2d}$, SO$_2$R$^{2d}$, and $G^{2b}$. R$^{2x}$, R$^{2y}$, R$^{2z}$, R$^{2a}$, R$^{2b}$, R$^{2d}$, and $G^{2b}$ are as described in the Summary and embodiments herein below.

In certain embodiments, $R^2$ is —C(R$^{2x}$)=C(R$^{2y}$)(R$^{2z}$). In certain embodiments, R$^{2y}$ and R$^{2z}$, together with the carbon atom to which they are attached, form an optionally substituted cycloalkyl ring (such as, but not limited to, optionally substituted monocyclic cycloalkyl). In certain embodiments, R$^{2y}$ and R$^{2z}$, together with the carbon atom to which they are attached, form an optionally substituted cyclohexyl ring.

In certain embodiments, $R^2$ is alkyl, alkenyl, or haloalkyl. In certain embodiments, $R^2$ is haloalkyl or alkyl. In certain embodiments $R^2$ is $C_3$-$C_6$ alkyl such as, but are not limited to, 2,2-dimethylpropyl, 2,2-dimethylbutyl. The alkyl and the alkenyl groups of $R^2$ are optionally substituted as described in the Summary and embodiments herein below. In certain embodiments the alkyl group of $R^2$ is unsubstituted.

For example, in certain embodiments $R^2$ is alkyl substituted with a substituent selected from the group consisting of OR$^{2a}$, SR$^{2a}$, S(O)R$^{2d}$, and SO$_2$R$^{2d}$. In certain embodiments, $R^2$ is $C_1$-$C_4$ alkyl (e.g. methyl, ethyl, 2,2 dimethylethyl) substituted with a substituent selected from the group consisting of OR$^{2a}$, SR$^{2a}$, S(O)R$^{2d}$, and SO$_2$R$^{2d}$. In yet other embodiments, $R^2$ is $C_1$-$C_2$ (such as, but not limited to, methyl, ethyl) alkyl substituted with a substituent selected from the group consisting of OR$^{2a}$, SR$^{2a}$, S(O)R$^{2d}$, and SO$_2$R$^{2d}$. R$^{2a}$ and R$^{2d}$ have values as defined in the Summary and embodiments herein. For example, R$^{2a}$ and R$^{2d}$ are each independently $G^{2b}$ wherein $G^{2b}$ is as disclosed in the Summary and herein. In certain embodiments, R$^{2a}$ and R$^{2d}$ are each independently $G^{2b}$ wherein $G^{2b}$ is an optionally substituted cycloalkyl such as, but not limited to, an optionally substituted monocyclic cycloalkyl (e.g. optionally substituted cyclopentyl). The optional substituents of $G^{2b}$ are as disclosed in the Summary and herein below.

In certain embodiments, $R^2$ is alkyl or alkenyl substituted with a $G^{2b}$ group. In certain embodiments, $R^2$ is $C_1$-$C_4$ alkyl (such as, but not limited to, e.g. methyl, ethyl, 2,2 dimethyl-ethyl) or a $C_2$-$C_4$ alkenyl substituted with a $G^{2b}$ group. In certain embodiments, $R^2$ is alkyl (e.g $C_1$-$C_4$ alkyl such as, but not limited to, methyl, ethyl, 2,2 dimethylethyl) substituted with a $G^{2b}$ group. In certain embodiments, $R^2$ is an alkenyl (e.g. $C_2$-$C_4$ alkenyl) substituted with a $G^{2b}$ group. $G^{2b}$ for these embodiments is as disclosed in the Summary and embodiments herein. For example, $G^{2b}$ is cycloalkyl (such as, but not limited to, cyclopropyl, cyclobutyl, cyclopentyl, cyclohexyl, bicyclo[3.1.0]hexyl, bicyclo[3.1.1]heptyl, bicyclo[2.2.1]heptyl, adamantyl), aryl (such as, but not limited to, phenyl, 2,3-dihydroindenyl), or heteroaryl (such as, but not limited to, pyridinyl). In certain embodiments, $G^{2b}$ is cycloalkyl (such as, but not limited to, cyclopropyl, cyclobutyl, cyclopentyl, cyclohexyl, bicyclo[3.1.0]hexyl, bicyclo[3.1.1]heptyl, bicyclo[2.2.1]heptyl, adamantyl). In certain embodiments, $G^{2b}$ is aryl (such as, but not limited to, phenyl, 2,3-dihydro-1H-indenyl). In other embodiments, $G^{2b}$ is heteroaryl (such as, but not limited to, pyridinyl). Each $G^{2b}$ group is optionally substituted as described in the Summary and herein below.

In certain embodiments, $R^2$ is —$OR^{2a}$ wherein $R^{2a}$ is as described in the Summary and embodiments herein. In certain embodiments, $G^{2b}$ is —$OR^{2a}$ wherein $R^{2a}$ is alkyl (e.g. tert-butyl).

In certain embodiments, $R^2$ is —$NR^{2a}R^{2b}$ wherein $R^{2a}$ and $R^{2b}$ are as described in the Summary and embodiments herein. In certain embodiments, $R^2$ is —$NR^{2a}R^{2b}$ wherein $R^{2a}$ is hydrogen and $R^{2b}$ is $G^{2b}$ or —$(C_1-C_6$ alkylenyl)-$G^{2b}$. $G^{2b}$ is as described in the Summary and embodiments herein. For example, $G^{2b}$ is cycloalkyl (e.g. monocyclic cycloalkyl such as, but not limited to, cyclopentyl, cyclohexyl), heterocycle (e.g. monocyclic heterocycle such as, but not limited to, tetrahydropyranyl). Each $G^{2b}$ group is optionally substituted as described in the Summary and herein below.

Examples of the optional substituents of $G^{2b}$ include, but are not limited to, alkyl (e.g. $C_1-C_6$ alkyl such as, but not limited to, methyl, ethyl, isopropyl), halogen (e.g. Cl, F), haloalkyl (e.g. trifluoromethyl), $C(O)N(R^f)_2$, $N(R^f)C(O)R^f$, and —$OR^f$ wherein $R^f$ is as disclosed in the Summary. In certain embodiments where $G^{2b}$ is optionally substituted with $C(O)N(R^f)_2$, $N(R^f)C(O)R^f$, and —$OR^f$, $R^f$, for example, is hydrogen, $C_1-C_4$ alkyl (e.g. methyl), or $C_1-C_4$ haloalkyl (e.g. trifluoromethyl).

It is appreciated that compounds of formula (I) with combinations of the above embodiments, including particular, more particular and preferred embodiments are contemplated.

Accordingly, one aspect relates to a group of compounds of formula (I) wherein $R^1$ is haloalkyl, optionally substituted alkyl, optionally substituted alkenyl, or optionally substituted alkynyl, and $R^2$ is haloalkyl or optionally substituted alkyl, wherein the optional substituents are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is haloalkyl or unsubstituted alkyl.

Another aspect relates to a group of compounds of formula (I) wherein $R^1$ is haloalkyl, optionally substituted alkyl, optionally substituted alkenyl, or optionally substituted alkynyl, and $R^2$ is alkyl substituted with a substituent selected from the group consisting of $OR^{2a}$, $SR^{2a}$, $S(O)R^{2d}$, and $S(O)_2R^{2d}$. $R^{2a}$ and $R^{2d}$ are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is alkyl or alkenyl, each substituted with a $G^{2b}$ group. $G^{2b}$ is as disclosed in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is alkyl or alkenyl, each substituted with a $G^{2b}$ group wherein $G^{2b}$ is cycloalkyl, aryl, or heteroaryl, each of which is optionally substituted as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is alkyl or alkenyl, each substituted with a $G^{2b}$ group wherein $G^{2b}$ is optionally substituted aryl. The optional substituents of $G^{2b}$ are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is alkyl or alkenyl, each substituted with a $G^{2b}$ group wherein $G^{2b}$ is optionally substituted phenyl. The optional substituents of $G^{2b}$ are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is alkyl or alkenyl, each substituted with a $G^{2b}$ group wherein $G^{2b}$ is optionally substituted cycloalkyl. The optional substituents of $G^{2b}$ are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is alkyl or alkenyl, each substituted with a $G^{2b}$ group wherein $G^{2b}$ is optionally substituted heteroaryl. The optional substituents of $G^{2b}$ are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is —$OR^{2a}$ wherein $R^{2a}$ and $R^{2b}$ are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is —$NR^{2a}R^{2b}$ wherein $R^{2a}$ and $R^{2b}$ are as described in the Summary and embodiments herein above.

Another aspect relates to a group of compounds of formula (I) wherein $R^1$ is haloalkyl, optionally substituted alkyl, optionally substituted alkenyl, or optionally substituted alkynyl, and $R^2$ is —$C(R^{2x})$=$C(R^{2y})(R^{2z})$ wherein $R^{2x}$, $R^{2y}$, and $R^{2z}$ are as described in the Summary and embodiments herein above.

Another aspect relates to a group of compounds of formula (I) wherein $R^1$ is haloalkyl or unsubstituted alkyl, and $R^2$ is alkyl or haloalkyl, wherein the alkyl group is optionally substituted as described in the Summary and embodiments herein above.

Another aspect relates to a group of compounds of formula (I) wherein $R^1$ is haloalkyl or unsubstituted alkyl, and $R^2$ is haloalkyl or unsubstituted alkyl.

Another aspect relates to a group of compounds of formula (I) wherein $R^1$ is haloalkyl or unsubstituted alkyl, and $R^2$ is alkyl substituted with a substituent selected from the group consisting of $OR^{2a}$, $SR^{2a}$, $S(O)R^{2d}$, and $S(O)_2R^{2d}$. $R^{2a}$ and $R^{2d}$ are as described in the Summary and embodiments herein above.

Another aspect relates to a group of compounds of formula (I) wherein $R^1$ is haloalkyl or unsubstituted alkyl, and $R^2$ is alkyl or alkenyl, each substituted with a $G^{2b}$ group. $G^{2b}$ is as disclosed in the Summary and embodiments herein above.

Another aspect relates to a group of compounds of formula (I) wherein $R^1$ is haloalkyl or unsubstituted alkyl, and $R^2$ is alkyl or alkenyl, each substituted with a $G^{2b}$ group wherein $G^{2b}$ is cycloalkyl, aryl, or heteroaryl, each of which is optionally substituted as described in the Summary and embodiments herein above.

Another aspect relates to a group of compounds of formula (I) wherein $R^1$ is haloalkyl or unsubstituted alkyl, and $R^2$ is alkyl or alkenyl, each substituted with a $G^{2b}$ group wherein $G^{2b}$ is optionally substituted aryl. The optional substituents of $G^{2b}$ are as described in the Summary and embodiments herein above.

Another aspect relates to a group of compounds of formula (I) wherein $R^1$ is haloalkyl or unsubstituted alkyl, and $R^2$ is alkyl or alkenyl, each substituted with a $G^{2b}$ group wherein $G^{2b}$ is optionally substituted phenyl. The optional substituents of $G^{2b}$ are as described in the Summary and embodiments herein above.

Another aspect relates to a group of compounds of formula (I) wherein $R^1$ is haloalkyl or unsubstituted alkyl, and $R^2$ is alkyl or alkenyl, each substituted with a $G^{2b}$ group wherein $G^{2b}$ is optionally substituted cycloalkyl. The optional substituents of $G^{2b}$ are as described in the Summary and embodiments herein above.

Another aspect relates to a group of compounds of formula (I) wherein $R^1$ is haloalkyl or unsubstituted alkyl, and $R^2$ is alkyl or alkenyl, each substituted with a $G^{2b}$ group wherein $G^{2b}$ is optionally substituted heteroaryl. The optional substituents of $G^{2b}$ are as described in the Summary and embodiments herein above.

Another aspect relates to a group of compounds of formula (I) wherein $R^1$ is haloalkyl or unsubstituted alkyl, and $R^2$ is —$OR^{2a}$ wherein $R^{2a}$ is as described in the Summary and embodiments herein above.

Another aspect relates to a group of compounds of formula (I) wherein $R^1$ is haloalkyl or unsubstituted alkyl, and $R^2$ is —$NR^{2a}R^{2b}$ wherein $R^{2a}$ and $R^{2b}$ are as described in the Summary and embodiments herein above.

Another aspect relates to a group of compounds of formula (I) wherein $R^1$ is haloalkyl or unsubstituted alkyl, and $R^2$ is —$C(R^{2x})=C(R^{2y})(R^{2z})$ wherein $R^{2x}$, $R^{2y}$, and $R^{2z}$ are as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl or haloalkyl, wherein the alkyl group is optionally substituted as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is haloalkyl or unsubstituted alkyl. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl substituted with a substituent selected from the group consisting of $OR^{2a}$, $SR^{2a}$, $S(O)R^{2d}$, and $S(O)_2R^{2d}$. $R^{2a}$ and $R^{2d}$ are as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl or alkenyl, each substituted with a $G^{2b}$ group. $G^{2b}$ is as disclosed in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl or alkenyl, each substituted with a $G^{2b}$ group wherein $G^{2b}$ is cycloalkyl, aryl, or heteroaryl, each of which is optionally substituted as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl or alkenyl, each substituted with a $G^{2b}$ group wherein $G^{2b}$ is optionally substituted aryl. The optional substituents of $G^{2b}$ are as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl or alkenyl, each substituted with a $G^{2b}$ group wherein $G^{2b}$ is optionally substituted phenyl. The optional substituents of $G^{2b}$ are as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl or alkenyl, each substituted with a $G^{2b}$ group wherein $G^{2b}$ is optionally substituted cycloalkyl. The optional substituents of $G^{2b}$ are as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is alkyl or alkenyl, each substituted with a $G^{2b}$ group wherein $G^{2b}$ is optionally substituted heteroaryl. The optional substituents of $G^{2b}$ are as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is —$OR^{2a}$ wherein $R^{2a}$ is as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is —$NR^{2a}R^{2b}$ wherein $R^{2a}$ and $R^{2b}$ are as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is alkyl, alkenyl, or alkynyl, each of which is independently substituted with a $G^{1b}$ group, $G^{1b}$ is as described in the Summary and embodiments herein above, and $R^2$ is —$C(R^{2x})$=$C(R^{2y})(R^{2z})$ wherein $R^{2x}$, $R^{2y}$, and $R^{2z}$ are as described in the Summary and embodiments herein above. In certain embodiments, $G^{1b}$ is cycloalkyl, heteroaryl, or aryl. In certain embodiments, $G^{1b}$ is phenyl. In certain embodiments, $G^{1b}$ is monocyclic heteroaryl. In certain embodiments, $G^{1b}$ is monocyclic cycloalkyl. Each of the $G^{1b}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl or haloalkyl, wherein the alkyl group is optionally substituted as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is haloalkyl or unsubstituted alkyl. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl substituted with a substituent selected from the group consisting of $OR^{2a}$, $SR^{2a}$, $S(O)R^{2d}$, and $S(O)_2R^{2d}$. $R^{2a}$ and $R^{2d}$ are as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl or alkenyl, each substituted with a $G^{2b}$ group. $G^{2b}$ is as disclosed in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl or alkenyl, each substituted with a $G^{2b}$ group wherein $G^{2b}$ is cycloalkyl, aryl, or heteroaryl, each of which is optionally substituted as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl or alkenyl, each substituted with a $G^{2b}$ group wherein $G^{2b}$ is optionally substituted aryl. The optional substituents of $G^{2b}$ are as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl or alkenyl, each substituted with a $G^{2b}$ group wherein $G^{2b}$ is optionally substituted phenyl. The optional substituents of $G^{2b}$ are as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl or alkenyl, each substituted with a $G^{2b}$ group wherein $G^{2b}$ is optionally substituted cycloalkyl. The optional substituents of $G^{2b}$ are as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is alkyl or alkenyl, each substituted with a $G^{2b}$ group wherein $G^{2b}$ is optionally substituted heteroaryl. The optional substituents of $G^{2b}$ are as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is —$OR^{2a}$ wherein $R^{2a}$ is as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is —$NR^{2a}R^{2b}$ wherein $R^{2a}$ and $R^{2b}$ are as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Another aspect relates to a group of compounds of formula (I) wherein $R^1$ is $G^{1a}$, $G^{1a}$ is as described in the Summary and embodiments herein above, and $R^2$ is —$C(R^{2x})$=$C(R^{2y})(R^{2z})$ wherein $R^{2x}$, $R^{2y}$, and $R^{2z}$ are as described in the Summary and embodiments herein above. In certain embodiments, $G^{1a}$ is heterocycle, cycloalkyl, heteroaryl, or aryl. In certain embodiments, $G^{1a}$ is cycloalkyl, heteroaryl, or aryl. In certain embodiments, $G^{1a}$ is aryl. In certain embodiments, $G^{1a}$ is phenyl. In certain embodiments, $G^{1a}$ is monocyclic heteroaryl. In certain embodiments, $G^{1a}$ is monocyclic cycloalkyl. In certain embodiments, $G^{1a}$ is monocyclic heterocycle. Each of the $G^{1a}$ rings is optionally substituted as described in the Summary and embodiments herein above.

Within each group of compounds of formula (I) described above, $R^3$, $R^4$, and $R^5$ have values as described in the Summary and embodiments herein above.

Thus, for each group of compounds of formula (I) described above, examples of a subgroup include, but not limited to those wherein $R^3$, $R^4$, and $R^5$ are each independently hydrogen or alkyl.

Examples of another subgroup include those groups of compounds of formula (I) described above wherein $R^3$, $R^4$, and $R^5$ are hydrogen.

Examples of another subgroup include those groups of compounds of formula (I) described above wherein $R^3$ and $R^5$ are alkyl, and $R^4$ is hydrogen.

Examples of another subgroup include those groups of compounds of formula (I) described above wherein $R^3$ and $R^5$ are hydrogen, and $R^4$ is alkyl.

Exemplary compounds contemplated include, but are not limited to:

3,3-dimethyl-N-{3-[4-(trifluoromethoxy)phenyl]pyrazolo [1,5-a]pyrimidin-2-yl}butanamide;
N-[3-(4-fluorophenyl)pyrazolo[1,5-a]pyrimidin-2-yl]-3,3-dimethylbutanamide;
3,3-dimethyl-N-{6-methyl-3-[3-(trifluoromethoxy)phenyl] pyrazolo[1,5-a]pyrimidin-2-yl}butanamide;
2-[(1S,2S,5S)-6,6-dimethylbicyclo[3.1.1]hept-2-yl]-N-{3-[4-(trifluoromethoxy)phenyl]pyrazolo[1,5-a]pyrimidin-2-yl}acetamide;
2-cyclopentyl-N-[3-(4-fluorobenzyl)-6-methylpyrazolo[1,5-a]pyrimidin-2-yl]acetamide;
N-[3-(4-chlorophenyl)pyrazolo[1,5-a]pyrimidin-2-yl]-2-phenylacetamide;
N-[3-(4-chlorophenyl)pyrazolo[1,5-a]pyrimidin-2-yl]-3-cyclopentylpropanamide;
2-(3-methoxyphenyl)-N-{6-methyl-3-[4-(trifluoromethoxy) phenyl]pyrazolo[1,5-a]pyrimidin-2-yl}acetamide;
2-(4-fluorophenyl)-N-{7-methyl-3-[4-(trifluoromethoxy) phenyl]pyrazolo[1,5-a]pyrimidin-2-yl}acetamide;
N-[3-(2,2-dimethylpropyl)pyrazolo[1,5-a]pyrimidin-2-yl]-3-phenylpropanamide;
3-cyclohexyl-N-[3-(2,2-dimethylpropyl)pyrazolo[1,5-a]pyrimidin-2-yl]propanamide;
N-[3-(3-fluoro-4-methylphenyl)-7-methylpyrazolo[1,5-a] pyrimidin-2-yl]-3,3-dimethylbutanamide;
N-[3-(3-fluoro-4-methylphenyl)-7-methylpyrazolo[1,5-a] pyrimidin-2-yl]-2-(4-methoxyphenyl)acetamide;
3-cyclohexyl-N-[3-(2,2-dimethylpropyl)-5,7-dimethylpyrazolo[1,5-a]pyrimidin-2-yl]propanamide;
N-[3-(2,2-dimethylpropyl)-5,7-dimethylpyrazolo[1,5-a]pyrimidin-2-yl]-3-phenylpropanamide;
N-[3-(2,2-dimethylpropyl)-5,7-dimethylpyrazolo[1,5-a]pyrimidin-2-yl]-2-(4-methoxyphenyl)acetamide;
3-cyclohexyl-N-[3-(2,2-dimethylpropyl)-6-methylpyrazolo [1,5-a]pyrimidin-2-yl]propanamide;
N-[3-(2,2-dimethylpropyl)-6-methylpyrazolo[1,5-a]pyrimidin-2-yl]-2-(4-methoxyphenyl)acetamide;
N-[3-(3-fluoro-4-methylphenyl)pyrazolo[1,5-a]pyrimidin-2-yl]-2-phenylacetamide;
3-cyclopentyl-N-[3-(3-fluoro-4-methylphenyl)-6-methylpyrazolo[1,5-a]pyrimidin-2-yl]propanamide;
2-(3,4-dimethoxyphenyl)-N-[3-(3-fluoro-4-methylphenyl)-5,7-dimethylpyrazolo[1,5-a]pyrimidin-2-yl]acetamide;

3,3-dimethyl-N-{3-[3-(trifluoromethoxy)phenyl]pyrazolo [1,5-a]pyrimidin-2-yl}butanamide;
3-cyclopentyl-N-[3-(4-fluorophenyl)pyrazolo[1,5-a]pyrimidin-2-yl]propanamide;
3-cyclohexyl-N-[3-(4-fluorophenyl)pyrazolo[1,5-a]pyrimidin-2-yl]propanamide;
N-[3-(4-fluorophenyl)-6-methylpyrazolo[1,5-a]pyrimidin-2-yl]-2-phenylacetamide;
N-[3-(4-fluorophenyl)-6-methylpyrazolo[1,5-a]pyrimidin-2-yl]-2-(3-methoxyphenyl)acetamide;
2-(4-chlorophenyl)-N-[3-(4-fluorophenyl)-6-methylpyrazolo[1,5-a]pyrimidin-2-yl]acetamide;
2-(4-fluorophenyl)-N-[3-(4-fluorophenyl)-7-methylpyrazolo[1,5-a]pyrimidin-2-yl]acetamide;
N-[3-(4-fluorophenyl)-5,7-dimethylpyrazolo[1,5-a]pyrimidin-2-yl]-3-phenylpropanamide;
N-[3-(4-fluoro-3-methylphenyl)pyrazolo[1,5-a]pyrimidin-2-yl]-3-phenylpropanamide;
N-[3-(4-fluoro-3-methylphenyl)pyrazolo[1,5-a]pyrimidin-2-yl]-2-(4-fluorophenyl)acetamide;
N-[3-(4-fluoro-3-methylphenyl)-5,7-dimethylpyrazolo[1,5-a]pyrimidin-2-yl]-2-(3-methoxyphenyl)acetamide;
N-[3-(4-fluoro-3-methylphenyl)-5,7-dimethylpyrazolo[1,5-a]pyrimidin-2-yl]-3,3-dimethylbutanamide;
2-cyclohexyl-N-[3-(4-fluoro-3-methylphenyl)-5,7-dimethylpyrazolo[1,5-a]pyrimidin-2-yl]acetamide;
3-cyclohexyl-N-[3-(4-fluoro-3-methylphenyl)-6-methylpyrazolo[1,5-a]pyrimidin-2-yl]propanamide;
N-[3-(2,2-dimethylpropyl)-7-methylpyrazolo[1,5-a]pyrimidin-2-yl]-2-(4-methoxyphenyl)acetamide;
3-cyclohexyl-N-[3-(2,2-dimethylpropyl)-7-methylpyrazolo[1,5-a]pyrimidin-2-yl]propanamide;
N-[3-(2,2-dimethylpropyl)-7-methylpyrazolo[1,5-a]pyrimidin-2-yl]-2-(3-methoxyphenyl)acetamide;
N-[3-(4-chlorophenyl)-6-methylpyrazolo[1,5-a]pyrimidin-2-yl]-2-(3,4-dimethoxyphenyl)acetamide;
N-[3-(4-chlorophenyl)-7-methylpyrazolo[1,5-a]pyrimidin-2-yl]-3,3-dimethylbutanamide;
N-[3-(4-chlorophenyl)-7-methylpyrazolo[1,5-a]pyrimidin-2-yl]-2-(3-methoxyphenyl)acetamide;
N-[3-(4-chlorophenyl)-5,7-dimethylpyrazolo[1,5-a]pyrimidin-2-yl]-2-cyclohexylacetamide;
N-[3-(4-chlorophenyl)-5,7-dimethylpyrazolo[1,5-a]pyrimidin-2-yl]-3-cyclopentylpropanamide;
N-[3-(4-chloro-3-methylphenyl)-6-methylpyrazolo[1,5-a]pyrimidin-2-yl]-3-phenylpropanamide;
N-[3-(4-chloro-3-methylphenyl)pyrazolo[1,5-a]pyrimidin-2-yl]-2-(4-fluorophenyl)acetamide;
N-[3-(4-chloro-3-methylphenyl)-7-methylpyrazolo[1,5-a]pyrimidin-2-yl]-3-cyclopentylpropanamide;
N-[3-(4-chloro-3-methylphenyl)-5,7-dimethylpyrazolo[1,5-a]pyrimidin-2-yl]-3-phenylpropanamide;
N-[3-(4-chloro-3-methylphenyl)-5,7-dimethylpyrazolo[1,5-a]pyrimidin-2-yl]-3-cyclohexylpropanamide;
N-[3-(3-chlorophenyl)-7-methylpyrazolo[1,5-a]pyrimidin-2-yl]-3-phenylpropanamide;
N-[3-(3-chlorophenyl)-6-methylpyrazolo[1,5-a]pyrimidin-2-yl]-2-(4-methoxyphenyl)acetamide;
N-[3-(3-chlorophenyl)-6-methylpyrazolo[1,5-a]pyrimidin-2-yl]-3,3-dimethylbutanamide;
N-[3-(3-chlorophenyl)-5,7-dimethylpyrazolo[1,5-a]pyrimidin-2-yl]-2-cyclohexylacetamide;
N-[3-(3-chlorophenyl)-5,7-dimethylpyrazolo[1,5-a]pyrimidin-2-yl]-2-cyclopentylacetamide;
N-[3-(3-chlorophenyl)-5,7-dimethylpyrazolo[1,5-a]pyrimidin-2-yl]-2-(3-methoxyphenyl)acetamide;
N-[3-(3-chlorophenyl)pyrazolo[1,5-a]pyrimidin-2-yl]-2-(2,5-dimethoxyphenyl)acetamide;
N-[3-(3-chlorophenyl)pyrazolo[1,5-a]pyrimidin-2-yl]-3-cyclopentylpropanamide;
N-[3-(3-chlorophenyl)pyrazolo[1,5-a]pyrimidin-2-yl]-2-phenylacetamide;
2-(4-chlorophenyl)-N-[3-(3-chlorophenyl)pyrazolo[1,5-a]pyrimidin-2-yl]acetamide;
N-{6-methyl-3-[4-(trifluoromethyl)phenyl]pyrazolo[1,5-a]pyrimidin-2-yl}-3-phenylpropanamide;
3-cyclopentyl-N-{3-[4-(trifluoromethyl)phenyl]pyrazolo[1,5-a]pyrimidin-2-yl}propanamide;
3-cyclopentyl-N-{5,7-dimethyl-3-[4-(trifluoromethyl)phenyl]pyrazolo[1,5-a]pyrimidin-2-yl}propanamide;
2-(4-chlorophenyl)-N-{5,7-dimethyl-3-[4-(trifluoromethyl)phenyl]pyrazolo[1,5-a]pyrimidin-2-yl}acetamide;
3,3-dimethyl-N-{6-methyl-3-[3-(trifluoromethyl)phenyl]pyrazolo[1,5-a]pyrimidin-2-yl}butanamide;
2-cyclopentyl-N-{3-[3-(trifluoromethyl)phenyl]pyrazolo[1,5-a]pyrimidin-2-yl}acetamide;
3-cyclohexyl-N-{7-methyl-3-[3-(trifluoromethyl)phenyl]pyrazolo[1,5-a]pyrimidin-2-yl}propanamide;
2-(2,5-dimethoxyphenyl)-N-{7-methyl-3-[3-(trifluoromethyl)phenyl]pyrazolo[1,5-a]pyrimidin-2-yl}acetamide;
2-(4-fluorophenyl)-N-{7-methyl-3-[3-(trifluoromethyl)phenyl]pyrazolo[1,5-a]pyrimidin-2-yl}acetamide;
N-[3-(3-chloro-4-methylphenyl)-7-methylpyrazolo[1,5-a]pyrimidin-2-yl]-3-cyclohexylpropanamide;
N-[3-(3-chloro-4-methylphenyl)-7-methylpyrazolo[1,5-a]pyrimidin-2-yl]-2-(4-chlorophenyl)acetamide;
N-[3-(4-fluorobenzyl)pyrazolo[1,5-a]pyrimidin-2-yl]-2-(4-methoxyphenyl)acetamide;
3-cyclopentyl-N-[3-(4-fluorobenzyl)-7-methylpyrazolo[1,5-a]pyrimidin-2-yl]propanamide;
N-[3-(3-chloro-4-methylphenyl)-6-methylpyrazolo[1,5-a]pyrimidin-2-yl]-2-(4-fluorophenyl)acetamide;
N-[3-(3-chloro-4-methylphenyl)-6-methylpyrazolo[1,5-a]pyrimidin-2-yl]-2-(2,5-dimethoxyphenyl)acetamide;
N-[3-(3-chloro-4-methylphenyl)-6-methylpyrazolo[1,5-a]pyrimidin-2-yl]-3-phenylpropanamide;
N-[3-(3-chloro-4-methylphenyl)pyrazolo[1,5-a]pyrimidin-2-yl]-3-cyclopentylpropanamide;
N-[3-(4-fluorobenzyl)-6-methylpyrazolo[1,5-a]pyrimidin-2-yl]-2-(4-methoxyphenyl)acetamide;
3-cyclohexyl-N-[3-(4-fluorobenzyl)-6-methylpyrazolo[1,5-a]pyrimidin-2-yl]propanamide;
N-{5,7-dimethyl-3-[3-(trifluoromethyl)phenyl]pyrazolo[1,5-a]pyrimidin-2-yl}-3-phenylpropanamide;
3-cyclohexyl-N-{7-methyl-3-[4-(trifluoromethyl)phenyl]pyrazolo[1,5-a]pyrimidin-2-yl}propanamide;
2-(4-methoxyphenyl)-N-{7-methyl-3-[4-(trifluoromethyl)phenyl]pyrazolo[1,5-a]pyrimidin-2-yl}acetamide;
2-(4-chlorophenyl)-N-[3-(3-fluorophenyl)pyrazolo[1,5-a]pyrimidin-2-yl]acetamide;
2-(4-fluorophenyl)-N-[3-(3-fluorophenyl)pyrazolo[1,5-a]pyrimidin-2-yl]acetamide;
2-cyclopentyl-N-[3-(3-fluorophenyl)-6-methylpyrazolo[1,5-a]pyrimidin-2-yl]acetamide;
2-(4-fluorophenyl)-N-[3-(3-fluorophenyl)-6-methylpyrazolo[1,5-a]pyrimidin-2-yl]acetamide;
N-[3-(3-fluorophenyl)-5,7-dimethylpyrazolo[1,5-a]pyrimidin-2-yl]-3-phenylpropanamide;
2-cyclohexyl-N-[3-(3-fluorophenyl)-5,7-dimethylpyrazolo[1,5-a]pyrimidin-2-yl]acetamide;
2-cyclopentyl-N-{3-[3-fluoro-4-(trifluoromethyl)phenyl]-6-methylpyrazolo[1,5-a]pyrimidin-2-yl}acetamide;

3-cyclopentyl-N-{3-[3-fluoro-4-(trifluoromethyl)phenyl] pyrazolo[1,5-a]pyrimidin-2-yl}propanamide;
3-cyclohexyl-N-(3-phenylpyrazolo[1,5-a]pyrimidin-2-yl) propanamide;
3-phenyl-N-(3-phenylpyrazolo[1,5-a]pyrimidin-2-yl)propanamide;
N-(7-methyl-3-phenylpyrazolo[1,5-a]pyrimidin-2-yl)-2-phenylacetamide;
3,3-dimethyl-N-(6-methyl-3-phenylpyrazolo[1,5-a]pyrimidin-2-yl)butanamide;
2-(4-chlorophenyl)-N-(6-methyl-3-phenylpyrazolo[1,5-a]pyrimidin-2-yl)acetamide;
2-cyclohexyl-N-(5,7-dimethyl-3-phenylpyrazolo[1,5-a]pyrimidin-2-yl)acetamide;
3-cyclopentyl-N-(5,7-dimethyl-3-phenylpyrazolo[1,5-a]pyrimidin-2-yl)propanamide;
N-(5,7-dimethyl-3-phenylpyrazolo[1,5-a]pyrimidin-2-yl)-2-(4-fluorophenyl)acetamide;
N-[3-(3-fluorophenyl)-7-methylpyrazolo[1,5-a]pyrimidin-2-yl]-2-(4-methoxyphenyl)acetamide;
2-(pyridin-3-yl)-N-{3-[4-(trifluoromethoxy)phenyl]pyrazolo[1,5-a]pyrimidin-2-yl}acetamide;
1-[3-(4-chlorophenyl)pyrazolo[1,5-a]pyrimidin-2-yl]-3-(cyclohexylmethyl)urea;
N-[3-(4-chlorophenyl)pyrazolo[1,5-a]pyrimidin-2-yl]-2-(pyridin-2-yl)acetamide;
N-[3-(4-chlorophenyl)pyrazolo[1,5-a]pyrimidin-2-yl]-2-(pyridin-3-yl)acetamide;
N-[3-(4-chlorophenyl)pyrazolo[1,5-a]pyrimidin-2-yl]-2-(pyridin-4-yl)acetamide;
1-[3-(4-chlorophenyl)pyrazolo[1,5-a]pyrimidin-2-yl]-3-(tetrahydro-2H-pyran-4-ylmethyl)urea;
N-[3-(4-chlorophenyl)pyrazolo[1,5-a]pyrimidin-2-yl]-2-(2-hydroxyphenyl)acetamide;
N-(3-tert-butylpyrazolo[1,5-a]pyrimidin-2-yl)-3-cyclopentylpropanamide;
N-(3-tert-butylpyrazolo[1,5-a]pyrimidin-2-yl)-3,3-dimethylbutanamide;
2-(adamantan-1-yl)-N-(3-tert-butylpyrazolo[1,5-a]pyrimidin-2-yl)acetamide;
1-[3-(4-chlorophenyl)pyrazolo[1,5-a]pyrimidin-2-yl]-3-cyclohexylurea;
N-[3-(4-chlorophenyl)pyrazolo[1,5-a]pyrimidin-2-yl]-2-(3,5-dimethoxyphenyl)acetamide;
3,3-dimethyl-N-[3-(pyridin-3-yl)pyrazolo[1,5-a]pyrimidin-2-yl]butanamide;
N-{3-[(E)-2-(4-chlorophenyl)vinyl]pyrazolo[1,5-a]pyrimidin-2-yl}-3,3-dimethylbutanamide;
3-cyclopentyl-N-(3-isopropylpyrazolo[1,5-a]pyrimidin-2-yl)propanamide;
N-(3-isopropylpyrazolo[1,5-a]pyrimidin-2-yl)-3,3-dimethylbutanamide;
N-[3-(4-chloro-3-methylphenyl)-5,7-dimethylpyrazolo[1,5-a]pyrimidin-2-yl]-3-cyclopropylpropanamide;
3,3-dimethyl-N-{3-[(E)-2-(6-methylpyridin-3-yl)vinyl] pyrazolo[1,5-a]pyrimidin-2-yl}butanamide;
2-(adamantan-1-yl)-N-[3-(2-naphthyl)pyrazolo[1,5-a]pyrimidin-2-yl]acetamide;
N-[3-(4-chlorophenyl)pyrazolo[1,5-a]pyrimidin-2-yl]-3-methyl-3-phenylbutanamide;
3-cyclopropyl-N-(3-isopropylpyrazolo[1,5-a]pyrimidin-2-yl)propanamide;
3-cyclopentyl-N-[3-(pyridin-3-yl)pyrazolo[1,5-a]pyrimidin-2-yl]propanamide;
3-cyclopentyl-N-{3-[4-(trifluoromethoxy)phenyl]pyrazolo[1,5-a]pyrimidin-2-yl}propanamide;
(±)-exo-2-bicyclo[2.2.1]hept-2-yl-N-(3-tert-butylpyrazolo[1,5-a]pyrimidin-2-yl)acetamide;
3-cyclopentyl-N-(3-isopropyl-5,7-dimethylpyrazolo[1,5-a]pyrimidin-2-yl)propanamide;
N-(3-tert-butylpyrazolo[1,5-a]pyrimidin-2-yl)-2-(4-fluorophenyl)acetamide;
(±)-exo-2-bicyclo[2.2.1]hept-2-yl-N-{3-[4-(trifluoromethoxy)phenyl]pyrazolo[1,5-a]pyrimidin-2-yl}acetamide;
methyl 2-[(3-cyclopentylpropanoyl)amino]pyrazolo[1,5-a]pyrimidine-3-carboxylate;
N-(3-tert-butylpyrazolo[1,5-a]pyrimidin-2-yl)-3-methyl-3-phenylbutanamide;
N-(3-tert-butylpyrazolo[1,5-a]pyrimidin-2-yl)-2-(3,5-difluorophenyl)acetamide;
N-[3-(3-fluorophenyl)pyrazolo[1,5-a]pyrimidin-2-yl]-3-methyl-3-phenylbutanamide;
N-(3-tert-butylpyrazolo[1,5-a]pyrimidin-2-yl)-3-phenylpropanamide;
N-(3-tert-butylpyrazolo[1,5-a]pyrimidin-2-yl)-2-cyclohexylacetamide;
(±)-N-(3-tert-butylpyrazolo[1,5-a]pyrimidin-2-yl)-2-(1-methyl-2,3-dihydro-1H-inden-1-yl)acetamide;
N-(3-tert-butylpyrazolo[1,5-a]pyrimidin-2-yl)-3-cyclohexylpropanamide;
2-(cyclopentyloxy)-N-(3-isopropylpyrazolo[1,5-a]pyrimidin-2-yl)acetamide;
N-[3-(4-chloro-3-methylphenyl)-5,7-dimethylpyrazolo[1,5-a]pyrimidin-2-yl]-2-(cyclopentyloxy)acetamide;
3-cyclopentyl-N-[3-(3-fluorophenyl)pyrazolo[1,5-a]pyrimidin-2-yl]propanamide;
(2E)-N-(3-tert-butylpyrazolo[1,5-a]pyrimidin-2-yl)-3-phenylacrylamide;
N-(3-tert-butylpyrazolo[1,5-a]pyrimidin-2-yl)-2-phenylacetamide;
2-(3,5-dimethoxyphenyl)-N-[3-(3-fluorophenyl)pyrazolo[1,5-a]pyrimidin-2-yl]acetamide;
3-cyclopentyl-N-[3-(4-fluoro-3-methylphenyl)-6-methylpyrazolo[1,5-a]pyrimidin-2-yl]propanamide;
2-(4-fluorophenyl)-N-{3-[4-(trifluoromethoxy)phenyl]pyrazolo[1,5-a]pyrimidin-2-yl}acetamide;
3,3-dimethyl-N-[3-(2-methylphenyl)pyrazolo[1,5-a]pyrimidin-2-yl]butanamide;
2-(adamantan-1-yl)-N-{3-[4-(trifluoromethoxy)phenyl] pyrazolo[1,5-a]pyrimidin-2-yl}acetamide;
2-(cyclopentylthio)-N-[3-(4-fluoro-3-methylphenyl)-6-methylpyrazolo[1,5-a]pyrimidin-2-yl]acetamide;
N-{3-[(1E)-3,3-dimethylbut-1-en-1-yl]pyrazolo[1,5-a]pyrimidin-2-yl}-3,3-dimethylbutanamide;
3-cyclopentyl-N-[3-(1-ethylcyclohexyl)pyrazolo[1,5-a]pyrimidin-2-yl]propanamide;
(±)-exo-2-bicyclo[2.2.1]hept-2-yl-N-[3-(1-ethylcyclohexyl)pyrazolo[1,5-a]pyrimidin-2-yl]acetamide;
3,3-dimethyl-N-(3-{(E)-2-[4-(trifluoromethyl)phenyl] vinyl}pyrazolo[1,5-a]pyrimidin-2-yl)butanamide;
tert-butyl {3-[4-(trifluoromethoxy)phenyl]pyrazolo[1,5-a]pyrimidin-2-yl}carbamate;
N-[3-(4-fluoro-3-methylphenyl)-6-methylpyrazolo[1,5-a]pyrimidin-2-yl]-3-methyl-3-phenylbutanamide;
(±)-exo-2-bicyclo[2.2.1]hept-2-yl-N-[3-(4-fluoro-3-methylphenyl)-6-methylpyrazolo[1,5-a]pyrimidin-2-yl]acetamide;
2-(adamantan-1-yl)-N-[3-(4-fluoro-3-methylphenyl)-6-methylpyrazolo[1,5-a]pyrimidin-2-yl]acetamide;
N-(3-tert-butylpyrazolo[1,5-a]pyrimidin-2-yl)-2-(4-chlorophenyl)acetamide;

3-cyclopentyl-N-(3-{(E)-2-[4-(trifluoromethyl)phenyl] vinyl}pyrazolo[1,5-a]pyrimidin-2-yl)propanamide;
N-(3-tert-butylpyrazolo[1,5-a]pyrimidin-2-yl)-2-cyclopentylacetamide;
N-(3-tert-butylpyrazolo[1,5-a]pyrimidin-2-yl)-2-(4-methoxyphenyl)acetamide;
3,3-dimethyl-N-(3-{[4-(trifluoromethoxy)phenyl] ethynyl}pyrazolo[1,5-a]pyrimidin-2-yl)butanamide;
N-[3-(4-chlorophenyl)pyrazolo[1,5-a]pyrimidin-2-yl]-3-cyclohexylpropanamide;
(±)-exo-2-bicyclo[2.2.1]hept-2-yl-N-[3-(4-chlorophenyl) pyrazolo[1,5-a]pyrimidin-2-yl]acetamide;
3-methyl-N-{7-methyl-3-[4-(trifluoromethoxy)phenyl] pyrazolo[1,5-a]pyrimidin-2-yl}-3-phenylbutanamide;
(±)-exo-2-bicyclo[2.2.1]hept-2-yl-N-{7-methyl-3-[4-(trifluoromethoxy)phenyl]pyrazolo[1,5-a]pyrimidin-2-yl}acetamide;
N-{3-[(1E)-3,3-dimethylbut-1-en-1-yl]pyrazolo[1,5-a]pyrimidin-2-yl}-2-(4-fluorophenyl)acetamide;
2-(adamantan-1-yl)-N-[3-(4-chlorophenyl)pyrazolo[1,5-a] pyrimidin-2-yl]acetamide;
N-(3-tert-butylpyrazolo[1,5-a]pyrimidin-2-yl)-2-cyclohexylideneacetamide;
N-[3-(4-fluoro-3-methylphenyl)-6-methylpyrazolo[1,5-a] pyrimidin-2-yl]-4,4-dimethylpentanamide;
N-(3-tert-butylpyrazolo[1,5-a]pyrimidin-2-yl)-3-[4-(trifluoromethyl)phenyl]propanamide;
N-(3-tert-butylpyrazolo[1,5-a]pyrimidin-2-yl)-2-(4-isopropylphenyl)acetamide;
3,3-dimethyl-N-{3-[(1E)-prop-1-en-1-yl]pyrazolo[1,5-a]pyrimidin-2-yl}butanamide;
2-(4-fluorophenyl)-N-{5-methyl-3-[4-(trifluoromethoxy) phenyl]pyrazolo[1,5-a]pyrimidin-2-yl}acetamide;
N-(3-tert-butylpyrazolo[1,5-a]pyrimidin-2-yl)-2-[(cis)-6,6-dichlorobicyclo[3.1.0]hex-2-yl]acetamide;
N-(3-tert-butylpyrazolo[1,5-a]pyrimidin-2-yl)-4,4-dimethylpentanamide;
N-(3-tert-butylpyrazolo[1,5-a]pyrimidin-2-yl)-2-[(1S,2S,5S)-6,6-dimethylbicyclo[3.1.1]hept-2-yl]acetamide;
(±)-N-(3-tert-butylpyrazolo[1,5-a]pyrimidin-2-yl)-2-(2,3-dihydro-1H-inden-1-yl)acetamide;
2-(cyclopentylsulfinyl)-N-[3-(4-fluoro-3-methylphenyl)-6-methylpyrazolo[1,5-a]pyrimidin-2-yl]acetamide;
2-(cyclopentylsulfonyl)-N-[3-(4-fluoro-3-methylphenyl)-6-methylpyrazolo[1,5-a]pyrimidin-2-yl]acetamide;
2-[(cis)-bicyclo[3.1.0]hex-2-yl]-N-(3-tert-butylpyrazolo[1,5-a]pyrimidin-2-yl)acetamide;
(±)-N-[3-(4-fluoro-3-methylphenyl)-6-methylpyrazolo[1,5-a]pyrimidin-2-yl]-2-phenylpropanamide;
tert-butyl {3-[(E)-2-cyclohexylvinyl]pyrazolo[1,5-a]pyrimidin-2-yl}carbamate;
N-(3-tert-butyl-6-methylpyrazolo[1,5-a]pyrimidin-2-yl)-3-cyclohexylpropanamide;
N-(3-tert-butyl-6-methylpyrazolo[1,5-a]pyrimidin-2-yl)-3-cyclopentylpropanamide;
N-(3-tert-butyl-6-methylpyrazolo[1,5-a]pyrimidin-2-yl)-2-cyclohexylacetamide;
2-(4-fluorophenyl)-N-[3-(2-methoxypyrimidin-5-yl)pyrazolo[1,5-a]pyrimidin-2-yl]acetamide;
N-(3-tert-butylpyrazolo[1,5-a]pyrimidin-2-yl)-2-[4-(trifluoromethyl)phenyl]acetamide;
N-(3-tert-butylpyrazolo[1,5-a]pyrimidin-2-yl)-2-(3,4-dichlorophenyl)acetamide;
N-(3-tert-butylpyrazolo[1,5-a]pyrimidin-2-yl)-2-(2,6-dichlorophenyl)acetamide; and
N-[3-(6-chloropyridin-3-yl)pyrazolo[1,5-a]pyrimidin-2-yl]-2-(4-fluorophenyl)acetamide;

or pharmaceutically acceptable salts, solvates, or salts of solvates thereof.

Other compounds contemplated include, but not limited to,
3-(2-{[(4-fluorophenyl)acetyl]amino}pyrazolo[1,5-a]pyrimidin-3-yl)-3-methylbutanoic acid;
3-(2-{[(4-fluorophenyl)acetyl]amino}pyrazolo[1,5-a]pyrimidin-3-yl)-3-methylbutanamide;
3-(2-{[(4-fluorophenyl)acetyl]amino}pyrazolo[1,5-a]pyrimidin-3-yl)-N,3-dimethylbutanamide;
2-(4-fluorophenyl)-N-(3-{2-methyl-4-[(methylsulfonyl) amino]butan-2-yl}pyrazolo[1,5-a]pyrimidin-2-yl)acetamide;
3-(2-{[(4-fluorophenyl)acetyl]amino}pyrazolo[1,5-a]pyrimidin-3-yl)benzoic acid;
3-(2-{[(4-fluorophenyl)acetyl]amino}pyrazolo[1,5-a]pyrimidin-3-yl)-N-methylbenzamide;
[3-(2-{[(4-fluorophenyl)acetyl]amino}pyrazolo[1,5-a]pyrimidin-3-yl)phenyl]acetic acid;
2-[3-(acetylamino)-4-fluorophenyl]-N-{3-[4-(trifluoromethoxy)phenyl]pyrazolo[1,5-a]pyrimidin-2-yl}acetamide;
2-fluoro-N-methyl-5-[2-oxo-2-({3-[4-(trifluoromethoxy) phenyl]pyrazolo[1,5-a]pyrimidin-2-yl}amino)ethyl]benzamide;
2-(4-fluorophenyl)-N-[3-(morpholin-4-yl)pyrazolo[1,5-a] pyrimidin-2-yl]acetamide;
2-(4-fluorophenyl)-N-[3-(tetrahydro-2H-pyran-4-yl)pyrazolo[1,5-a]pyrimidin-2-yl]acetamide; and
2-(4-fluorophenyl)-N-[3-(phenylsulfonyl)pyrazolo[1,5-a] pyrimidin-2-yl]acetamide.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It can be appreciated that two or more asymmetric centers can be present in the present compounds, hence several diastereomers and enantiomers of the exemplified structures can often be possible, and that pure diastereomers and enantiomers represent preferred embodiments. It is intended that pure diastereomers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as Z or E configuration and substituents around a cycloalkyl or a heterocycle are designated as cis or trans configuration.

Within the present application it is to be understood that compounds disclosed herein can exhibit the phenomenon of tautomerism and all tautomeric isomers and mixtures thereof are included in the scope of the invention.

Though structural representations within this specification can show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within drawings or the naming of the compounds.

Compounds described herein can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H), or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J. et al., *Drugs Fut*, 21(11), 1116 (1996); Brickner, S. J. et al., *J Med Chem*, 39(3), 673 (1996); Mallesham, B. et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of KCNQ modulators in binding assays. Isotope-containing compounds have been used in pharmaceutical research to investigate the in vivo metabolic fate of the compounds by evaluation of the mechanism of action and metabolic pathway of the nonisotope-labeled parent compound (Blake et al., *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research, Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radioactive isotope-containing drugs, such as deuterated drugs called "heavy drugs," can be used for the treatment of diseases and conditions related to the activation of KCNQ channels. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D. M. and Finkel A. J., Ann. N.Y. Acad. Sci. 1960 84: 770; Thomson J. F., Ann. New York Acad. Sci., 1960 84: 736; Czakja D. M. et al., Am. J. Physiol., 1961 201: 357). Acute replacement of as high as 15%-23% in human fluids with deuterium was found not to cause toxicity (Blagojevic N. et al. in "Dosimetry & Treatment Planning for Neutron Capture Therapy", Zamenhof R., Solares G., and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions, potentially altering the pharmacokinetic profile or efficacy relative to the non-isotopic compound.

c. Biological Data (i) In Vitro Assay:

The following example describes the assay that can be used to identify compounds that activate KCNQ 2/3 channels.

HEK293 cells stably expressing human KCNQ2 and KCNQ3 subunits were seeded in 96-well, black-walled, clear-bottomed, poly-D-lysine coated plates (BD Biosciences, Bedford, Mass.) at a density of $1 \times 10^5$ cells per well 24 hours before the assay. On the assay day, BTC-AM dye (Invitrogen, Carlsbad, Calif.) was loaded into the cells by replacing the cell culture medium with 100 μL/well of 4 μM dye in DPBS. Dye loading was allowed to proceed for 2 hours at room temperature and then cells were washed twice in 100 μL/well of assay buffer (in mM: 10 HEPES pH 7.3, 5 glucose, 140 Na-gluconate, 2.5 K-gluconate, 3.6 Ca-gluconate, 2 $MgSO_4$, 0.1 Ouabain) to remove unloaded dye. Cells were incubated in 50 μL of assay buffer before loading onto a FLIPR system (Molecular Devices, Sunnyvale, Calif.). Various concentrations of compounds to be assayed were added to the cells in 50 μL of assay buffer and incubated for 4 minutes. The fluorescence signal was initiated by adding 100 μL of assay buffer containing 6 mM $TlNO_3$ and 10 mM $K_2SO_4$. Fluors were excited using the 488-nm line of an argon laser and emission was filtered using a 540±30 nm bandpass filter. Fluorescent signals were recorded for 3 minutes. Responses over baseline values were plotted versus concentrations of test compounds to obtain an $EC_{50}$ value. The maximum response for each test compound was determined relative to the response produced at 10 μM by retigabine. The maximum response of retigabine at 10 μM was set at 100%.

$EC_{50}$ values and the maximum response of compounds described herein assessed by the above-described assays are shown in Table 1 wherein A represents $EC_{50}$ of less than about 100 nM;

B represents $EC_{50}$ between about 100 nM to less than about 500 nM;

C represents $EC_{50}$ between about 500 nM to less than about 1000 nM;

D represents $EC_{50}$ between about 1000 nM to less than about 10,000 nM;

E represents $EC_{50}$ of about and greater than about 10,000 nM.

TABLE 1

| Example # | $EC_{50}$ | Max. % |
|---|---|---|
| 1 | C | 141 |
| 2 | D | 109 |
| 3 | B | 141 |
| 4 | C | 73 |
| 5 | A | 143 |
| 7 | B | 150 |
| 8 | C | 140 |
| 9 | C | 119 |
| 10 | D | 156 |
| 11 | A | 194 |
| 12 | D | 101 |
| 14 | A | 182 |
| 15 | B | 191 |
| 16 | D | 174 |
| 17 | A | 267 |
| 18 | D | 156 |
| 19 | D | 77 |
| 20 | A | 120 |
| 22 | D | 141 |
| 23 | B | 139 |
| 24 | B | 137 |
| 25 | B | 171 |
| 26 | C | 154 |
| 27 | B | 125 |
| 28 | D | 120 |
| 29 | B | 166 |
| 32 | B | 173 |
| 33 | A | 177 |
| 34 | A | 166 |
| 35 | A | 116 |
| 36 | E | 160 |
| 37 | A | 166 |
| 38 | E | 163 |
| 40 | D | 139 |
| 41 | D | 136 |
| 42 | B | 142 |
| 43 | A | 157 |
| 44 | D | 73 |
| 45 | E | 95 |
| 46 | B | 117 |
| 47 | B | 125 |
| 48 | D | 68 |
| 49 | D | 123 |
| 50 | D | 100 |
| 51 | D | 73 |
| 52 | B | 156 |
| 53 | A | 143 |
| 54 | D | 67 |
| 56 | B | 98 |
| 59 | B | 123 |
| 60 | A | 115 |
| 61 | B | 152 |
| 63 | B | 125 |
| 64 | E | 113 |
| 65 | B | 56 |
| 67 | B | 117 |
| 71 | A | 141 |
| 72 | B | 247 |
| 77 | A | 133 |
| 79 | B | 122 |
| 80 | E | 59 |
| 82 | C | 112 |
| 83 | B | 139 |
| 84 | B | 132 |
| 85 | C | 131 |
| 86 | A | 138 |
| 87 | B | 239 |
| 88 | C | 65 |
| 89 | B | 137 |
| 92 | D | 164 |
| 93 | B | 131 |
| 94 | A | 155 |
| 95 | A | 167 |
| 96 | B | 206 |
| 98 | E | 72.3 |
| 99 | D | 94 |
| 100 | E | −1 |
| 101 | E | 8 |
| 102 | E | 23 |
| 103 | E | 8 |
| 104 | E | 10 |
| 105 | B | 153 |
| 106 | D | 67 |
| 107 | B | 94 |
| 108 | E | 8 |
| 109 | E | 8 |
| 110 | E | 8 |
| 111 | E | 59 |
| 112 | C | 135 |
| 113 | B | 18 |
| 114 | B | 119 |
| 115 | E | 10 |
| 116 | C | 98 |
| 117 | E | 64 |
| 118 | E | 14 |
| 119 | D | 52 |
| 120 | B | 114 |
| 121 | A | 150 |
| 122 | A | 155 |
| 123 | B | 142 |
| 124 | B | 130 |
| 125 | E | 8 |
| 126 | B | 133 |
| 127 | B | 147 |
| 128 | D | 96 |
| 129 | B | 160 |
| 130 | B | 131 |
| 131 | D | 97 |
| 132 | A | 142 |
| 133 | E | 7 |
| 134 | E | 11 |
| 135 | B | 143 |
| 136 | E | 8 |
| 137 | D | 195 |
| 138 | E | 11 |
| 139 | A | 100 |
| 140 | E | 66 |
| 141 | E | 6 |
| 142 | D | 152 |
| 143 | B | 162 |
| 144 | B | 174 |
| 145 | B | 182 |
| 146 | C | 151 |
| 147 | D | 65 |
| 148 | E | 20 |
| 149 | C | 127 |
| 150 | A | 198 |
| 151 | A | 179 |
| 152 | B | 191 |
| 153 | E | 50 |
| 154 | D | 188 |
| 155 | D | 116 |
| 156 | D | 40 |
| 157 | A | 99 |
| 158 | B | 143 |
| 159 | C | 136 |
| 160 | A | 148 |
| 161 | B | 107 |
| 162 | C | 128 |
| 163 | D | 133 |
| 164 | C | 126 |
| 165 | B | 178 |
| 166 | C | 154 |
| 167 | D | 98 |
| 168 | B | 78 |
| 169 | B | 134 |
| 170 | D | 124 |
| 171 | A | 138 |
| 172 | E | 20 |
| 173 | E | 21 |

TABLE 1-continued

| Example # | EC$_{50}$ | Max. % |
|---|---|---|
| 174 | E | 67 |
| 175 | D | 177 |
| 176 | B | 83 |
| 177 | D | 51 |
| 178 | A | 158 |
| 179 | A | 151 |
| 180 | B | 155 |
| 181 | E | 7 |

(ii) In Vivo Data:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

Capsaicin-Induced Secondary Mechanical Hypersensitivity:

Rats were allowed to acclimate to the study room for 1 hour. They were then briefly restrained, and capsaicin was administered at 10 µg in 10 µL of vehicle (10% ethanol and 2-hydroxypropyl cyclodextrin) by intraplantar injection into the center of the right hind paw. Secondary mechanical hyperalgesia was measured at the heel away from the site of injection at 180 minutes following capsaicin (Joshi et al., 2006, Neuroscience 143, 587-596). Compounds were injected (i.p.) 30 minutes before testing (150 minutes post-capsaicin).

Tactile (mechanical) allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 seconds with enough force to cause a slight bend in the filament. Positive responses include an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441. Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats. To evaluate the antinociceptive effects, animals were administered vehicle or test compound and tactile allodynia was assessed 30 minutes after i.p. administration.

Tactile allodynia was measured as described above. The compound of Example 1 showed a statistically significant change in paw withdrawal latency versus vehicle at about 30 mg/kg.

Chronic Constriction Injury (CCI) Model of Neuropathic Pain (Bennett Model)

A model of chronic constriction injury-induced (CCI) neuropathic pain was produced by following the method of Bennett and Xie (1988, Pain, 33, 87-107). The right common sciatic nerve was isolated at mid-thigh level, and loosely ligated by 4 chromic gut (5-0) ties separated by an interval of 1 mm. Sham rats can underwent the same procedure, but without sciatic nerve constriction. All animals can be left to recover for at least 2 weeks and no more than 5 weeks prior to testing of mechanical allodynia. Compounds were injected (i.p.) 30 minutes or more before testing. The compounds of Example 1, Example 9, and Example 35 showed a statistically significant change in paw withdrawal latency versus vehicle at about 30 mg/kg.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain, 50, 355) was used to test a compound of the present application The left L5 and L6 spinal nerves of the rat were isolated adjacent to the vertebral column and tightly ligated with a 5-0 silk suture distal to the DRG, and care taken to avoid injury of the L4 spinal nerve. Sham rats underwent the same procedure, but without nerve ligation. All animals were allowed to recover for at least one week and not more than three weeks prior to assessment of tactile allodynia. Compounds were injected (i.p.) 30 minutes or more before testing. The compounds of Example 7 and Example 9 showed a statistically significant change in paw withdrawal latency versus vehicle at about 30 mg/kg.

d. Methods of using the Compounds

In one aspect, the present invention provides methods of using one or more compounds or composition described herein to treat or prevent a disorder, disease, or condition of a subject (including human), which disorder, disease, or condition is responsive to modulation of KCNQ potassium channels. In particular, compounds described herein have utility in the treatment of a disorder, disease, or condition which is responsive to the modulation of KCNQ potassium channels.

In one group of embodiments, diseases and conditions of humans or other animals that can be treated with activation of KCNQ channels, include, but are not limited to, diseases and conditions involving abnormal neuronal excitability such as but not limited to epilepsy, pain, migraine, anxiety, overactive bladder, schizophrenia, anxiety, and substance abuse.

One embodiment provides methods for treating pain (for example, inflammatory pain, osteoarthritic pain, persistent pain, migraine pain, postoperative pain, fibromyalgia, chronic widespread pain, musculoskeletal pain, myofascial pain, temporomandibular joint (TMJ) pain, cancer pain, neuropathic pain, or nociceptive pain) in mammals (including human) in need of such treatment. The methods comprise administering to the mammals therapeutically effective amounts of one or more compounds described herein, or pharmaceutically acceptable salts or solvates thereof. The methods further comprise administration of compounds described herein as a single dose. The methods also comprise repeated or chronic administration of present compounds over a period of days, weeks, months, or longer. In certain embodiments, the method comprises administering to the mammal therapeutically effective amounts of one or more of the compounds described herein, or pharmaceutically acceptable salts or solvates thereof, in combination with one or more analgesics (for example, acetaminophen or opioids such as, but not limited to, morphine), or with one or more nonsteroidal anti-inflammatory drug (NSAID); or administered with a combination of one or more analgesics and one or more NSAID. Examples of NSAIDs include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition can optionally include one or more pharmaceutically acceptable carriers.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level can depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the active ingredients can be required to achieve the desired therapeutic response. "Repeated or chronic administration" refers to the administration of the compositions described herein daily (i.e., every day) or intermittently (i.e., not every day) over a period of days, weeks, months, or longer. In particular, the treatment of chronic painful conditions is anticipated to require such repeated or chronic administration of the compositions described herein. Compounds of the invention can become more effective upon repeated or chronic administration such that the therapeutically effective doses on repeated or chronic administration can be lower than the therapeutically effective dose from a single administration.

Compounds can also be administered as a pharmaceutical composition comprising the compounds of interest in combination with one or more pharmaceutically acceptable carriers. The phrase "therapeutically effective amount" of the compound of the invention means a sufficient amount of the compound to treat disorders or, or to prevent development of or alleviate to some extent one or more of the symptoms of the condition or disorder being treated, at a reasonable benefit/risk ratio applicable to any medical treatment. It can be understood, however, that the total daily usage of the compounds and compositions of the invention can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds can be administered alone, or in combination (i.e. co-administered) with one or more additional pharmaceutical agents. For example, one or more present compounds or pharmaceutically acceptable salts or solvates thereof, can be administered in combination with one or more analgesics (e.g acetaminophen or opioids), or with one or more nonsteroidal anti-inflammatory drug (NSAID), or mixtures thereof. Non limiting examples of suitable NSAIDs include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) can be administered to the patient together, in a single oral dosage composition having a fixed ratio of each active ingredient, such as a tablet or capsule; or each active ingredient can be administered in separate oral dosage formulations.

Separate dosage formulations can be administered at essentially the same time (e.g., concurrently) or at separately staggered times (e.g., sequentially).

Therapeutically effective amounts can be determined by those skilled in the art, and can be adjusted to the requirements of each particular case. Generally, a therapeutically effective amount of a KCNQ modulator can range from a total daily dose, for example in human or other animals, of about 0.01 mg/kg body weight to about 100 mg/kg body weight, preferably of about 0.03 mg/kg body weight to about 30 mg/kg body weight. If desired, the effective daily dose can be divided into multiple doses for purposes of administration. Consequently, single dose compositions can contain such amounts or submultiples thereof to make up the daily dose. It is understood that the effective daily dose can vary with the duration of the treatment.

e. Pharmaceutical Compositions

Pharmaceutical compositions comprising compounds described herein or pharmaceutically acceptable salts or solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts or solvates thereof, and one or more pharmaceutically acceptable carriers, alone or in combination with one or more analgesics (e.g. acetaminophen or opioids), or in combination with one or more nonsteroidal anti-inflammatory drug (NSAID), or a combination of one or more analgesics and one or more NSAID.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound can be mixed under sterile conditions with a pharmaceutically acceptable carrier and any needed preservatives, buffers or propellants which can be required. Opthalmic formulations, eye ointments, powders and solutions are also contemplated as being within the scope of this invention.

Compounds described herein can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. General Synthesis

Compounds described herein when prepared by synthetic processes or by metabolic processes are encompassed in this application. Preparation of the compounds by metabolic processes includes those occurring in the human or animal body (in vivo) or processes occurring in vitro.

Compounds described herein can be prepared using readily available starting materials or known intermediates. The compounds and the intermediates can be prepared by a variety of processes well known for the preparation of compounds of this class. For example, the compounds of formula (I) wherein the groups $G^{1a}$, $G^{2a}$, $R^1$, $R^2$, $R^{2a}$, $R^{2b}$, $R^3$, $R^4$, and $R^5$ have the meanings as set forth in the summary section unless otherwise noted, can be synthesized as provided in Schemes 1-3.

Abbreviations which have been used in the descriptions of the Schemes and the Examples that follow are: DMSO-$d_6$ for deuterated dimethyl sulfoxide, EtOAc for ethyl acetate, $Et_2O$ for diethyl ether, EtOH for ethanol, THF for tetrahydrofuran, and MeOH for methanol.

Compounds of general formula (I) can be prepared, for example, using the general method outlined in Scheme 1.

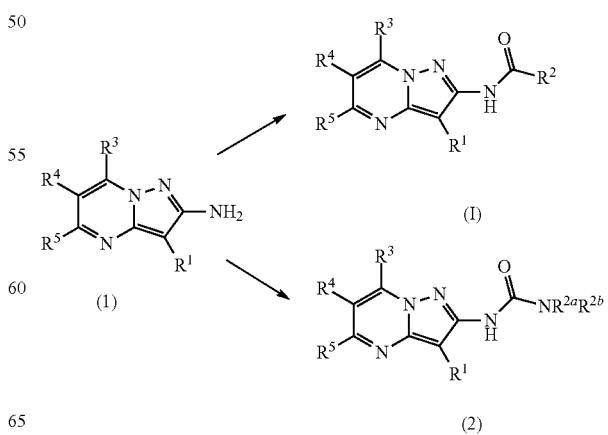

Compounds of formula (1) when treated with compounds of formula $R^2COX^{101}$, wherein $X^{101}$ is chloro, bromo, or OH under coupling conditions known to one skilled in the art, can provide compounds of general formula (I) wherein $R^2$ is unsubstituted or substituted alkyl, haloalkyl, unsubstituted or substituted alkenyl, unsubstituted or substituted alkynyl, or $G^{2a}$. Typical conditions for the reaction of (1) with compounds of formula $R^2COX^{101}$, wherein $X^{101}$ is chloro or bromo include, but are not limited to, stirring about an equimolar mixture of the compounds in a solvent such as, but not limited to, chloroform, dichloromethane, THF, or mixture thereof, optionally in the presence of a base such as, but not limited to, diisopropylethylamine or pyridine, at about 0° C. to about 30° C. for about 8-24 hours. Acid coupling conditions for compounds of formula $R^2COX^{101}$ wherein $X^{101}$ is —OH and compounds of formula (2), include stirring about an equimolar mixture of the compounds in a solvent such as, but not limited to, THF, N,N-dimethylacetamide, N,N-dimethylformamide, pyridine, chloroform, or mixtures thereof, with a coupling reagent, optionally along with a coupling auxiliary, and in the presence or absence of a base. Typical reactions can be carried out at temperatures ranging from about 0° C. to about 65° C. or can be carried out in a microwave reactor to facilitate the coupling. Examples of coupling reagents include, but are not limited to, bis(2-oxo-3-oxazolidinyl)phosphinic chloride (BOPCl), 1-(3-dimethylaminopropyl)-3-ethylcarbodiimide hydrochloride (EDCI or EDC), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 1-propanephosphonic acid cyclic anhydride. Non limiting examples of a coupling auxiliary include 1-hydroxy-7-azabenzotriazole (HOAT) and 1-hydroxybenzotriazole hydrate (HOBT). Suitable examples of bases include, but are not limited to, N-methylmorpholine and diisopropylethylamine Conversion of (1) to (2) can be accomplished by treating (1) with an appropriate isocyanate in the presence of a base, such as, but not limited to, pyridine, at about room temperature to about 80° C.

Alternatively, compounds of general formula (I) wherein $R^1$ is $G^{1a}$, unsubstituted or substituted alkyl, unsubstituted or substituted alkenyl, or unsubstituted or substituted alkynyl, can be prepared using general procedure as outlined in Scheme 2.

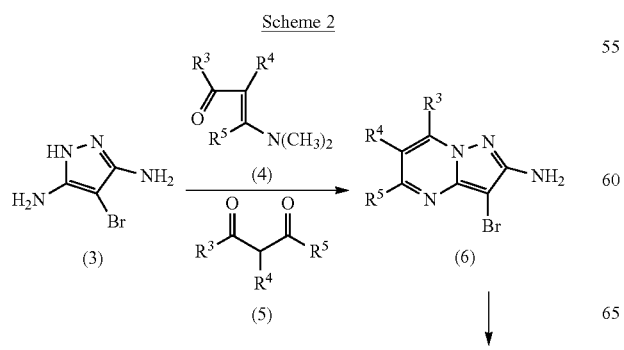

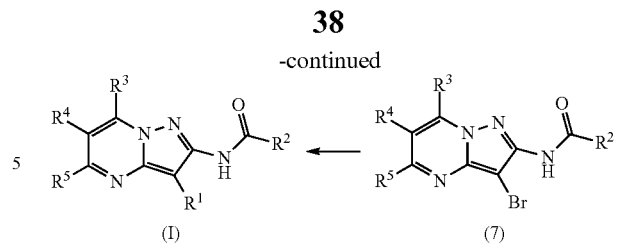

Compound of formula (3) can be treated with (4) or diketones of formula (5) in the presence of catalytic amount of acetic acid and irradiation of microwave, to provide intermediates of formula (6).

Compounds of formula (6) can be transformed to compounds of formula (7) using reaction conditions as outlined in Scheme 1. Compounds of formula (I) can be prepared from (7) by treatment with the appropriate boronic acid or esters when $R^1$ is unsubstituted or substituted alkyl, unsubstituted or substituted alkenyl, or $G^{1a}$, or with an appropriate unsubstituted or substituted alkyne, in the presence of a palladium catalyst such as, but not limited to, dichlorobis(triphenylphosphine)palladium (II) and bis(tri-t-butylphosphino) palladium, and a base such as, but not limited to, sodium carbonate, cesium fluoride, triethylamine, in a solvent such as, but not limited to, dioxane, tetrahydrofuran, toluene, 2-propanol, and N,N-dimethylformamide, or mixtures thereof; and in the absence or presence of CuI, and at temperatures from about 50° C. to about 100° C. Elevated temperatures or microwave irradiation can be beneficial to the reactions.

Intermediates of general formula (1) can be prepared as shown in Scheme 3.

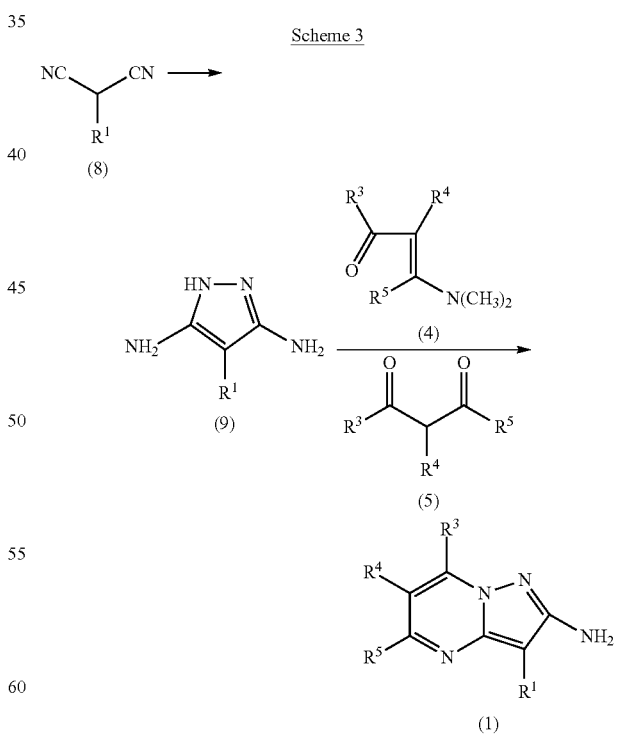

Compounds of formula (8) can be prepared by treating malonitrile with an appropriate halide of formula $R^1X^{102}$ wherein $X^{102}$ is Cl, Br, or I, and $R^1$ is unsubstituted or substituted alkyl or $G^{1a}$, in the presence of sodium hydride and in the presence of a palladium reagent such as, but not limited to, bis(triphenylphosphine)palladium (II) chloride, and in a solvent such as, THF, at elevated temperature, for example, at about the reflux temperature of the solvent employed. The resulting diamine can be converted to intermediates (1) using reaction conditions for the transformation of (3) to (6) in Scheme 2.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

Following Examples can be used for illustrative purposes and should not be deemed to narrow the scope of the invention.

All experiments were conducted at room temperature unless otherwise stated.

g. Examples

Example 1

3,3-dimethyl-N-(3-(4-(trifluoromethoxy)phenyl) pyrazolo[1,5-a]pyrimidin-2-yl)butanamide Example 1A 2-(4-(trifluoromethoxy)phenyl)malononitrile To a suspension of sodium hydride (2.87 g, 114 mmol) in THF (15 mL), malononitrile (4.77 mL, 76 mmol) in 2 mL of THF was added dropwise at 0° C. After the gas evolution ceased, 1-iodo-4-(trifluoromethoxy)benzene (5.92 mL, 37.8 mmol) and bis(triphenylphosphine)palladium(II) chloride (0.797 g, 1.135 mmol) were added. This mixture was then heated at reflux under nitrogen overnight. The suspension was cooled to ambient temperature, treated with water, acidified with 1N HCl and extracted with ethyl acetate. The combined organic layers were washed with brine, dried over magnesium sulfate and filtered. The filtrate was concentrated and purified on silica gel (0~30% ethyl acetate in hexanes) to give 8.2 g of product as a tan solid. $^1$H NMR (400 MHz, CDCl$_3$) δ ppm 7.48-7.65 (m, 2H) 7.37 (d, J=8.35 Hz, 2H) 5.09 (s, 1H). MS (ESI) m/z 225.1 (M–H)$^-$.

Example 1B 4-(4-(trifluoromethoxy)phenyl)-1H-pyrazole-3,5-diamine

A solution of the product from Example 1A (130 mg, 0.575 mmol) and hydrazine monohydrate (0.141 mL, 2.87 mmol) in butan-1-ol (2.0 mL) was irradiated with microwave (Biotage Initiator Microwave Synthesizer) at 125° C. for 15 minutes. The reaction mixture was cooled to ambient temperature and diluted with water. The aqueous phase was then extracted with dichloromethane. Organic layer was washed with brine and concentrated to give 0.1 g of the title compound as a white solid. $^1$H NMR (400 MHz, DMSO-d$_6$) δ ppm 10.37 (s, 1H) 7.41-7.64 (m, 2H) 7.28 (d, J=8.13 Hz, 2H) 4.58 (s, 4H). MS (ESI) m/z 259.3 (M+H)$^+$.

Example 1C 3-(4-(trifluoromethoxy)phenyl)pyrazolo[1,5-a]pyrimidin-2-amine

In a microwave vessel containing the product from Example 1B (0.4 g, 1.549 mmol) and 3-(dimethylamino) acrylaldehyde (0.155 g, 1.549 mmol) in ethanol (5 mL) was added two drops of acetic acid. The mixture was irradiated with microwave at 140° C. for 15 minutes and concentrated. The resulting solid was purified by flash chromatography on silica gel, eluting with EtOAc/Hexanes (40-70% gradient), to yield the title compound (0.49 g, 59%). MS ESI$^+$ m/z 295.5 [M+H]$^+$.

Example 1D 3,3-dimethyl-N-(3-(4-(trifluoromethoxy)phenyl)pyrazolo[1,5-a]pyrimidin-2-yl)butanamide To a solution of the product from Example 1C (0.318 g, 1.081 mmol) in dichloromethane (8 mL) was added pyridine (0.256 g, 3.24 mmol). 3,3-Dimethylbutanoyl chloride (0.160 g, 1.189 mmol) was slowly added and the resulting reaction mixture was stirred at room temperature for 3 hours. The reaction mixture was concentrated and the residue was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-6.0 min linear gradient 10-100% A, 6.0-7.0 min 100% A, 7.0-8.0 min linear gradient 100-10% A) to yield the title compound (0.38 g, 88%). $^1$H NMR (400 MHz, CD$_3$Cl) δ ppm 1.11 (s, 6H) 2.33 (s, 2H) 6.86 (dd, J=6.94, 4.12 Hz, 1H) 7.30-7.42 (m, 3H) 7.63-7.79 (m, 2H) 8.51 (dd, J=4.12, 1.73 Hz, 1H) 8.68 (dd, J=6.94, 1.63 Hz, 1H). MS ESI(+) m/z 393.4 [M+H]$^+$.

Example 2

N-[3-(4-fluorophenyl)pyrazolo[1,5-a]pyrimidin-2-yl]-3,3-dimethylbutanamide

The title compound was prepared using the methods analogous to that described in Examples 1A-1D, substituting 1-fluoro-4-iodobenzene for 1-iodo-4-(trifluoromethoxy)benzene. $^1$H NMR (400 MHz, CD$_3$Cl) δ ppm 1.11 (s, 9H) 2.32 (s, 2H) 6.83 (dd, J=6.99, 4.07 Hz, 1H) 7.15-7.23 (m, 2H) 7.37 (s, 1H) 7.55-7.71 (m, 2H) 8.48 (dd, J=4.01, 1.63 Hz, 1H) 8.63-8.73 (m, 1H). MS ESI(+) m/z 327.5 [M+H]$^+$.

Example 3

3,3-dimethyl-N-{6-methyl-3-[3-(trifluoromethoxy)phenyl]pyrazolo[1,5-a]pyrimidin-2-yl}butanamide The title compound was prepared using the methods analogous to that described in Examples 1A-1D, substituting 1-iodo-3-(trifluoromethoxy)benzene for 1-iodo-4-(trifluoromethoxy)benzene and 3-(dimethylamino)-2-methylacrylaldehyde for 3-(dimethylamino)acrylaldehyde. $^1$H NMR (400 MHz, DMSO-d$_6$) δ ppm 1.02 (s, 9H) 2.36 (s, 3H) 4.45 (s, 2H) 7.16-7.33 (m, 1H) 7.54 (t, J=8.08 Hz, 1H) 7.76 (s, 1H) 7.88 (d, J=7.92 Hz, 1H) 8.58 (d, J=2.17 Hz, 1H) 8.98 (dd, J=1.84, 1.08 Hz, 1H) 10.13 (s, 1H); MS (ESI) m/z 407.2 (M+H)$^+$.

Example 4

2-[(1S,2S,5S)-6,6-dimethylbicyclo[3.1.1]hept-2-yl]-N-{3-[4-(trifluoromethoxy)phenyl]pyrazolo[1,5-a]pyrimidin-2-yl}acetamide

Example 4A 2-((1S,2S,5S)-6,6-dimethylbicyclo[3.1.1]heptan-2-yl)ethanol (−)-Nopol (Aldrich) (66.4 g, 0.40 mmol) was dissolved in ethyl acetate (500 mL). PtO$_2$ (2.0 g) was added under N$_2$ atmosphere. The mixture was hydrogenated at 41 psi. Uptake was completed within 2.5 hours. The mixture was filtered, washed with ethyl acetate and concentrated. The residue was distilled at 125-130° C./9.5 mm of Hg to afford 61.5 g of the title compound.

Example 4B 2-((1S,2S,5S)-6,6-dimethylbicyclo[3.1.1]heptan-2-yl)acetic acid

A solution of chromium trioxide (42.6 g CrO$_3$, 426 mmol) in water (40 mL) was diluted with acetic acid (350 mL). The solution was cooled to 15° C. and the product from Example 4A (27 g, 160 mmol) was added dropwise. The solution was left to stand at room temperature overnight. Ethanol (20 mL) was added to destroy the excess of CrO$_3$. The mixture was heated at 50° C. for 15 minutes and then concentrated under reduced pressure. The residue was suspended in water, acidified to pH 2 and extracted 3 times with ether. The ethereal solution was concentrated and the residue was dissolved in hexanes. The organic solution is decanted from the green tar and concentrated under reduced pressure. The residue was dissolved in 10% aqueous NaOH and neutral impurities were extracted with ether (discarded). The aqueous phase was acidified to pH 2 and extracted with hexanes, dried with Na$_2$SO$_4$, concentrated, cooled and filtered to give 10.9 g of title compound (crystals melting point: 50-53° C.).

Example 4C 2-((1S,2S,5S)-6,6-dimethylbicyclo[3.1.1]heptan-2-yl)acetyl chloride To a mixture of the product from Example 4B (300 mg, 1.65 mmol) and thionyl chloride (901 μL, 12.4 mmol) was added a drop of dimethylformamide. The reaction was stirred at 22° C. for 2 hours. The excess of thionyl chloride was evaporated and the residue was dried under vacuum to afford the title compound.

Example 4D

2-[(1S,2S,5S)-6,6-dimethylbicyclo[3.1.1]hept-2-yl]-N-{3-[4-(trifluoromethoxy)phenyl]pyrazolo[1,5-a]pyrimidin-2-yl}acetamide The title compound was prepared using the method analogous to that described in Examples 1D, substituting the product from Example 4C for 3,3-dimethylbutanoyl chloride. $^1$H NMR (400 MHz, CD$_3$Cl) δ ppm 0.91-1.08 (m, 4H) 1.14-1.23 (m, 3H) 1.42-1.58 (m, 1H) 1.78-2.00 (m, 4H) 2.01-2.19 (m, 1H) 2.02-2.19 (m, 1H) 2.29-2.43 (m, 1H) 2.46-2.76 (m, 3H) 6.87 (dd, J=6.94, 4.12 Hz, 1H) 7.34 (d, J=8.24 Hz, 2H) 7.39 (s, 1H) 7.72 (d, J=8.67 Hz, 2H) 8.51 (dd, J=4.01, 1.73 Hz, 1H) 8.65 (dd, J=6.99, 1.46 Hz, 1H). MS ESI($^+$) m/z 459.5 [M+H]$^+$.

Example 5

2-cyclopentyl-N-(3-(4-fluorobenzyl)-6-methylpyrazolo[1,5-a]pyrimidin-2-yl)acetamide

Example 5A 2-(4-fluorobenzyl)malononitrile

To a solution of malononitrile (3.15 mL, 50.0 mmol) in 50 mL of 95% EtOH, 4-fluorobenzaldehyde (5.28 mL, 50 mmol)

was added and the mixture was stirred at room temperature overnight. The white solid precipitated out and this suspension was diluted with 25 mL of EtOH then treated with sodium borohydride (0.946 g, 25.00 mmol) in one portion. This mixture was stirred at ambient temperature for 2 hours until reaction was complete. Water and 1N HCl solution was added carefully to quench sodium borohydride. The precipitate was then filtered, washed with copious amount of water, air-dried to give 5.92 g of the title compound as a white solid. $^1$H NMR (400 MHz, CDCl$_3$) δ ppm 7.28-7.43 (m, 2H) 7.06-7.17 (m, 2H) 3.90 (t, J=6.78 Hz, 1H) 3.27 (d, J=6.72 Hz, 2H). MS (ESI) m/z 173.1 (M−H)$^-$.

Example 5B 4-(4-fluorobenzyl)-1H-pyrazole-3,5-diamine

The product from Example 5A (1.5 g, 8.61 mmol) and hydrazine monohydrate (2.111 mL, 43.1 mmol) was processed using the method analogous to that described in Example 1B to afford the title compound. $^1$H NMR (400 MHz, DMSO-d$_6$) δ ppm 9.96 (s, 1H) 7.15-7.51 (m, 2H) 6.79-7.11 (m, 2H) 4.30 (s, 4H) 3.48 (s, 2H). MS (ESI) m/z 259.3 (M+H)$^+$.

Example 5C 3-(4-fluorobenzyl)-6-methylpyrazolo[1,5-a]pyrimidin-2-amine

The product from Example 5B (0.4 g, 1.940 mmol) was processed using the method analogous to that described in Example 1C, substituting 3-(dimethylamino)-2-methylacrylaldehyde (0.219 g, 1.940 mmol) for 3-(dimethylamino)acrylaldehyde to afford the title compound. $^1$H NMR (400 MHz, DMSO-d$_6$) δ ppm 8.49 (d, J=0.87 Hz, 1H) 8.11 (d, J=2.06 Hz, 1H) 7.20-7.43 (m, 2H) 6.91-7.17 (m, 2H) 5.52 (s, 2H) 3.88 (s, 2H) 2.20 (s, 3H). MS (ESI) m/z 257.1 (M+H)$^+$.

Example 5D 2-cyclopentyl-N-(3-(4-fluorobenzyl)-6-methylpyrazolo[1,5-a]pyrimidin-2-yl)acetamide The product from Example 5C (0.15 g, 0.585 mmol) was processed using the method analogous to that described in Example 1D, substituting 2-cyclopentylacetyl chloride (0.095 mL, 0.702 mmol) for 3,3-dimethylbutanoyl chloride to afford the title compound. $^1$H NMR (400 MHz, DMSO-d$_6$) δ ppm 10.05 (s, 1H) 8.81 (s, 1H) 8.39 (d, J=1.95 Hz, 1H) 7.09-7.31 (m, 2H) 6.91-7.07 (m, 2H) 4.04 (s, 2H) 2.30 (s, 3H) 2.23-2.28 (m, 2H) 2.07-2.22 (m, 1H) 1.37-1.84 (m, 6H) 1.12 (d, J=7.05 Hz, 2H). MS (ESI) m/z 367.2 (M+H)$^+$.

Example 6

N-[3-(4-chlorophenyl)pyrazolo[1,5-a]pyrimidin-2-yl]-2-phenylacetamide

The title compound was prepared using the methods analogous to that described in Examples 1A-1D, substituting 1-chloro-4-iodobenzene for 1-iodo-4-(trifluoromethoxy)benzene and 2-phenylacetyl chloride for 3,3-dimethylbutanoyl chloride. $^1$H NMR (500 MHz, DMSO-d$_6$/D$_2$O) δ ppm 9.04 (dd, J=6.9, 1.7, 1H), 8.63 (dd, J=4.1, 1.7, 1H), 7.70-7.64 (m, 2H), 7.39-7.28 (m, 6H), 7.14 (dd, J=7.0, 4.1, 1H), 3.68 (s, 2H). MS ESI(+) m/z 363.1 [M+H]$^+$.

Example 7

N-[3-(4-chlorophenyl)pyrazolo[1,5-a]pyrimidin-2-yl]-3-cyclopentylpropanamide

The title compound was prepared using the methods analogous to that described in Examples 1A-1D, substituting 1-chloro-4-iodobenzene for 1-iodo-4-(trifluoromethoxy)benzene and 3-cyclopentylpropanoyl chloride for 3,3-dimethylbutanoyl chloride. $^1$H NMR (500 MHz, DMSO-d$_6$/D$_2$O) δ ppm 9.04 (dd, J=6.9, 1.7, 1H), 8.63 (dd, J=4.1, 1.7, 1H), 7.81-7.75 (m, 2H), 7.50-7.45 (m, 2H), 7.14 (dd, J=6.9, 4.1, 1H), 2.35 (m, 2H), 1.72 (m, 4H), 1.58 (m, 4H), 1.48 (m, 1H), 1.07 (m, 2H). MS ESI(+) m/z 369.1 [M+H]$^+$.

Example 8

2-(3-methoxyphenyl)-N-{6-methyl-3-[4-(trifluoromethoxy)phenyl]pyrazolo[1,5-a]pyrimidin-2-yl}acetamide The title compound was prepared using the methods analogous to that described in Examples 1A-1D, substituting 3-(dimethylamino)-2-methylacrylaldehyde for 3-(dimethylamino)acrylaldehyde, and 2-(3-methoxyphenyl)acetyl chloride for 3,3-dimethylbutanoyl chloride. $^1$H NMR (500 MHz, DMSO-d$_6$/Deuterium Oxide) δ ppm 8.89-8.90 (m, 1H), 8.54 (d, J=2.1 Hz, 1H), 7.73-7.75 (m, 2H), 7.25-7.32 (m, 1H), 7.18-7.25 (m, 2H), 6.90-6.98 (m, 2H), 6.85-6.90 (m, 1H), 3.74 (s, 3H), 3.63-3.64 (bs, 2H), 2.36 (s, 3H); MS (ESI) m/z 457.2 (M+H)$^+$.

Example 9

2-(4-fluorophenyl)-N-{7-methyl-3-[4-(trifluoromethoxy)phenyl]pyrazolo[1,5-a]pyrimidin-2-yl}acetamide The title compound was prepared using the methods analogous to that described in Examples 1A-1D, substituting 4-(dimethylamino)but-3-en-2-one for 3-(dimethylamino)acrylaldehyde, and substituting 2-(4-fluorophenyl)acetyl chloride for 3,3-dimethylbutanoyl chloride. $^1$H NMR (400 MHz, DMSO-d$_6$) δ ppm 10.54-10.66 (bs, 1H), 8.54 (d, J=4.2 Hz, 1H), 7.74-7.77 (m, 2H), 7.32-7.40 (m, 2H), 7.21-7.27 (m, 2H), 7.14-7.20 (m, 2H), 7.12 (dd, J=4.3, 0.8 Hz, 1H), 3.67 (s, 2H), 2.73 (s, 3H); MS (ESI) m/z 445.1 (M+H)$^+$.

Example 10

N-[3-(2,2-dimethylpropyl)pyrazolo[1,5-a]pyrimidin-2-yl]-3-phenylpropanamide

Example 10A 2-(2,2-dimethylpropylidene)malononitrile

To a 500 mL round bottom flask were added malononitrile and 100 mL 2-propanol. The mixture was bubbled with nitrogen. Trimethylacetaldehyde was added, followed by titanium (IV) isopropoxide. The clear yellow solution was stirred at room temperature overnight. The creamy reaction mixture was poured into 100 mL 1N HCl solution cooled in ice water bath. The mixture was stirred for 30 minutes and then extracted with ethyl acetate twice. The combined organic layers were washed with saturated sodium bicarbonate solution, brine, dried ($Na_2SO_4$), filtered, and concentrated in vacuo. The crude product was loaded to a 340 g Biotage Si column for purification (0-25% ethyl acetate in hexanes) to give the title compound as a white solid (16.7 g, yield 70%). $^1$H NMR (400 MHz, DMSO-$d_6$) δ 7.82 (s, 1H), 1.23 (s, 9H).

Example 10B 2-neopentylmalononitrile

To the 500 mL round bottom flask with the product from Example 10A was added 100 mL ethanol. The mixture was cooled in an ice bath (NaCl was added to the bath to keep the temperature below 0° C.) and sodium borohydride was added. The mixture was stirred for 30 minutes. 160 mL 0.5 N HCl solution was added carefully and ethyl acetate was used to extract the mixture twice. Brine was added to help the layers to separate. The combined organic layers were washed with brine, dried ($Na_2SO_4$), filtered, and concentrated in vacuo. The crude title compound was used directly in the following steps without further purification. MS (ESI) m/z 135.1 (M−H)$^-$.

Example 10C

N-[3-(2,2-dimethylpropyl)pyrazolo[1,5-a]pyrimidin-2-yl]-3-phenylpropanamide

The title compound was prepared using the methods analogous to that described in Examples 1B-1D, substituting the product from Example 10B for the product from Example 1A, and substituting 3-phenylpropanoyl chloride for 3,3-dimethylbutanoyl chloride. $^1$H NMR (400 MHz, DMSO-$d_6$/Deuterium Oxide) δ ppm 8.88 (dd, J=6.9, 1.7 Hz, 1H), 8.46 (dd, J=4.0, 1.7 Hz, 1H), 7.26-7.33 (m, 4H), 7.18-7.23 (m, 1H), 6.96 (dd, J=6.9, 4.0 Hz, 1H), 2.93 (t, J=7.5 Hz, 2H), 2.69 (t, J=7.5 Hz, 2H), 2.60 (s, 2H), 0.78 (s, 9H); MS (ESI) m/z 337.2 (M+H)$^+$.

Example 11

3-cyclohexyl-N-[3-(2,2-dimethylpropyl)pyrazolo[1,5-a]pyrimidin-2-yl]propanamide

The title compound was prepared using the methods analogous to that described in Examples 1B-1D, substituting the product from Example 10B for the product from Example 1A, and substituting 3-cyclohexylpropanoyl chloride for 3,3-dimethylbutanoyl chloride. $^1$H NMR (400 MHz, DMSO-$d_6$/Deuterium Oxide) δ ppm 8.88 (dd, J=6.9, 1.7 Hz, 1H), 8.46 (dd, J=4.0, 1.7 Hz, 1H), 6.96 (dd, J=6.9, 4.0 Hz, 1H), 2.63 (s, 2H), 2.36 (t, J=7.4 Hz, 2H), 1.59-1.75 (m, 5H), 1.51 (q, J=7.2 Hz, 2H), 1.11-1.28 (m, 4H), 0.90-0.91 (m, 2H), 0.84 (s, 9H); MS (ESI) m/z 343.2 (M+H)$^+$.

Example 12

N-[3-(3-fluoro-4-methylphenyl)-7-methylpyrazolo[1,5-a]pyrimidin-2-yl]-3,3-dimethylbutanamide The title compound was prepared using the methods analogous to that described in Examples 1A-1D, substituting 2-fluoro-4-iodo-1-methylbenzene for 1-iodo-4-(trifluoromethoxy)benzene, and substituting 4-(dimethylamino)but-3-en-2-one for 3-(dimethylamino)acrylaldehyde. $^1$H NMR (500 MHz, DMSO-$d_6$/Deuterium Oxide) δ ppm 8.53 (d, J=4.2 Hz, 1H), 7.52-7.58 (m, 2H), 7.31 (dd, J=8.3 Hz, 1H), 7.09 (dd, J=4.2, 1.1 Hz, 1H), 2.72 (s, 3H), 2.24-2.27 (m, 5H), 1.03 (s, 9H); MS (ESI) m/z 355.1 (M+H)$^+$.

Example 13

N-[3-(3-fluoro-4-methylphenyl)-7-methylpyrazolo[1,5-a]pyrimidin-2-yl]-2-(4-methoxyphenyl)acetamide The title compound was prepared using the methods analogous to that described in Examples 1A-1D, substituting 2-fluoro-4-iodo-1-methylbenzene for 1-iodo-4-(trifluoromethoxy)benzene, 4-(dimethylamino)but-3-en-2-one for 3-(dimethylamino)acrylaldehyde, and 2-(4-methoxyphenyl)acetyl chloride for 3,3-dimethylbutanoyl chloride. $^1$H NMR (500 MHz, DMSO-$d_6$/Deuterium Oxide) δ ppm 8.53 (d, J=4.3 Hz, 1H), 7.49 (dd, J=11.6, 1.7 Hz, 1H), 7.40 (d, J=7.8 Hz, 1H), 7.21-7.31 (m, 2H), 7.13-7.20 (m, 1H), 7.09 (dd, J=4.3, 0.9 Hz, 1H), 6.91 (d, J=7.3 Hz, 1H), 3.75-3.76 (m, 4H), 3.60-3.61 (bs, 2H), 2.72 (s, 3H), 2.23 (s, 3H); MS (ESI) m/z 405.1 (M+H)$^+$.

Example 14

3-cyclohexyl-N-[3-(2,2-dimethylpropyl)-5,7-dimethylpyrazolo[1,5-a]pyrimidin-2-yl]propanamide The title compound was prepared using the methods analogous to that described in Examples 1B-1D, substituting the product from Example 10B for the product from Example 1A, acetylacetone for 3-(dimethylamino)acrylaldehyde, and 3-cyclohexylpropanoyl chloride for 3,3-dimethylbutanoyl chloride. $^1$H NMR (400 MHz, DMSO-$d_6$/Deuterium Oxide) δ ppm 6.79 (d, J=1.0 Hz, 2H), 2.60 (d, J=0.8 Hz, 2H), 2.57-2.59 (m, 2H), 2.46-2.48 (bs, 3H), 2.31-2.38 (m, 2H), 1.61-1.77 (m, 4H), 1.50 (q, J=7.2 Hz, 2H), 1.11-1.30 (m, 4H), 0.85-0.96 (m, 3H), 0.83 (s, 9H); MS (ESI) m/z 371.3 (M+H)$^+$.

Example 15

N-[3-(2,2-dimethylpropyl)-5,7-dimethylpyrazolo[1,5-a]pyrimidin-2-yl]-3-phenylpropanamide The title compound was prepared using the methods analogous to that described in Examples 1B-1D, substituting the product from Example 10B for the product from Example 1A, acetylacetone for 3-(dimethylamino)acrylaldehyde, and 3-phenylpropanoyl chloride for 3,3-dimethylbutanoyl chloride. $^1$H NMR (400 MHz, DMSO-$d_6$/Deuterium Oxide) δ ppm 7.26-7.33 (m, 5H), 7.18-7.24 (m, 1H), 6.79 (d, J=1.1 Hz, 1H), 2.92 (t, J=7.6 Hz, 2H), 2.67 (t, J=7.6 Hz, 2H), 2.60 (d, J=0.9 Hz, 3H), 2.55-2.56 (bs, 2H), 2.47 (s, 3H), 0.76-0.79 (bs, 9H); MS (ESI) m/z 365.2 (M+H)$^+$.

Example 16

N-[3-(2,2-dimethylpropyl)-5,7-dimethylpyrazolo[1,5-a]pyrimidin-2-yl]-2-(4-methoxyphenyl)acetamide The title compound was prepared using the methods analogous to that described in Examples 1B-1D, substituting the product from Example 10B for the product from Example 1A, acetylacetone for 3-(dimethylamino)acrylaldehyde, and 2-(4-methoxyphenyl)acetyl chloride for 3,3-dimethylbutanoyl chloride. $^1$H NMR (400 MHz, DMSO-$d_6$/Deuterium Oxide) δ ppm 7.26-7.32 (m, 2H), 6.88-6.94 (m, 2H), 6.79 (d, J=1.1 Hz, 1H), 3.74 (s, 3H), 3.56-3.60 (bs, 2H), 2.60 (d, J=0.6 Hz, 3H), 2.49-2.51 (bs, 2H), 2.46-2.47 (bs, 3H), 0.71-0.75 (bs, 9H); MS (ESI) m/z 381.2 (M+H)$^+$.

Example 17

3-cyclohexyl-N-[3-(2,2-dimethylpropyl)-6-methylpyrazolo[1,5-a]pyrimidin-2-yl]propanamide The title compound was prepared using the methods analogous to that described in Examples 1B-1D, substituting the product from Example 10B for the product from Example 1A, 3-(dimethylamino)-2-methylacrylaldehyde for 3-(dimethylamino)acrylaldehyde, and 3-cyclohexylpropanoyl chloride for 3,3-dimethylbutanoyl chloride. $^1$H NMR (400 MHz, DMSO-d$_6$/Deuterium Oxide) δ ppm 8.72 (dd, J=2.1, 1.3 Hz, 1H), 8.36 (d, J=2.3 Hz, 1H), 2.32-2.37 (m, 3H), 2.30 (d, J=0.9 Hz, 3H), 1.58-1.76 (m, 6H), 1.50 (q, J=7.5 Hz, 2H), 1.07-1.31 (m, 5H), 0.85-0.95 (m, 1H), 0.83 (s, 9H); MS (ESI) m/z 357.2 (M+H)$^+$.

Example 18

N-[3-(2,2-dimethylpropyl)-6-methylpyrazolo[1,5-a]pyrimidin-2-yl]-2-(4-methoxyphenyl)acetamide The title compound was prepared using the methods analogous to that described in Examples 1B-1D, substituting the product from Example 10B for the product from Example 1A, 3-(dimethylamino)-2-methylacrylaldehyde for 3-(dimethylamino)acrylaldehyde, and 2-(4-methoxyphenyl)acetyl chloride for 3,3-dimethylbutanoyl chloride. $^1$H NMR (400 MHz, DMSO-d$_6$/Deuterium Oxide) δ ppm 8.71-8.72 (bs, 1H), 8.36 (d, J=2.1 Hz, 1H), 7.27-7.30 (m, 2H), 6.89-6.92 (m, 2H), 3.74 (s, 3H), 3.57-3.58 (bs, 2H), 2.52 (s, 2H), 2.30 (d, J=1.1 Hz, 3H), 0.73 (s, 9H); MS (ESI) m/z 367.2 (M+H)$^+$.

Example 19

N-[3-(3-fluoro-4-methylphenyl)pyrazolo[1,5-a]pyrimidin-2-yl]-2-phenylacetamide

The title compound was prepared using the methods analogous to that described in Examples 1A-1D, substituting 2-fluoro-4-iodo-1-methylbenzene for 1-iodo-4-(trifluoromethoxy)benzene, and 2-phenylacetyl chloride for 3,3-dimethylbutanoyl chloride. $^1$H NMR (400 MHz, DMSO-d$_6$/Deuterium Oxide) δ ppm 9.03 (dd, J=6.9, 1.7 Hz, 1H), 8.64 (dd, J=4.0, 1.7 Hz, 1H), 7.50 (dd, J=11.6, 1.7 Hz, 1H), 7.41 (dd, J=7.8, 1.4 Hz, 1H), 7.27-7.37 (m, 5H), 7.16-7.22 (m, 1H), 7.14 (dd, J=7.0, 4.1 Hz, 1H), 3.67-3.70 (bs, 2H), 2.24 (d, J=1.7 Hz, 3H); MS (ESI) m/z 361.1 (M+H)$^+$.

Example 20

3-cyclopentyl-N-[3-(3-fluoro-4-methylphenyl)-6-methylpyrazolo[1,5-a]pyrimidin-2-yl]propanamide The title compound was prepared using the methods analogous to that described in Examples 1A-1D, substituting 2-fluoro-4-iodo-1-methylbenzene for 1-iodo-4-(trifluoromethoxy)benzene, 3-(dimethylamino)-2-methylacrylaldehyde for 3-(dimethylamino)acrylaldehyde, and 3-cyclopentylpropanoyl chloride for 3,3-dimethylbutanoyl chloride. MS (ESI) m/z 381.2 (M+H)$^+$.

Example 21

2-(3,4-dimethoxyphenyl)-N-[3-(3-fluoro-4-methylphenyl)-5,7-dimethylpyrazolo[1,5-a]pyrimidin-2-yl]acetamide The title compound was prepared using the methods analogous to that described in Examples 1A-1D, substituting 2-fluoro-4-iodo-1-methylbenzene for 1-iodo-4-(trifluoromethoxy)benzene, acetylacetone for 3-(dimethylamino)acrylaldehyde, and 2-(3,4-dimethoxyphenyl)acetyl chloride for 3,3-dimethylbutanoyl chloride. MS (ESI) m/z 449.3 (M+H)$^+$.

Example 22

3,3-dimethyl-N-{3-[3-(trifluoromethoxy)phenyl]pyrazolo[1,5-a]pyrimidin-2-yl}butanamide The title compound was prepared using the methods analogous to that described in Examples 1A-1D except substituting 1-iodo-3-(trifluoromethoxy)benzene for 1-iodo-4-(trifluoromethoxy)benzene. $^1$H NMR (400 MHz, DMSO-d$_6$) δ ppm 10.18-10.20 (bs, 1H), 9.14 (dd, J=6.9, 1.7 Hz, 1H), 8.66 (dd, J=4.1, 1.7 Hz, 1H), 7.88 (d, J=7.4 Hz, 1H), 7.75-7.77 (bs, 1H), 7.55 (dd, J=8.0 Hz, 1H), 7.26 (ddd, J=8.2, 2.6, 1.3 Hz, 1H), 7.17 (dd, J=6.9, 4.1 Hz, 1H), 2.24 (s, 2H), 1.02 (s, 9H); MS (ESI) m/z 393 (M+H)$^+$.

Example 23

3-cyclopentyl-N-[3-(4-fluorophenyl)pyrazolo[1,5-a]pyrimidin-2-yl]propanamide

The title compound was prepared using the methods analogous to that described in Examples 1A-1D, substituting 1-fluoro-4-iodobenzene for 1-iodo-4-(trifluoromethoxy)benzene, and 3-cyclopentylpropanoyl chloride for 3,3-dimethylbutanoyl chloride. $^1$H NMR (500 MHz, DMSO-d$_6$/Deuterium Oxide) δ ppm 9.03 (dd, J=6.9, 1.7 Hz, 1H), 8.61 (dd, J=4.1, 1.7 Hz, 1H), 7.75-7.79 (m, 2H), 7.23-7.28 (m, 2H), 7.13 (dd, J=7.0, 4.0 Hz, 1H), 2.30-2.38 (m, 2H), 1.66-1.78 (m, 3H), 1.52-1.64 (m, 4H), 1.42-1.52 (m, 2H), 1.07-1.10 (m, 2H); MS (ESI) m/z 353.1 (M+H)$^+$.

Example 24

3-cyclohexyl-N-[3-(4-fluorophenyl)pyrazolo[1,5-a]pyrimidin-2-yl]propanamide

The title compound was prepared using the methods analogous to that described in Examples 1A-1D, substituting 1-fluoro-4-iodobenzene for 1-iodo-4-(trifluoromethoxy)benzene, and 3-cyclohexylpropanoyl chloride for 3,3-dimethylbutanoyl chloride. $^1$H NMR (500 MHz, DMSO-d$_6$/Deuterium Oxide) δ ppm 9.03 (dd, J=7.0, 1.7 Hz, 1H), 8.61 (dd, J=4.1, 1.7 Hz, 1H), 7.75-7.79 (m, 2H), 7.22-7.29 (m, 2H), 7.13 (dd, J=6.9, 4.1 Hz, 1H), 2.31-2.36 (m, 2H), 1.57-1.76 (m, 5H), 1.40-1.52 (m, 2H), 1.06-1.26 (m, 4H), 0.78-0.94 (m, 2H); MS (ESI) m/z 367.1 (M+H)$^+$.

Example 25

N-[3-(4-fluorophenyl)-6-methylpyrazolo[1,5-a]pyrimidin-2-yl]-2-phenylacetamide

The title compound was prepared using the methods analogous to that described in Examples 1A-1D, substituting 1-fluoro-4-iodobenzene for 1-iodo-4-(trifluoromethoxy)benzene, 3-(dimethylamino)-2-methylacrylaldehyde for 3-(dimethylamino)acrylaldehyde, and 2-phenylacetyl chloride for 3,3-dimethylbutanoyl chloride. $^1$H NMR (500 MHz, DMSO-d$_6$/Deuterium Oxide) δ ppm 8.86-8.87 (bs, 1H), 8.52 (d, J=2.1 Hz, 1H), 7.65-7.69 (m, 2H), 7.27-7.41 (m, 5H), 7.06-7.11 (m, 2H), 3.66-3.67 (bs, 2H), 2.35 (s, 3H); MS (ESI) m/z 361.1 (M+H)$^+$.

Example 26

N-[3-(4-fluorophenyl)-6-methylpyrazolo[1,5-a]pyrimidin-2-yl]-2-(3-methoxyphenyl)acetamide The title compound was prepared using the methods analogous to that described in Examples 1A-1D, substituting 1-fluoro-4-iodobenzene for 1-iodo-4-(trifluoromethoxy)benzene, 3-(dimethylamino)-2-methylacrylaldehyde for 3-(dimethylamino)acrylaldehyde, and 2-(3-methoxyphenyl)acetyl chloride for 3,3-dimethylbutanoyl chloride. $^1$H NMR (500 MHz, DMSO-d$_6$/Deuterium Oxide) δ ppm 8.86-8.88 (bs, 1H), 8.52 (d, J=2.1 Hz, 1H), 7.65-7.68 (m, 2H), 7.19-7.30 (m, 1H), 7.06-7.11 (m, 2H), 6.90-6.97 (m, 2H), 6.88 (d, J=7.6 Hz, 1H), 3.75 (s, 3H), 3.62-3.64 (bs, 2H), 2.35 (d, J=0.6 Hz, 3H); MS (ESI) m/z 391.1 (M+H)$^+$.

Example 27

2-(4-chlorophenyl)-N-[3-(4-fluorophenyl)-6-methylpyrazolo[1,5-a]pyrimidin-2-yl]acetamide The title compound was prepared using the methods analogous to that described in Examples 1A-1D, substituting 1-fluoro-4-iodobenzene for 1-iodo-4-(trifluoromethoxy)benzene, 3-(dimethylamino)-2-methylacrylaldehyde for 3-(dimethylamino)acrylaldehyde, and 2-(4-chlorophenyl)acetyl chloride for 3,3-dimethylbutanoyl chloride. $^1$H NMR (500 MHz, DMSO-d$_6$/Deuterium Oxide) δ ppm 8.86-8.87 (bs, 1H), 8.52 (d, J=2.1 Hz, 1H), 7.65-7.68 (m, 2H), 7.39-7.45 (m, 2H), 7.32-7.39 (m, 2H), 7.09-7.13 (m, 2H), 3.65-3.68 (bs, 2H), 2.35 (d, J=0.8 Hz, 3H); MS (ESI) m/z 395.0 (M+H)$^+$.

Example 28

2-(4-fluorophenyl)-N-[3-(4-fluorophenyl)-7-methylpyrazolo[1,5-a]pyrimidin-2-yl]acetamide The title compound was prepared using the methods analogous to that described in Examples 1A-1D, substituting 1-fluoro-4-iodobenzene for 1-iodo-4-(trifluoromethoxy)benzene, 4-(dimethylamino)but-3-en-2-one for 3-(dimethylamino)acrylaldehyde, and 2-(4-fluorophenyl)acetyl chloride for 3,3-dimethylbutanoyl chloride. $^1$H NMR (500 MHz, DMSO-d$_6$/Deuterium Oxide) δ ppm 8.51 (d, J=4.2 Hz, 1H), 7.66-7.69 (m, 2H), 7.32-7.42 (m, 2H), 7.15-7.23 (m, 2H), 7.09-7.14 (m, 2H), 7.08 (dd, J=4.3, 0.8 Hz, 1H), 3.67-3.68 (bs, 2H), 2.72 (s, 3H); MS (ESI) m/z 379.1 (M+H)$^+$.

Example 29

N-[3-(4-fluorophenyl)-5,7-dimethylpyrazolo[1,5-a]pyrimidin-2-yl]-3-phenylpropanamide The title compound was prepared using the methods analogous to that described in Examples 1A-1D, substituting 1-fluoro-4-iodobenzene for 1-iodo-4-(trifluoromethoxy)benzene, acetylacetone for 3-(dimethylamino)acrylaldehyde, and 3-phenylpropanoyl chloride for 3,3-dimethylbutanoyl chloride. $^1$H NMR (500 MHz, DMSO-d$_6$/Deuterium Oxide) δ ppm 7.68-7.72 (m, 2H), 7.27-7.34 (m, 2H), 7.20-7.27 (m, 3H), 7.14-7.20 (m, 2H), 6.96 (d, J=0.8 Hz, 1H), 2.84-2.94 (m, 2H), 2.66-2.71 (m, 2H), 2.66 (d, J=0.6 Hz, 3H), 2.53 (s, 3H); MS (ESI) m/z 389.2 (M+H)$^+$.

Example 30

N-[3-(4-fluoro-3-methylphenyl)pyrazolo[1,5-a]pyrimidin-2-yl]-3-phenylpropanamide The title compound was prepared using the methods analogous to that described in Examples 1A-1D, substituting 4-bromo-1-fluoro-2-methylbenzene for 1-iodo-4-(trifluoromethoxy)benzene, and 3-phenylpropanoyl chloride for 3,3-dimethylbutanoyl chloride. $^1$H NMR (500 MHz, DMSO-d$_6$/Deuterium Oxide) δ ppm 9.02 (dd, J=7.0, 1.7 Hz, 1H), 8.61 (dd, J=4.1, 1.7 Hz, 1H), 7.63 (dd, J=7.6, 2.3 Hz, 1H), 7.47-7.52 (m, 1H), 7.27-7.32 (m, 2H), 7.18-7.27 (m, 3H), 7.10-7.16 (m, 2H), 2.87-2.91 (m, 2H), 2.64-2.68 (m, 2H), 2.26 (d, J=1.5 Hz, 3H); MS (ESI) m/z 375.1 (M+H)$^+$.

Example 31

N-[3-(4-fluoro-3-methylphenyl)pyrazolo[1,5-a]pyrimidin-2-yl]-2-(4-fluorophenyl)acetamide The title compound was prepared using the methods analogous to that described in Examples 1A-1D, substituting 4-bromo-1-fluoro-2-methylbenzene for 1-iodo-4-(trifluoromethoxy)benzene, and 2-(4-fluorophenyl)acetyl chloride for 3,3-dimethylbutanoyl chloride. $^1$H NMR (500 MHz, DMSO-d$_6$/Deuterium Oxide) δ ppm 9.02 (dd, J=7.0, 1.7 Hz, 1H), 8.61 (dd, J=4.0, 1.7 Hz, 1H), 7.53 (dd, J=7.6, 1.5 Hz, 1H), 7.48 (ddd, J=8.1, 5.3, 2.6 Hz, 1H), 7.31-7.37 (m, 2H), 7.14-7.21 (m, 2H), 7.12 (dd, J=7.0, 4.1 Hz, 1H), 7.06 (dd, J=9.1 Hz, 1H), 3.66-3.67 (bs, 2H), 2.17 (d, J=1.1 Hz, 3H); MS (ESI) m/z 379.1 (M+H)$^+$.

Example 32

N-[3-(4-fluoro-3-methylphenyl)-5,7-dimethylpyrazolo[1,5-a]pyrimidin-2-yl]-2-(3-methoxyphenyl)acetamide The title compound was prepared using the methods analogous to that described in Examples 1A-1D, substituting 4-bromo-1-fluoro-2-methylbenzene for 1-iodo-4-(trifluoromethoxy)benzene, acetylacetone for 3-(dimethylamino)acrylaldehyde, and 2-(3-methoxyphenyl)acetyl chloride for 3,3-dimethylbutanoyl chloride. $^1$H NMR (500 MHz, DMSO-d$_6$/Deuterium Oxide) δ ppm 7.47-7.51 (m, 2H), 7.23-7.29 (m, 1H), 6.98-7.04 (m, 1H), 6.96 (d, J=0.8 Hz, 1H), 6.88-6.94 (m, 2H), 6.84-6.88 (m, 1H), 3.75 (s, 3H), 3.61-3.63 (bs, 2H), 2.65-2.67 (bs, 3H), 2.12-2.16 (bs, 3H); MS (ESI) m/z 419.1 (M+H)$^+$.

Example 33

N-[3-(4-fluoro-3-methylphenyl)-5,7-dimethylpyrazolo[1,5-a]pyrimidin-2-yl]-3,3-dimethylbutanamide The title compound was prepared using the methods analogous to that described in Examples 1A-1D, substituting 4-bromo-1-fluoro-2-methylbenzene for 1-iodo-4-(trifluoromethoxy)benzene, and acetylacetone for 3-(dimethylamino)acrylaldehyde. $^1$H NMR (500 MHz, DMSO-d$_6$/Deuterium Oxide) δ ppm 7.56-7.60 (m, 2H), 7.13-7.19 (m, 1H), 6.95 (d, J=1.1 Hz, 1H), 2.66 (d, J=0.9 Hz, 3H), 2.52 (s, 3H), 2.25 (d, J=1.8 Hz, 3H), 2.21-2.22 (bs, 2H), 1.00 (s, 9H); MS (ESI) m/z 369.2 (M+H)$^+$.

Example 34

2-cyclohexyl-N-[3-(4-fluoro-3-methylphenyl)-5,7-dimethylpyrazolo[1,5-a]pyrimidin-2-yl]acetamide The title compound was prepared using the methods analogous to that described in Examples 1A-1D, substituting 4-bromo-1-fluoro-2-methylbenzene for 1-iodo-4-(trifluoromethoxy)benzene, acetylacetone for 3-(dimethylamino)acrylaldehyde, and 2-cyclohexylacetyl chloride for 3,3-dimethylbutanoyl chloride. $^1$H NMR (500 MHz, DMSO-d$_6$/Deuterium Oxide) δ ppm 7.55-7.60 (m, 2H), 7.13-7.19 (m, 1H), 6.96 (d, J=1.1 Hz, 1H), 2.66 (s, 3H), 2.53 (s, 3H), 2.26 (d, J=1.4 Hz, 3H), 2.19 (d, J=6.1 Hz, 2H), 1.57-1.74 (m, 6H), 1.06-1.26 (m, 3H), 0.87-1.04 (m, 2H); MS (ESI) m/z 395.2 (M+H)$^+$.

Example 35

3-cyclohexyl-N-[3-(4-fluoro-3-methylphenyl)-6-methylpyrazolo[1,5-a]pyrimidin-2-yl]propanamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and 3-cyclohexylpropionyl chloride for 3,3-dimethylbutanoyl chloride. $^1$H NMR (300 MHz, DMSO-d$_6$): δ ppm 0.81-0.93 (m, 2H), 1.09-1.23 (m, 4H), 1.42-1.50 (m, 2H), 1.57-1.75 (m, 5H), 2.26-2.35 (m, 8H), 7.13-7.19 (m, 1H), 7.58-7.64 (m, 2H), 8.52 (d, J=2.0 Hz, 1H), 8.92 (dd, J=2.0, 1.2 Hz, 1H), 10.05 (s, 1H); MS (DCI) m/z 395 (M+H)$^+$.

Example 36

N-[3-(2,2-dimethylpropyl)-7-methylpyrazolo[1,5-a]pyrimidin-2-yl]-2-(4-methoxyphenyl)acetamide The title compound was prepared using the methods analogous to that described in Examples 1B-1D, substituting the product from Example 10B for the product from Example 1A, 4-(dimethylamino)but-3-en-2-one for 3-(dimethylamino)acrylaldehyde, and 2-(4-methoxyphenyl)acetyl chloride for 3,3-dimethylbutanoyl chloride. $^1$H NMR (500 MHz, DMSO-d$_6$/Deuterium Oxide) δ ppm 8.36 (d, J=4.2 Hz, 1H), 7.28-7.31 (m, 2H), 6.90-6.92 (m, 3H), 3.74-3.74 (bs, 3H), 3.60 (d, J=2.5 Hz, 2H), 2.66 (s, 3H), 2.55-2.56 (bs, 2H), 0.73 (s, 9H); MS (ESI) m/z 367.2 (M+H)$^+$.

Example 37

3-cyclohexyl-N-[3-(2,2-dimethylpropyl)-7-methylpyrazolo[1,5-a]pyrimidin-2-yl]propanamide The title compound was prepared using the methods analogous to that described in Examples 1B-1D, substituting the product from Example 10B for the product from Example 1A, 4-(dimethylamino)but-3-en-2-one for 3-(dimethylamino)acrylaldehyde, and 3-cyclohexylpropanoyl chloride for 3,3-dimethylbutanoyl chloride. $^1$H NMR (500 MHz, DMSO-d$_6$/Deuterium Oxide) δ ppm 8.37 (d, J=4.2 Hz, 1H), 6.92 (dd, J=4.2, 1.1 Hz, 1H), 2.66 (d, J=0.9 Hz, 3H), 2.64 (s, 2H), 2.36 (t, J=7.4 Hz, 2H), 1.58-1.75 (m, 5H), 1.51 (q, J=7.3 Hz, 2H), 1.09-1.29 (m, 4H), 0.86-0.95 (m, 2H), 0.84 (s, 9H); MS (ESI) m/z 357.2 (M+H)$^+$.

Example 38

N-[3-(2,2-dimethylpropyl)-7-methylpyrazolo[1,5-a]pyrimidin-2-yl]-2-(3-methoxyphenyl)acetamide The title compound was prepared using the methods analogous to that described in Examples 1B-1D, substituting the product from Example 10B for the product from Example 1A, 4-(dimethylamino)but-3-en-2-one for 3-(dimethylamino)acrylaldehyde, and 2-(3-methoxyphenyl)acetyl chloride for 3,3-dimethylbutanoyl chloride. $^1$H NMR (500 MHz, DMSO-d$_6$/Deuterium Oxide) δ ppm 8.36 (d, J=4.2 Hz, 1H), 7.27 (dd, J=6.3 Hz, 1H), 6.93-7.00 (m, 2H), 6.92 (dd, J=4.2, 0.8 Hz, 1H), 6.85 (dd, J=8.3, 2.5 Hz, 1H), 3.75 (s, 3H), 3.62-3.66 (bs, 2H), 2.66 (s, 3H), 2.54-2.56 (bs, 2H), 0.72 (s, 9H); MS (ESI) m/z 367.2 (M+H)$^+$.

Example 39

N-[3-(4-chlorophenyl)-6-methylpyrazolo[1,5-a]pyrimidin-2-yl]-2-(3,4-dimethoxyphenyl)acetamide The title compound was prepared using the methods analogous to that described in Examples 1A-1D, substituting 1-chloro-4-iodobenzene for 1-iodo-4-(trifluoromethoxy)benzene, 3-(dimethylamino)-2-methylacrylaldehyde for 3-(dimethylamino)acrylaldehyde, and 2-(3,4-dimethoxyphenyl)acetyl chloride for 3,3-dimethylbutanoyl chloride. $^1$H NMR (500 MHz, DMSO-d$_6$/Deuterium Oxide) δ ppm 8.88 (s, 1H), 8.53 (d, J=2.1 Hz, 1H), 7.62-7.68 (m, 2H), 7.24-7.31 (m, 2H), 6.83-6.99 (m, 3H), 3.77 (s, 3H), 3.76 (s, 3H), 3.58 (s, 2H), 2.36 (d, J=0.8 Hz, 3H); MS (ESI) m/z 437.1 (M+H)$^+$.

Example 40

N-[3-(4-chlorophenyl)-7-methylpyrazolo[1,5-a]pyrimidin-2-yl]-3,3-dimethylbutanamide The title compound was prepared using the methods analogous to that described in Examples 1A-1D, substituting 1-chloro-4-iodobenzene for 1-iodo-4-(trifluoromethoxy)benzene, and 4-(dimethylamino)but-3-en-2-one for 3-(dimethylamino)acrylaldehyde. $^1$H NMR (500 MHz, DMSO-d$_6$/Deuterium Oxide) δ ppm 8.52 (d, J=4.2 Hz, 1H), 7.77-7.80 (m, 2H), 7.45-7.47 (m, 2H), 7.09 (dd, J=4.2, 0.8 Hz, 1H), 2.73 (s, 3H), 2.24 (s, 2H), 1.01 (s, 9H); MS (ESI) m/z 357.1 (M+H)$^+$.

Example 41

N-[3-(4-chlorophenyl)-7-methylpyrazolo[1,5-a]pyrimidin-2-yl]-2-(3-methoxyphenyl)acetamide The title compound was prepared using the methods analogous to that described in Examples 1A-1D, substituting 1-chloro-4-iodobenzene for 1-iodo-4-(trifluoromethoxy)benzene, 4-(dimethylamino)but-3-en-2-one for 3-(dimethylamino)acrylaldehyde, and 2-(3-methoxyphenyl)acetyl chloride for 3,3-dimethylbutanoyl chloride. $^1$H NMR (500 MHz, DMSO-d$_6$/Deuterium Oxide) δ ppm 8.53 (d, J=4.2 Hz, 1H), 7.65-7.67 (m, 2H), 7.27-7.30 (m, 3H), 7.08-7.12 (m, 1H), 6.86-6.98 (m, 3H), 3.76 (s, 3H), 3.64-3.65 (bs, 2H), 2.72 (s, 3H); MS (ESI) m/z 407.1 (M+H)$^+$.

Example 42

N-[3-(4-chlorophenyl)-5,7-dimethylpyrazolo[1,5-a]pyrimidin-2-yl]-2-cyclohexylacetamide The title compound was prepared using the methods analogous to that described in Examples 1A-1D, substituting 1-chloro-4-iodobenzene for 1-iodo-4-(trifluoromethoxy)benzene, acetylacetone for 3-(dimethylamino)acrylaldehyde, and 2-cyclohexylacetyl chloride for 3,3-dimethylbutanoyl chloride. $^1$H NMR (500 MHz, DMSO-d$_6$/Deuterium Oxide) δ ppm 7.74-7.77 (m, 2H), 7.43-7.46 (m, 2H), 6.98 (d, J=1.1 Hz, 1H), 2.66 (s, 3H), 2.54 (s, 3H), 2.20 (d, J=6.1 Hz, 2H), 1.59-1.73 (m, 6H), 1.07-1.25 (m, 3H), 0.93-1.00 (m, 2H); MS (ESI) m/z 397 (M+H)$^+$.

Example 43

N-[3-(4-chlorophenyl)-5,7-dimethylpyrazolo[1,5-a]pyrimidin-2-yl]-3-cyclopentylpropanamide The title compound was prepared using the methods analogous to that described in Examples 1A-1D, substituting 1-chloro-4-iodobenzene for 1-iodo-4-(trifluoromethoxy)benzene, acetylacetone for 3-(dimethylamino)acrylaldehyde, and 3-cyclopentylpropanoyl chloride for 3,3-dimethylbutanoyl chloride. $^1$H NMR (500 MHz, DMSO-d$_6$/Deuterium Oxide) δ ppm 7.75-7.78 (m, 2H), 7.44-7.46 (m, 2H), 6.98 (s, 1H), 2.66 (d, J=0.9 Hz, 3H), 2.54 (s, 3H), 2.29-2.38 (m, 3H), 1.69-1.74 (m, 3H), 1.43-1.64 (m, 7H); MS (ESI) m/z 397.1 (M+H)$^+$.

Example 44

N-[3-(4-chloro-3-methylphenyl)-6-methylpyrazolo[1,5-a]pyrimidin-2-yl]-3-phenylpropanamide The title compound was prepared using the methods analogous to that described in Examples 1A-1D, substituting 1-chloro-4-iodo-2-methylbenzene for 1-iodo-4-(trifluoromethoxy)benzene, 3-(dimethylamino)-2-methylacrylaldehyde for 3-(dimethylamino)acrylaldehyde, and 3-phenylpropanoyl chloride for 3,3-dimethylbutanoyl chloride. $^1$H NMR (500 MHz, DMSO-d$_6$/Deuterium Oxide) δ ppm 8.87 (dd, J=2.2, 1.3 Hz, 1H), 8.54 (d, J=2.1 Hz, 1H), 7.71 (d, J=2.2 Hz, 1H), 7.48-7.52 (m, 1H), 7.38 (d, J=8.3 Hz, 1H), 7.17-7.32 (m, 5H), 2.85-2.91 (m, 2H), 2.64-2.69 (m, 2H), 2.36 (d, J=0.8 Hz, 3H), 2.34-2.35 (bs, 3H); MS (ESI) m/z 405.1 (M+H)$^+$.

Example 45

N-[3-(4-chloro-3-methylphenyl)pyrazolo[1,5-a]pyrimidin-2-yl]-2-(4-fluorophenyl)acetamide The title compound was prepared using the methods analogous to that described in Examples 1A-1D, substituting 1-chloro-4-iodo-2-methylbenzene for 1-iodo-4-(trifluoromethoxy)benzene, and 2-(4-fluorophenyl)acetyl chloride for 3,3-dimethylbutanoyl chloride. $^1$H NMR (400 MHz, DMSO-d$_6$/Deuterium Oxide) δ ppm 9.03 (dd, J=6.9, 1.7 Hz, 1H), 8.63 (dd, J=4.0, 1.7 Hz, 1H), 7.60 (d, J=2.2 Hz, 1H), 7.50 (dd, J=8.3, 2.2 Hz, 1H), 7.33-7.40 (m, 2H), 7.31 (d, J=8.4 Hz, 1H), 7.14-7.21 (m, 2H), 7.14 (dd, J=7.0, 4.1 Hz, 1H), 3.66-3.68 (bs, 2H), 2.25 (s, 3H); MS (ESI) m/z 395.0 (M+H)$^+$.

Example 46

N-[3-(4-chloro-3-methylphenyl)-7-methylpyrazolo[1,5-a]pyrimidin-2-yl]-3-cyclopentylpropanamide The title compound was prepared using the methods analogous to that described in Examples 1A-1D, substituting 1-chloro-4-iodo-2-methylbenzene for 1-iodo-4-(trifluoromethoxy)benzene, 4-(dimethylamino)but-3-en-2-one for 3-(dimethylamino)acrylaldehyde, and 3-cyclopentylpropanoyl chloride for 3,3-dimethylbutanoyl chloride. $^1$H NMR (500 MHz, DMSO-d$_6$/Deuterium Oxide) δ ppm 8.53 (d, J=4.2 Hz, 1H), 7.69-7.70 (bs, 1H), 7.62 (dd, J=8.2, 2.2 Hz, 1H), 7.43 (d, J=8.2 Hz, 1H), 7.09 (dd, J=4.2, 1.1 Hz, 1H), 2.72 (s, 3H), 2.36 (s, 3H), 2.32-2.37 (m, 1H), 1.47-1.76 (m, 10H), 1.02-1.14 (m, 2H); MS (ESI) m/z 397.1 (M+H)$^+$.

Example 47

N-[3-(4-chloro-3-methylphenyl)-5,7-dimethylpyrazolo[1,5-a]pyrimidin-2-yl]-3-phenylpropanamide Example 47A 2-(4-Chloro-3-methylphenyl)malononitrile A solution of malononitrile (1.79 mL, 28.4 mmol) in THF (6 mL) was added dropwise over 25 minutes to a vigorously stirred, ice-cooled suspension of NaH (60% dispersion in mineral oil, 1.70 g, 42.6 mmol) in THF (40 mL) under a nitrogen atmosphere. The resulting slurry was allowed to warm to room temperature. Meanwhile tris(dibenzylideneacetone)dipalladium(0) (167 mg, 0.182 mmol) and 1,3-bis(2,6-diisopropylphenyl)imidazolium chloride (151 mg, 0.36 mmol) were combined in THF (5 mL) and warmed to 60° C. for 10 minutes, then cooled to room temperature. This solution and 2-chloro-5-iodotoluene (3.66 g, 14.2 mmol) were added to the malononitrile solution with THF (40 mL) rinse, and the grey mixture was heated at reflux under nitrogen for 37 hours, then cooled to room temperature and concentrated under vacuum. Water (50 mL) was added to the residue and the mixture was extracted with CH$_2$Cl$_2$ (2×40 mL). The aqueous phase (pH~10) was made acidic (pH~3) by addition of 10% HCl (10 mL) and extracted again with CH$_2$Cl$_2$ (2×40 mL). The combined organic extract was concentrated and the residual red-brown oily residue was purified by flash chromatography (silica gel, eluted with hexanes-EtOAc, 90:10-70:30) to provide the title compound as a tan solid. $^1$H NMR (300 MHz, CDCl$_3$) δ ppm 2.44 (s, 3H) 5.00 (s, 1H) 7.27 (dd, J=8.1, 2.4 Hz, 1H) 7.37 (d, J=2.4 Hz, 1H) 7.47 (d, J=8.1 Hz, 1H).

Example 47B 4-(4-Chloro-3-methylphenyl)-1H-pyrazole-3,5-diamine

Hydrazine monohydrate (0.312 mL, 6.4 mmol) was added to a solution of the product from Example 47A (512 mg, 2.69 mmol) in CHCl$_3$ (25 mL). The reaction flask was evacuated and purged with nitrogen (3 cycles) and the mixture was heated at 70° C. under nitrogen for 22 hours, then cooled to room temperature. The mixture was concentrated under vacuum to provide the title compound as a beige solid. MS (DCI/NH$_3$) m/z 223/225 (M+H)$^+$.

Example 47C 3-(4-Chloro-3-methylphenyl)-5,7-dimethylpyrazolo[1,5-a]pyrimidin-2-amine A solution of acetylacetone (85 mg, 0.85 mmol) in acetic acid (4 mL) was added to the product from Example 47B (141 mg, 0.63 mmol) and the resulting mixture was heated at 100° C. for 1 hour, then cooled to room temperature. Hydroxylamine hydrochloride (58 mg, 0.83 mmol) was added, and the solution was stirred at room temperature for 2 hours, then concentrated under vacuum. The residue was crystallized from ethanol (4 mL) to provide the title compound. MS (ESI) m/z 287/289 (M+H)$^+$.

Example 47D

N-[3-(4-chloro-3-methylphenyl)-5,7-dimethylpyrazolo[1,5-a]pyrimidin-2-yl]-3-phenylpropanamide 3-Phenylpropionyl chloride (0.078 mL, 0.53 mmol) was added to a stirring solution of the product from Example 47C (85 mg, 0.296 mmol) in pyridine (5 mL), and the mixture was stirred at room temperature for 12 hours. The mixture was concentrated under vacuum, and the residue diluted with MeOH (5 mL) and stirred for 30 minutes at room temperature. The mixture was concentrated under vacuum and the residue was crystallized from 80% aqueous ethanol (15 mL) to provide the title compound. $^1$H NMR (300 MHz, DMSO-d$_6$) δ ppm 2.34 (s, 3H) 2.53 (s, 3H) 2.60-2.69 (m, 2H) 2.66 (s, 3H) 2.87 (t, J=7.6 Hz, 2H) 6.98 (d, J=0.7 Hz, 1H) 7.14-7.32 (m, 5H) 7.38 (d, J=8.5 Hz, 1H) 7.56 (dd, J=8.5, 2.0 Hz, 1H) 7.72 (d, J=1.7 Hz, 1H) 10.21 (s, 1H); MS (ESI) m/z 419/421 (M+H)$^+$.

Example 48

N-[3-(4-chloro-3-methylphenyl)-5,7-dimethylpyrazolo[1,5-a]pyrimidin-2-yl]-3-cyclohexylpropanamide The title compound was prepared using the methods analogous to that described in Examples 1A-1D, substituting 1-chloro-4-iodo-2-methylbenzene for 1-iodo-4-(trifluoromethoxy)benzene, acetylacetone for 3-(dimethylamino)acrylaldehyde, and 3-cyclohexylpropanoyl chloride for 3,3-dimethylbutanoyl chloride. $^1$H NMR (400 MHz, DMSO-d$_6$/Deuterium Oxide) δ ppm 7.67-7.68 (bs, 1H), 7.61 (dd, J=8.3, 2.2 Hz, 1H), 7.43 (d, J=8.2 Hz, 1H), 6.97 (d, J=1.1 Hz, 1H), 2.66 (d, J=0.8 Hz, 3H), 2.54 (s, 3H), 2.36 (s, 3H), 2.29-2.36 (m, 2H), 1.57-1.74 (m, 5H), 1.40-1.50 (m, 2H), 1.08-1.25 (m, 4H), 0.79-0.93 (m, 2H); MS (ESI) m/z 425.2 (M+H)$^+$.

Example 49

N-[3-(3-chlorophenyl)-7-methylpyrazolo[1,5-a]pyrimidin-2-yl]-3-phenylpropanamide The title compound was prepared using the methods analogous to that described in Examples 1A-1D, substituting 1-chloro-3-iodobenzene for 1-iodo-4-(trifluoromethoxy)benzene, 4-(dimethylamino)but-3-en-2-one for 3-(dimethylamino)acrylaldehyde, and 3-phenylpropanoyl chloride for 3,3-dimethylbutanoyl chloride. $^1$H NMR (500 MHz, DMSO-d$_6$/Deuterium Oxide) δ ppm 8.56 (d, J=4.2 Hz, 1H), 7.87 (dd, J=1.8 Hz, 1H), 7.66 (d, J=7.6 Hz, 1H), 7.40 (dd, J=7.9 Hz, 1H), 7.28-7.35 (m, 3H), 7.19-7.28 (m, 3H), 7.12 (dd, J=4.3, 1.1 Hz, 1H), 2.90 (t, J=7.8 Hz, 2H), 2.73 (s, 3H), 2.64-2.70 (m, 2H); MS (ESI) m/z 391.2 (M+H)$^+$.

Example 50

N-[3-(3-chlorophenyl)-6-methylpyrazolo[1,5-a]pyrimidin-2-yl]-2-(4-methoxyphenyl)acetamide The title compound was prepared using the methods analogous to that described in Examples 1A-1D, substituting 1-chloro-3-iodobenzene for 1-iodo-4-(trifluoromethoxy)benzene, 3-(dimethylamino)-2-methylacrylaldehyde for 3-(dimethylamino)acrylaldehyde, and 2-(4-methoxyphenyl)acetyl chloride for 3,3-dimethylbutanoyl chloride. $^1$H NMR (500 MHz, DMSO-d$_6$/Deuterium Oxide) δ ppm 8.89-8.90 (bs, 1H), 8.57 (d, J=2.1 Hz, 1H), 7.80-7.82 (m, 1H), 7.58-7.61 (m, 1H), 7.22-7.34 (m, 4H), 6.83-6.98 (m, 2H), 3.75 (s, 3H), 3.60-3.61 (bs, 2H), 2.36 (s, 3H); MS (ESI) m/z 407.1 (M+H)$^+$.

Example 51

N-[3-(3-chlorophenyl)-6-methylpyrazolo[1,5-a]pyrimidin-2-yl]-3,3-dimethylbutanamide The title compound was prepared using the methods analogous to that described in Examples 1A-1D, substituting 1-chloro-3-iodobenzene for 1-iodo-4-(trifluoromethoxy)benzene, and 3-(dimethylamino)-2-methylacrylaldehyde for 3-(dimethylamino)acrylaldehyde. $^1$H NMR (500 MHz, DMSO-d$_6$/Deuterium Oxide) δ ppm 8.90 (dd, J=2.2, 1.1 Hz, 1H), 8.56 (d, J=2.1 Hz, 1H), 7.80-7.82 (m, 1H), 7.77 (ddd, J=7.8, 1.1 Hz, 1H), 7.44 (dd, J=7.9 Hz, 1H), 7.32 (ddd, J=8.0, 2.2, 1.1 Hz, 1H), 2.37 (d, J=1.1 Hz, 3H), 2.24-2.24 (bs, 2H), 1.03 (s, 9H); MS (ESI) m/z 357.0 (M+H)$^+$.

Example 52

N-[3-(3-chlorophenyl)-5,7-dimethylpyrazolo[1,5-a]pyrimidin-2-yl]-2-cyclohexylacetamide The title compound was prepared using the methods analogous to that described in Examples 1A-1D, substituting 1-chloro-3-iodobenzene for 1-iodo-4-(trifluoromethoxy)benzene, acetylacetone for 3-(dimethylamino)acrylaldehyde, and 2-cyclohexylacetyl chloride for 3,3-dimethylbutanoyl chloride. $^1$H NMR (500 MHz, DMSO-d$_6$/Deuterium Oxide) δ ppm 7.76-7.79 (m, 2H), 7.41-7.46 (m, 1H), 7.29-7.32 (m, 1H), 7.00 (s, 1H), 2.67 (s, 3H), 2.55 (s, 3H), 2.22 (d, J=5.6 Hz, 2H), 1.58-1.69 (m, 6H), 1.07-1.26 (m, 3H), 0.90-1.03 (m, 2H); MS (ESI) m/z 397.1 (M+H)$^+$.

Example 53

N-[3-(3-chlorophenyl)-5,7-dimethylpyrazolo[1,5-a]pyrimidin-2-yl]-2-cyclopentylacetamide The title compound was prepared using the methods analogous to that described in Examples 1A-1D, substituting 1-chloro-3-iodobenzene for 1-iodo-4-(trifluoromethoxy)benzene, acetylacetone for 3-(dimethylamino)acrylaldehyde, and 2-cyclopentylacetyl chloride for 3,3-dimethylbutanoyl chloride. $^1$H NMR (500 MHz, DMSO-d$_6$/Deuterium Oxide) δ ppm 7.77-7.79 (m, 2H), 7.42-7.46 (m, 1H), 7.30-7.32 (m, 1H), 7.00 (d, J=1.1 Hz, 1H), 2.67 (d, J=0.9 Hz, 3H), 2.55 (s, 3H), 2.34 (d, J=7.2 Hz, 2H), 2.20 (p, J=7.5 Hz, 1H), 1.71-1.76 (m, 2H), 1.56-1.66 (m, 2H), 1.44-1.56 (m, 2H), 1.11-1.25 (m, 2H); MS (ESI) m/z 383.1 (M+H)$^+$.

Example 54

N-[3-(3-chlorophenyl)-5,7-dimethylpyrazolo[1,5-a]pyrimidin-2-yl]-2-(3-methoxyphenyl)acetamide The title compound was prepared using the methods analogous to that described in Examples 1A-1D, substituting 1-chloro-3-iodobenzene for 1-iodo-4-(trifluoromethoxy) benzene, acetylacetone for 3-(dimethylamino)acrylaldehyde, and 2-(3-methoxyphenyl)acetyl chloride for 3,3-dimethylbutanoyl chloride. MS (ESI) m/z 421.1 (M+H)$^+$.

Example 55

N-[3-(3-chlorophenyl)pyrazolo[1,5-a]pyrimidin-2-yl]-2-(2,5-dimethoxyphenyl)acetamide The title compound was prepared using the methods analogous to that described in Examples 1A-1D, substituting 1-chloro-3-iodobenzene for 1-iodo-4-(trifluoromethoxy) benzene, and 2-(2,5-dimethoxyphenyl)acetyl chloride for 3,3-dimethylbutanoyl chloride. MS (ESI) m/z 423.1 (M+H)$^+$.

Example 56

N-[3-(3-chlorophenyl)pyrazolo[1,5-a]pyrimidin-2-yl]-3-cyclopentylpropanamide

The title compound was prepared using the methods analogous to that described in Examples 1A-1D, substituting 1-chloro-3-iodobenzene for 1-iodo-4-(trifluoromethoxy) benzene, and 3-cyclopentylpropanoyl chloride for 3,3-dimethylbutanoyl chloride. $^1$H NMR (500 MHz, DMSO-d$_6$/Deuterium Oxide) δ ppm 9.05 (dd, J=6.9, 1.7 Hz, 1H), 8.66 (dd, J=4.1, 1.7 Hz, 1H), 7.79-7.82 (m, 1H), 7.75-7.79 (m, 1H), 7.46 (dd, J=7.9 Hz, 1H), 7.34 (ddd, J=8.0, 2.1, 1.1 Hz, 1H), 7.16 (dd, J=6.9, 4.1 Hz, 1H), 2.32-2.40 (m, 2H), 1.73-1.75 (m, 3H), 1.53-1.64 (m, 4H), 1.43-1.53 (m, 2H), 1.02-1.15 (m, 2H); MS (ESI) m/z 369.1 (M+H)$^+$.

Example 57

N-[3-(3-chlorophenyl)pyrazolo[1,5-a]pyrimidin-2-yl]-2-phenylacetamide

The title compound was prepared using the methods analogous to that described in Examples 1A-1D, substituting 1-chloro-3-iodobenzene for 1-iodo-4-(trifluoromethoxy) benzene, and 2-phenylacetyl chloride for 3,3-dimethylbutanoyl chloride. $^1$H NMR (500 MHz, DMSO-d$_6$/Deuterium Oxide) δ ppm 9.05 (dd, J=7.0, 1.7 Hz, 1H), 8.66 (dd, J=4.1, 1.7 Hz, 1H), 7.83-7.84 (m, 1H), 7.56-7.61 (m, 1H), 7.32-7.38 (m, 4H), 7.28-7.32 (m, 3H), 7.16 (dd, J=7.0, 4.1 Hz, 1H), 3.69 (s, 2H); MS (ESI) m/z 363.0 (M+H)$^+$.

Example 58

2-(4-chlorophenyl)-N-[3-(3-chlorophenyl)pyrazolo[1,5-a]pyrimidin-2-yl]acetamide

The title compound was prepared using the methods analogous to that described in Examples 1A-1D, substituting 1-chloro-3-iodobenzene for 1-iodo-4-(trifluoromethoxy) benzene, and 2-(4-chlorophenyl)acetyl chloride for 3,3-dimethylbutanoyl chloride. $^1$H NMR (500 MHz, DMSO-d$_6$/Deuterium Oxide) δ ppm 9.05 (dd, J=7.0, 1.7 Hz, 1H), 8.66 (dd, J=4.1, 1.7 Hz, 1H), 7.77 (dd, J=2.2, 1.5 Hz, 1H), 7.60-7.62 (m, 1H), 7.29-7.41 (m, 6H), 7.17 (dd, J=7.0, 4.1 Hz, 1H), 3.70 (s, 2H); MS (ESI) m/z 397.0 (M+H)$^+$.

Example 59

N-{6-methyl-3-[4-(trifluoromethyl)phenyl]pyrazolo[1,5-a]pyrimidin-2-yl}-3-phenylpropanamide The title compound was prepared using the methods analogous to that described in Examples 1A-1D, substituting 1-iodo-4-(trifluoromethyl)benzene for 1-iodo-4-(trifluoromethoxy)benzene, 3-(dimethylamino)-2-methylacrylaldehyde for 3-(dimethylamino)acrylaldehyde, and 3-phenylpropanoyl chloride for 3,3-dimethylbutanoyl chloride. $^1$H NMR (400 MHz, DMSO-d$_6$/Deuterium Oxide) δ ppm 8.92 (dd, J=2.2, 1.1 Hz, 1H), 8.58 (d, J=2.1 Hz, 1H), 7.87-7.94 (m, 2H), 7.65-7.71 (m, 2H), 7.20-7.33 (m, 5H), 2.88-2.93 (m, 2H), 2.69-2.74 (m, 2H), 2.37 (d, J=1.1 Hz, 3H); MS (ESI) m/z 425.3 (M+H)$^+$.

Example 60

3-cyclopentyl-N-{3-[4-(trifluoromethyl)phenyl]pyrazolo[1,5-a]pyrimidin-2-yl}propanamide The title compound was prepared using the methods analogous to that described in Examples 1A-1D, substituting 1-iodo-4-(trifluoromethyl)benzene for 1-iodo-4-(trifluoromethoxy)benzene, and 3-cyclopentylpropionyl chloride for 3,3-dimethylbutanoyl chloride. $^1$H NMR (300 MHz, DMSO-d$_6$): δ ppm 1.03-1.12 (m, 2H), 1.43-1.77 (m, 9H), 2.36 (t, J=7.5 Hz, 2H), 7.18 (dd, J=7.0, 4.2 Hz, 1H), 7.74-7.77 (m, 2H), 7.99-8.01 (m, 2H), 8.66 (dd, J=4.1, 1.7 Hz, 1H), 0.13 (dd, J=6.8, 1.7 Hz, 1H), 10.30 (s, 1H); MS (DCI) m/z 403 (M+H)$^+$.

Example 61

3-cyclopentyl-N-{5,7-dimethyl-3-[4-(trifluoromethyl)phenyl]pyrazolo[1,5-a]pyrimidin-2-yl}propanamide The title compound was prepared using the methods analogous to that described in Examples 1A-1D, substituting 1-iodo-4-(trifluoromethyl)benzene for 1-iodo-4-(trifluoromethoxy)benzene, acetylacetone for 3-(dimethylamino) acrylaldehyde, and 3-cyclopentylpropanoyl chloride for 3,3-dimethylbutanoyl chloride. $^1$H NMR (400 MHz, DMSO-d$_6$/Deuterium Oxide) δ ppm 7.96-7.99 (m, 2H), 7.73-7.76 (m, 2H), 7.02 (d, J=1.1 Hz, 1H), 2.68 (d, J=0.9 Hz, 3H), 2.55 (s, 3H), 2.31-2.39 (m, 2H), 1.64-1.77 (m, 3H), 1.41-1.63 (m, 6H), 1.00-1.13 (m, 2H); MS (ESI) m/z 431.2 (M+H)$^+$.

Example 62

2-(4-chlorophenyl)-N-{5,7-dimethyl-3-[4-(trifluoromethyl)phenyl]pyrazolo[1,5-a]pyrimidin-2-yl}acetamide The title compound was prepared using the methods analogous to that described in Examples 1A-1D, substituting 1-iodo-4-(trifluoromethyl)benzene for 1-iodo-4-(trifluoromethoxy)benzene, acetylacetone for 3-(dimethylamino)acrylaldehyde, and 2-(4-chlorophenyl)acetyl chloride for 3,3-dimethylbutanoyl chloride. $^1$H NMR (400 MHz, DMSO-$d_6$/Deuterium Oxide) δ ppm 7.80-7.83 (m, 2H), 7.53-7.56 (m, 2H), 7.32-7.43 (m, 4H), 7.02 (d, J=0.9 Hz, 1H), 3.66-3.68 (bs, 2H), 2.68 (d, J=0.6 Hz, 3H), 2.55 (s, 3H); MS (ESI) m/z 459.0 (M+H)$^+$.

Example 63

3,3-dimethyl-N-{6-methyl-3-[3-(trifluoromethyl)phenyl]pyrazolo[1,5-a]pyrimidin-2-yl}butanamide The title compound was prepared using the methods analogous to that described in Examples 1A-1D, substituting 1-iodo-3-(trifluoromethyl)benzene for 1-iodo-4-(trifluoromethoxy)benzene, and 3-(dimethylamino)-2-methylacrylaldehyde for 3-(dimethylamino)acrylaldehyde. $^1$H NMR (400 MHz, DMSO-$d_6$/Deuterium Oxide) δ ppm 8.92 (dd, J=2.2, 1.1 Hz, 1H), 8.58 (d, J=2.1 Hz, 1H), 8.07-8.10 (m, 2H), 7.61-7.69 (m, 2H), 2.37 (d, J=1.1 Hz, 3H), 2.23 (s, 2H), 1.00 (s, 9H); MS (ESI) m/z 391.3 (M+H)$^+$.

Example 64

2-cyclopentyl-N-{3-[3-(trifluoromethyl)phenyl]pyrazolo[1,5-a]pyrimidin-2-yl}acetamide The title compound was prepared using the methods analogous to that described in Examples 1A-1D, substituting 1-iodo-3-(trifluoromethyl)benzene for 1-iodo-4-(trifluoromethoxy)benzene, and 2-cyclopentylacetyl chloride for 3,3-dimethylbutanoyl chloride. $^1$H NMR (400 MHz, DMSO-$d_6$/Deuterium Oxide) δ ppm 9.07 (dd, J=6.9, 1.7 Hz, 1H), 8.67 (dd, J=4.1, 1.7 Hz, 1H), 8.07-8.10 (m, 2H), 7.62-7.70 (m, 2H), 7.17 (dd, J=6.9, 4.1 Hz, 1H), 2.34 (d, J=7.4 Hz, 2H), 2.18 (p, J=7.3 Hz, 1H), 1.67-1.76 (m, 2H), 1.44-1.64 (m, 4H), 1.09-1.23 (m, 2H); MS (ESI) m/z 389.1 (M+H)$^+$.

Example 65

3-cyclohexyl-N-{7-methyl-3-[3-(trifluoromethyl)phenyl]pyrazolo[1,5-a]pyrimidin-2-yl}propanamide The title compound was prepared using the methods analogous to that described in Examples 1A-1D, substituting 1-iodo-3-(trifluoromethyl)benzene for 1-iodo-4-(trifluoromethoxy)benzene, 4-(dimethylamino)but-3-en-2-one for 3-(dimethylamino)acrylaldehyde, and 3-cyclohexylpropanoyl chloride for 3,3-dimethylbutanoyl chloride. $^1$H NMR (500 MHz, DMSO-$d_6$/Deuterium Oxide) δ ppm 8.57 (d, J=4.2 Hz, 1H), 8.09-8.13 (m, 1H), 8.05-8.09 (bs, 1H), 7.66 (dd, J=7.7 Hz, 1H), 7.61-7.64 (m, 1H), 7.13 (dd, J=4.2, 1.1 Hz, 1H), 2.74 (d, J=0.9 Hz, 3H), 2.33-2.37 (m, 2H), 1.62-1.68 (m, 5H), 1.43-1.47 (m, 2H), 1.08-1.26 (m, 4H), 0.82-0.91 (m, 2H); MS (ESI) m/z 431.2 (M+H)$^+$.

Example 66

2-(2,5-dimethoxyphenyl)-N-{7-methyl-3-[3-(trifluoromethyl)phenyl]pyrazolo[1,5-a]pyrimidin-2-yl}acetamide The title compound was prepared using the methods analogous to that described in Examples 1A-1D, substituting 1-iodo-3-(trifluoromethyl)benzene for 1-iodo-4-(trifluoromethoxy)benzene, 4-(dimethylamino)but-3-en-2-one for 3-(dimethylamino)acrylaldehyde, and 2-(2,5-dimethoxyphenyl)acetyl chloride for 3,3-dimethylbutanoyl chloride. MS (ESI) m/z 471.1 (M+H)$^+$.

Example 67

2-(4-fluorophenyl)-N-{7-methyl-3-[3-(trifluoromethyl)phenyl]pyrazolo[1,5-a]pyrimidin-2-yl}acetamide The title compound was prepared using the methods analogous to that described in Examples 1A-1D, substituting 1-iodo-3-(trifluoromethyl)benzene for 1-iodo-4-(trifluoromethoxy)benzene, 4-(dimethylamino)but-3-en-2-one for 3-(dimethylamino)acrylaldehyde, and 2-(4-fluorophenyl)acetyl chloride for 3,3-dimethylbutanoyl chloride. $^1$H NMR (500 MHz, DMSO-$d_6$/Deuterium Oxide) δ ppm 8.57 (d, J=4.3 Hz, 1H), 8.10-8.11 (bs, 1H), 7.89-7.92 (m, 1H), 7.57-7.60 (m, 1H), 7.49-7.53 (m, 1H), 7.30-7.38 (m, 2H), 7.13-7.18 (m, 3H), 3.69 (s, 2H), 2.74 (s, 3H); MS (ESI) m/z 429.1 (M+H)$^+$.

Example 68

N-[3-(3-chloro-4-methylphenyl)-7-methylpyrazolo[1,5-a]pyrimidin-2-yl]-3-cyclohexylpropanamide The title compound was prepared using the methods analogous to that described in Examples 1A-1D, substituting 4-bromo-2-chloro-1-methylbenzene for 1-iodo-4-(trifluoromethoxy)benzene, 4-(dimethylamino)but-3-en-2-one for 3-(dimethylamino)acrylaldehyde, and 3-cyclohexylpropanoyl chloride for 3,3-dimethylbutanoyl chloride. $^1$H NMR (400 MHz, DMSO-$d_6$/Deuterium Oxide) δ ppm 8.54 (d, J=4.2 Hz, 1H), 7.80-7.81 (bs, 1H), 7.67 (dd, J=7.9, 1.7 Hz, 1H), 7.38 (d, J=7.9 Hz, 1H), 7.10 (dd, J=4.2, 1.1 Hz, 1H), 2.72 (d, J=0.9 Hz, 3H), 2.35 (s, 3H), 2.32-2.36 (m, 2H), 1.57-1.75 (m, 5H), 1.43-1.54 (m, 2H), 1.08-1.27 (m, 4H), 0.80-0.96 (m, 2H); MS (ESI) m/z 411.1 [M+H]$^+$.

Example 69

N-[3-(3-chloro-4-methylphenyl)-7-methylpyrazolo[1,5-a]pyrimidin-2-yl]-2-(4-chlorophenyl)acetamide The title compound was prepared using the methods analogous to that described in Examples 1A-1D, substituting 4-bromo-2-chloro-1-methylbenzene for 1-iodo-4-(trifluoromethoxy)benzene, 4-(dimethylamino)but-3-en-2-one for 3-(dimethylamino)acrylaldehyde, and 2-(4-chlorophenyl)acetyl chloride for 3,3-dimethylbutanoyl chloride. $^1$H NMR (400 MHz, DMSO-$d_6$/Deuterium Oxide) δ ppm 8.54 (d, J=4.2 Hz, 1H), 7.77 (d, J=1.8 Hz, 1H), 7.48-7.53 (m, 1H), 7.29-7.44 (m, 4H), 7.21-7.26 (m, 1H), 7.11 (dd, J=4.3, 1.0 Hz, 1H), 3.70 (s, 2H), 2.72 (s, 3H), 2.33 (s, 3H); MS (ESI) m/z 425.0 [M+H]$^+$.

Example 70

N-[3-(4-fluorobenzyl)pyrazolo[1,5-a]pyrimidin-2-yl]-2-(4-methoxyphenyl)acetamide The title compound was prepared using the methods analogous to that described in Examples 5A-5D, substituting 3-(dimethylamino)acrylaldehyde for 3-(dimethylamino)-2-methylacrylaldehyde, and 2-(4-methoxyphenyl)acetyl chloride for 2-cyclopentylacetyl chloride. $^1$H NMR (500 MHz, DMSO-d$_6$/Deuterium Oxide) δ ppm 8.92 (dd, J=6.9, 1.7 Hz, 1H), 8.50 (dd, J=4.1, 1.7 Hz, 1H), 7.19-7.26 (m, 2H), 6.98-7.02 (m, 3H), 6.88-6.95 (m, 4H), 3.99-3.99 (bs, 2H), 3.75 (s, 3H), 3.56-3.56 (bs, 2H); MS (ESI) m/z 391.1 (M+H)$^+$.

Example 71

3-cyclopentyl-N-[3-(4-fluorobenzyl)-7-methylpyrazolo[1,5-a]pyrimidin-2-yl]propanamide The title compound was prepared using the methods analogous to that described in Examples 5A-5D, substituting 4-(dimethylamino)but-3-en-2-one for 3-(dimethylamino)-2-methylacrylaldehyde, and 3-cyclopentylpropanoyl chloride for 2-cyclopentylacetyl chloride. $^1$H NMR (400 MHz, DMSO-d$_6$/Deuterium Oxide) δ ppm 8.40 (d, J=4.2 Hz, 1H), 7.08-7.13 (m, 2H), 6.95-7.04 (m, 3H), 4.06-4.09 (bs, 2H), 2.67 (d, J=0.8 Hz, 3H), 2.27 (t, J=7.6 Hz, 2H), 1.38-1.75 (m, 9H), 1.00-1.07 (m, 2H); MS (ESI) m/z 381.1 (M+H)$^+$.

Example 72

N-[3-(3-chloro-4-methylphenyl)-6-methylpyrazolo[1,5-a]pyrimidin-2-yl]-2-(4-fluorophenyl)acetamide The title compound was prepared using the methods analogous to that described in Examples 1A-1D, substituting 4-bromo-2-chloro-1-methylbenzene for 1-iodo-4-(trifluoromethoxy)benzene, 3-(dimethylamino)-2-methylacrylaldehyde for 3-(dimethylamino)acrylaldehyde, and 2-(4-fluorophenyl)acetyl chloride for 3,3-dimethylbutanoyl chloride. $^1$H NMR (400 MHz, DMSO-d$_6$/Deuterium Oxide) δ ppm 8.89 (dd, J=2.2, 1.3 Hz, 1H), 8.55 (d, J=2.1 Hz, 1H), 7.77 (d, J=1.8 Hz, 1H), 7.50-7.53 (m, 1H), 7.31-7.41 (m, 2H), 7.25 (d, J=8.1 Hz, 1H), 7.12-7.21 (m, 2H), 3.70 (s, 2H), 2.36 (d, J=0.8 Hz, 3H), 2.33 (s, 3H); MS (ESI) m/z 409.1 [M+H]$^+$.

Example 73

N-[3-(3-chloro-4-methylphenyl)-6-methylpyrazolo[1,5-a]pyrimidin-2-yl]-2-(2,5-dimethoxyphenyl)acetamide The title compound was prepared using the methods analogous to that described in Examples 1A-1D, except substituting 4-bromo-2-chloro-1-methylbenzene for 1-iodo-4-(trifluoromethoxy)benzene, 3-(dimethylamino)-2-methylacrylaldehyde for 3-(dimethylamino)acrylaldehyde, and 2-(2,5-dimethoxyphenyl)acetyl chloride for 3,3-dimethylbutanoyl chloride. $^1$H NMR (400 MHz, DMSO-d$_6$/Deuterium Oxide) δ ppm 8.88-8.91 (bs, 1H), 8.55 (d, J=2.1 Hz, 1H), 7.86-7.87 (m, 1H), 7.62 (d, J=7.8 Hz, 1H), 7.32 (d, J=7.3 Hz, 1H), 6.87-6.97 (m, 1H), 6.76-6.86 (m, 2H), 2.36 (d, J=0.8 Hz, 3H), 2.35 (s, 3H); MS (ESI) m/z 451.1 [M+H]$^+$.

Example 74

N-[3-(3-chloro-4-methylphenyl)-6-methylpyrazolo[1,5-a]pyrimidin-2-yl]-3-phenylpropanamide The title compound was prepared using the methods analogous to that described in Examples 1A-1D, substituting 4-bromo-2-chloro-1-methylbenzene for 1-iodo-4-(trifluoromethoxy)benzene, 3-(dimethylamino)-2-methylacrylaldehyde for 3-(dimethylamino)acrylaldehyde, and 3-phenylpropanoyl chloride for 3,3-dimethylbutanoyl chloride. $^1$H NMR (400 MHz, DMSO-d$_6$/Deuterium Oxide) δ ppm 8.89 (dd, J=2.2, 1.1 Hz, 1H), 8.56 (d, J=2.1 Hz, 1H), 7.84 (d, J=1.7 Hz, 1H), 7.57 (dd, J=7.9, 1.8 Hz, 1H), 7.20-7.35 (m, 6H), 2.86-2.93 (m, 2H), 2.62-2.71 (m, 2H), 2.36 (d, J=1.1 Hz, 3H), 2.35 (s, 3H); MS (ESI) m/z 405.1 [M+H]$^+$.

Example 75

N-[3-(3-chloro-4-methylphenyl)pyrazolo[1,5-a]pyrimidin-2-yl]-3-cyclopentylpropanamide The title compound was prepared using the methods analogous to that described in Examples 1A-1D, substituting 4-bromo-2-chloro-1-methylbenzene for 1-iodo-4-(trifluoromethoxy)benzene, and 3-cyclopentylpropanoyl chloride for 3,3-dimethylbutanoyl chloride. $^1$H NMR (500 MHz, DMSO-d$_6$/Deuterium Oxide) δ ppm 9.04 (dd, J=6.9, 1.7 Hz, 1H), 8.64 (dd, J=4.1, 1.7 Hz, 1H), 7.78-7.79 (bs, 1H), 7.68 (dd, J=7.8, 1.8 Hz, 1H), 7.39 (d, J=7.9 Hz, 1H), 7.14 (dd, J=7.0, 4.1 Hz, 1H), 2.36 (s, 3H), 2.32-2.38 (m, 2H), 1.69-1.80 (m, 3H), 1.54-1.63 (m, 4H), 1.45-1.53 (m, 2H), 1.04-1.14 (m, 2H); MS (ESI) m/z 383.1 [M+H]$^+$.

Example 76

N-[3-(4-fluorobenzyl)-6-methylpyrazolo[1,5-a]pyrimidin-2-yl]-2-(4-methoxyphenyl)acetamide The title compound was prepared using the methods analogous to that described in Examples 5A-5D, substituting 2-(4-methoxyphenyl)acetyl chloride for 2-cyclopentylacetyl chloride. $^1$H NMR (400 MHz, DMSO-d$_6$/Deuterium Oxide) δ ppm 8.75-8.78 (m, 1H), 8.40 (d, J=2.1 Hz, 1H), 7.19-7.26 (m, 2H), 6.96-7.02 (m, 2H), 6.91-6.96 (m, 2H), 6.85-6.91 (m, 2H), 3.96 (s, 2H), 3.74 (s, 3H), 3.54 (s, 2H), 2.31 (d, J=0.9 Hz, 3H); MS (ESI) m/z 405.3 (M+H)$^+$.

Example 77

3-cyclohexyl-N-[3-(4-fluorobenzyl)-6-methylpyrazolo[1,5-a]pyrimidin-2-yl]propanamide The title compound was prepared using the methods analogous to that described in Examples 5A-5D, substituting 3-cyclohexylpropanoyl chloride for 2-cyclopentylacetyl chloride. $^1$H NMR (400 MHz, DMSO-d$_6$/Deuterium Oxide) δ ppm 8.77 (dd, J=2.0, 1.1 Hz, 1H), 8.40 (d, J=2.1 Hz, 1H), 7.10-7.14 (m, 2H), 6.97-7.04 (m, 2H), 4.03 (s, 2H), 2.31 (d, J=0.8 Hz, 3H), 2.26 (t, J=7.2 Hz, 2H), 1.54-1.72 (m, 5H), 1.35-1.47 (m, 2H), 1.03-1.23 (m, 4H), 0.76-0.92 (m, 2H); MS (ESI) m/z 395.1 (M+H)$^+$.

Example 78

N-{5,7-dimethyl-3-[3-(trifluoromethyl)phenyl]pyrazolo[1,5-a]pyrimidin-2-yl}-3-phenylpropanamide The title compound was prepared using the methods analogous to that described in Examples 1A-1D, substituting 1-iodo-3-(trifluoromethyl)benzene for 1-iodo-4-(trifluoromethoxy)benzene, acetylacetone for 3-(dimethylamino)acrylaldehyde, and 3-phenylpropanoyl chloride for 3,3-dimethylbutanoyl chloride. $^1$H NMR (500 MHz, DMSO-d$_6$/Deuterium Oxide) δ ppm 8.12-8.13 (bs, 1H), 8.02-8.04 (m, 1H), 7.59-7.63 (m, 2H), 7.27-7.35 (m, 2H), 7.17-7.27 (m, 3H), 7.02 (s, 1H), 2.87 (t, J=7.4 Hz, 2H), 2.68 (d, J=0.6 Hz, 3H), 2.64-2.69 (m, 2H), 2.56 (s, 3H); MS (ESI) m/z 439.3 (M+H)$^+$.

Example 79

3-cyclohexyl-N-{7-methyl-3-[4-(trifluoromethyl)phenyl]pyrazolo[1,5-a]pyrimidin-2-yl}propanamide The title compound was prepared using the methods analogous to that described in Examples 1A-1D, substituting 1-iodo-4-(trifluoromethyl)benzene for 1-iodo-4-(trifluoromethoxy)benzene, 4-(dimethylamino)but-3-en-2-one for 3-(dimethylamino)acrylaldehyde, and 3-cyclohexylpropanoyl chloride for 3,3-dimethylbutanoyl chloride. $^1$H NMR (500 MHz, DMSO-$d_6$/Deuterium Oxide) δ ppm 8.56 (d, J=4.3 Hz, 1H), 7.98-8.00 (m, 2H), 7.75-7.77 (m, 2H), 7.13 (dd, J=4.3, 1.1 Hz, 1H), 2.74 (s, 3H), 2.36-2.40 (m, 2H), 1.60-1.72 (m, 5H), 1.43-1.48 (m, 2H), 1.05-1.18 (m, 4H), 0.81-0.87 (m, 2H); MS (ESI) m/z 431.1 (M+H)$^+$.

Example 80

2-(4-methoxyphenyl)-N-{7-methyl-3-[4-(trifluoromethyl)phenyl]pyrazolo[1,5-a]pyrimidin-2-yl}acetamide The title compound was prepared using the methods analogous to that described in Examples 1A-1D, substituting 1-iodo-4-(trifluoromethyl)benzene for 1-iodo-4-(trifluoromethoxy)benzene, 4-(dimethylamino)but-3-en-2-one for 3-(dimethylamino)acrylaldehyde, and 2-(4-methoxyphenyl)acetyl chloride for 3,3-dimethylbutanoyl chloride. $^1$H NMR (500 MHz, DMSO-$d_6$/Deuterium Oxide) δ ppm 8.56 (d, J=4.3 Hz, 1H), 7.83-7.85 (m, 2H), 7.53-7.56 (m, 2H), 7.25-7.29 (m, 2H), 7.13 (dd, J=4.3, 0.9 Hz, 1H), 6.90-6.93 (m, 2H), 3.76 (s, 3H), 3.61 (s, 2H), 2.74 (s, 3H); MS (ESI) m/z 441.1 (M+H)$^+$.

Example 81

2-(4-chlorophenyl)-N-[3-(3-fluorophenyl)pyrazolo[1,5-a]pyrimidin-2-yl]acetamide

The title compound was prepared using the methods analogous to that described in Examples 1A-1D, substituting 1-fluoro-3-iodobenzene for 1-iodo-4-(trifluoromethoxy)benzene, and 2-(4-chlorophenyl)acetyl chloride for 3,3-dimethylbutanoyl chloride. $^1$H NMR (400 MHz, DMSO-$d_6$/Deuterium Oxide) δ ppm 9.06 (dd, J=6.9, 1.7 Hz, 1H), 8.66 (dd, J=4.1, 1.7 Hz, 1H), 7.48-7.54 (m, 2H), 7.30-7.45 (m, 5H), 7.16 (dd, J=7.0, 4.1 Hz, 1H), 7.04-7.10 (m, 1H), 3.71 (s, 2H); MS (ESI) m/z 381.0 (M+H)$^+$.

Example 82

2-(4-fluorophenyl)-N-[3-(3-fluorophenyl)pyrazolo[1,5-a]pyrimidin-2-yl]acetamide

The title compound was prepared using the methods analogous to that described in Examples 1A-1D, substituting 1-fluoro-3-iodobenzene for 1-iodo-4-(trifluoromethoxy)benzene, and 2-(4-fluorophenyl)acetyl chloride for 3,3-dimethylbutanoyl chloride. $^1$H NMR (500 MHz, Chloroform-$d_1$) δ ppm 8.68 (d, J=6.9 Hz, 1H), 8.51 (dd, J=4.0, 1.4 Hz, 1H), 7.49-7.50 (bs, 1H), 7.27-7.36 (m, 3H), 7.12-7.23 (m, 2H), 7.04-7.12 (m, 2H), 7.00 (ddd, J=8.4, 2.3 Hz, 1H), 6.86 (dd, J=6.9, 4.0 Hz, 1H), 3.78-3.90 (bs, 2H); MS (ESI) m/z 365.1 (M+H)$^+$.

Example 83

2-cyclopentyl-N-[3-(3-fluorophenyl)-6-methylpyrazolo[1,5-a]pyrimidin-2-yl]acetamide The title compound was prepared using the methods analogous to that described in Examples 1A-1D, substituting 1-fluoro-3-iodobenzene for 1-iodo-4-(trifluoromethoxy)benzene, 3-(dimethylamino)-2-methylacrylaldehyde for 3-(dimethylamino)acrylaldehyde, and 2-cyclopentylacetyl chloride for 3,3-dimethylbutanoyl chloride. $^1$H NMR (400 MHz, DMSO-$d_6$/Deuterium Oxide) δ ppm 8.90 (dd, J=2.2, 1.1 Hz, 1H), 8.57 (d, J=2.1 Hz, 1H), 7.67 (d, J=7.8 Hz, 1H), 7.56-7.60 (m, 1H), 7.42-7.49 (m, 1H), 7.06-7.12 (m, 1H), 2.37 (d, J=0.9 Hz, 3H), 2.32-2.36 (m, 2H), 2.21 (p, J=7.3 Hz, 1H), 1.69-1.76 (m, 2H), 1.45-1.66 (m, 4H), 1.09-1.23 (m, 2H); MS (ESI) m/z 353.1 (M+H)$^+$.

Example 84

2-(4-fluorophenyl)-N-[3-(3-fluorophenyl)-6-methylpyrazolo[1,5-a]pyrimidin-2-yl]acetamide The title compound was prepared using the methods analogous to that described in Examples 1A-1D, substituting 1-fluoro-3-iodobenzene for 1-iodo-4-(trifluoromethoxy)benzene, 3-(dimethylamino)-2-methylacrylaldehyde for 3-(dimethylamino)acrylaldehyde, and 2-(4-fluorophenyl)acetyl chloride for 3,3-dimethylbutanoyl chloride. $^1$H NMR (400 MHz, DMSO-$d_6$/Deuterium Oxide) δ ppm 8.90 (dd, J=2.0, 1.1 Hz, 1H), 8.57 (d, J=2.1 Hz, 1H), 7.48-7.53 (m, 2H), 7.25-7.37 (m, 3H), 7.13-7.19 (m, 2H), 7.02-7.07 (m, 1H), 3.68 (s, 2H), 2.36 (d, J=1.1 Hz, 3H); MS (ESI) m/z 379.1 (M+H)$^+$.

Example 85

N-[3-(3-fluorophenyl)-5,7-dimethylpyrazolo[1,5-a]pyrimidin-2-yl]-3-phenylpropanamide The title compound was prepared using the methods analogous to that described in Examples 1A-1D, substituting 1-fluoro-3-iodobenzene for 1-iodo-4-(trifluoromethoxy)benzene, acetylacetone for 3-(dimethylamino)acrylaldehyde, and 3-phenylpropanoyl chloride for 3,3-dimethylbutanoyl chloride. $^1$H NMR (500 MHz, DMSO-$d_6$/Deuterium Oxide) δ ppm 7.60-7.63 (m, 1H), 7.54-7.58 (m, 1H), 7.36-7.43 (m, 1H), 7.18-7.34 (m, 5H), 7.07 (ddd, J=8.6, 2.5 Hz, 1H), 7.00 (d, J=0.8 Hz, 1H), 2.85-2.94 (m, 2H), 2.65-2.72 (m, 2H), 2.67 (d, J=0.9 Hz, 3H), 2.55 (s, 3H); MS (ESI) m/z 389.1 (M+H)$^+$.

Example 86

2-cyclohexyl-N-[3-(3-fluorophenyl)-5,7-dimethylpyrazolo[1,5-a]pyrimidin-2-yl]acetamide The title compound was prepared using the methods analogous to that described in Examples 1A-1D, substituting 1-fluoro-3-iodobenzene for 1-iodo-4-(trifluoromethoxy)benzene, acetylacetone for 3-(dimethylamino)acrylaldehyde, and 2-cyclohexylacetyl chloride for 3,3-dimethylbutanoyl chloride. $^1$H NMR (500 MHz, DMSO-$d_6$/Deuterium Oxide) δ ppm 7.66 (d, J=7.6 Hz, 1H), 7.55-7.60 (m, 1H), 7.41-7.46 (m, 1H), 7.05-7.10 (m, 1H), 7.00 (d, J=1.1 Hz, 1H), 2.67 (d, J=0.9 Hz, 3H), 2.55 (s, 3H), 2.22 (d, J=5.3 Hz, 2H), 1.55-1.78 (m, 6H), 1.09-1.25 (m, 3H), 0.90-1.03 (m, 2H); MS (ESI) m/z 381.3 (M+H)$^+$.

Example 87

2-cyclopentyl-N-{3-[3-fluoro-4-(trifluoromethyl)phenyl]-6-methylpyrazolo[1,5-a]pyrimidin-2-yl}acetamide The title compound was prepared using the methods analogous to that described in Examples 1A-1D, substituting 4-bromo-2-fluoro-1-(trifluoromethyl)benzene for 1-iodo-4-(trifluoromethoxy)benzene, 3-(dimethylamino)-2-methylacrylaldehyde for 3-(dimethylamino)acrylaldehyde, and 2-cyclopentylacetyl chloride for 3,3-dimethylbutanoyl chloride. $^1$H NMR (400 MHz, DMSO-d$_6$) δ ppm 1.06-1.84 (m, 8H) 2.12-2.27 (m, 1H) 2.35-2.41 (m, 5H) 7.66-8.07 (m, 3H) 8.63 (d, J=2.06 Hz, 1H) 9.02 (s, 1H) 10.35 (s, 1H); MS (ESI) m/z 421.2 (M+H)$^+$.

Example 88

3-cyclopentyl-N-{3-[3-fluoro-4-(trifluoromethyl)phenyl]pyrazolo[1,5-a]pyrimidin-2-yl}propanamide The title compound was prepared using the methods analogous to that described in Examples 1A-1D, substituting 4-bromo-2-fluoro-1-(trifluoromethyl)benzene for 1-iodo-4-(trifluoromethoxy)benzene, and 3-cyclopentylpropanoyl chloride for 3,3-dimethylbutanoyl chloride. $^1$H NMR (400 MHz, DMSO-d$_6$) δ ppm 0.87-1.88 (m, 11H) 2.39 (t, J=7.48 Hz, 2H) 7.22 (dd, J=6.99, 4.17 Hz, 1H) 7.67-8.05 (m, 3H) 8.71 (dd, J=4.17, 1.68 Hz, 1H) 9.16 (dd, J=6.94, 1.63 Hz, 1H) 10.42 (s, 1H). MS (ESI) m/z 421.2 (M+H)$^+$.

Example 89

3-cyclohexyl-N-(3-phenylpyrazolo[1,5-a]pyrimidin-2-yl)propanamide

The title compound was prepared using the methods analogous to that described in Examples 1A-1D, substituting iodobenzene for 1-iodo-4-(trifluoromethoxy)benzene, and 3-cyclohexylpropanoyl chloride for 3,3-dimethylbutanoyl chloride. $^1$H NMR (400 MHz, DMSO-d$_6$/Deuterium Oxide) δ ppm 9.03 (dd, J=6.9, 1.7 Hz, 1H), 8.61 (dd, J=4.0, 1.7 Hz, 1H), 7.73-7.80 (m, 2H), 7.41-7.45 (m, 2H), 7.27-7.32 (m, 1H), 7.12 (dd, J=6.9, 4.1 Hz, 1H), 2.29-2.40 (m, 2H), 1.56-1.76 (m, 5H), 1.41-1.52 (m, 2H), 1.05-1.28 (m, 4H), 0.78-0.94 (m, 2H); MS (ESI) m/z 349.1 (M+H)$^+$.

Example 90

3-phenyl-N-(3-phenylpyrazolo[1,5-a]pyrimidin-2-yl)propanamide

The title compound was prepared using the methods analogous to that described in Examples 1A-1D, substituting iodobenzene for 1-iodo-4-(trifluoromethoxy)benzene, and 3-phenylpropanoyl chloride for 3,3-dimethylbutanoyl chloride. $^1$H NMR (400 MHz, DMSO-d$_6$/Deuterium Oxide) δ ppm 9.03 (dd, J=6.9, 1.7 Hz, 1H), 8.61 (dd, J=4.0, 1.7 Hz, 1H), 7.68-7.72 (m, 2H), 7.36-7.42 (m, 2H), 7.19-7.34 (m, 6H), 7.12 (dd, J=7.0, 4.1 Hz, 1H), 2.89 (t, J=7.0 Hz, 2H), 2.67 (t, J=7.0 Hz, 2H); MS (ESI) m/z 343.1 (M+H)$^+$.

Example 91

N-(7-methyl-3-phenylpyrazolo[1,5-a]pyrimidin-2-yl)-2-phenylacetamide

The title compound was prepared using the methods analogous to that described in Examples 1A-1D, substituting iodobenzene for 1-iodo-4-(trifluoromethoxy)benzene, 4-(dimethylamino)but-3-en-2-one for 3-(dimethylamino)acrylaldehyde, and 2-phenylacetyl chloride for 3,3-dimethylbutanoyl chloride. $^1$H NMR (400 MHz, DMSO-d$_6$/Deuterium Oxide) δ ppm 8.51 (d, J=4.2 Hz, 1H), 7.65-7.72 (m, 2H), 7.16-7.36 (m, 8H), 7.08 (dd, J=4.3, 0.9 Hz, 1H), 3.68 (s, 2H), 2.72 (d, J=0.8 Hz, 3H); MS (ESI) m/z 343.3 (M+H)$^+$.

Example 92

3,3-dimethyl-N-(6-methyl-3-phenylpyrazolo[1,5-a]pyrimidin-2-yl)butanamide

The title compound was prepared using the methods analogous to that described in Examples 1A-1D, substituting iodobenzene for 1-iodo-4-(trifluoromethoxy)benzene, and 3-(dimethylamino)-2-methylacrylaldehyde for 3-(dimethylamino)acrylaldehyde. $^1$H NMR (400 MHz, DMSO-d$_6$/Deuterium Oxide) δ ppm 8.88 (dd, J=2.2, 1.1 Hz, 1H), 8.52 (d, J=2.1 Hz, 1H), 7.76-7.79 (m, 2H), 7.39-7.43 (m, 2H), 7.25-7.30 (m, 1H), 2.36 (d, J=1.1 Hz, 3H), 2.21-2.22 (bs, 2H), 1.01 (s, 9H); MS (ESI) m/z 323.1 (M+H)$^+$.

Example 93

2-(4-chlorophenyl)-N-(6-methyl-3-phenylpyrazolo[1,5-a]pyrimidin-2-yl)acetamide

The title compound was prepared using the methods analogous to that described in Examples 1A-1D, substituting iodobenzene for 1-iodo-4-(trifluoromethoxy)benzene, 3-(dimethylamino)-2-methylacrylaldehyde for 3-(dimethylamino)acrylaldehyde, and 2-(4-chlorophenyl)acetyl chloride for 3,3-dimethylbutanoyl chloride. $^1$H NMR (400 MHz, DMSO-d$_6$/Deuterium Oxide) δ ppm 8.87-8.89 (m, 1H), 8.53 (d, J=2.1 Hz, 1H), 7.65-7.68 (m, 2H), 7.21-7.43 (m, 7H), 2.36 (d, J=0.9 Hz, 3H); MS (ESI) m/z 377.0 (M+H)$^+$.

Example 94

2-cyclohexyl-N-(5,7-dimethyl-3-phenylpyrazolo[1,5-a]pyrimidin-2-yl)acetamide

The title compound was prepared using the methods analogous to that described in Examples 1A-1D, substituting iodobenzene for 1-iodo-4-(trifluoromethoxy)benzene, acetylacetone for 3-(dimethylamino)acrylaldehyde, and 2-cyclohexylacetyl chloride for 3,3-dimethylbutanoyl chloride. $^1$H NMR (400 MHz, DMSO-d$_6$/Deuterium Oxide) δ ppm 7.74-7.77 (m, 2H), 7.37-7.42 (m, 2H), 7.24-7.28 (m, 1H), 6.96 (d, J=1.1 Hz, 1H), 2.66 (d, J=0.9 Hz, 3H), 2.53 (s, 3H), 2.19 (d, J=5.6 Hz, 2H), 1.54-1.78 (m, 6H), 1.06-1.29 (m, 3H), 0.86-1.04 (m, 2H); MS (ESI) m/z 363.1 (M+H)$^+$.

Example 95

3-cyclopentyl-N-(5,7-dimethyl-3-phenylpyrazolo[1,5-a]pyrimidin-2-yl)propanamide

The title compound was prepared using the methods described in Examples 1A-1D, substituting iodobenzene for 1-iodo-4-(trifluoromethoxy)benzene, acetylacetone for 3-(dimethylamino)acrylaldehyde, and 3-cyclopentylpropanoyl chloride for 3,3-dimethylbutanoyl chloride. $^1$H NMR (400 MHz, DMSO-d$_6$/Deuterium Oxide) δ ppm 7.74-7.77 (m, 2H), 7.37-7.43 (m, 2H), 7.24-7.29 (m, 1H), 6.97 (d, J=1.1 Hz, 1H), 2.66 (d, J=0.9 Hz, 3H), 2.53 (s, 3H), 2.27-2.38 (m, 2H), 1.66-1.80 (m, 3H), 1.46-1.60 (m, 6H), 0.96-1.15 (m, 2H); MS (ESI) m/z 363.4 (M+H)+.

Example 96

N-(5,7-dimethyl-3-phenylpyrazolo[1,5-a]pyrimidin-2-yl)-2-(4-fluorophenyl)acetamide The title compound was prepared using the methods analogous to that described in Examples 1A-1D, substituting iodobenzene for 1-iodo-4-(trifluoromethoxy)benzene, acetylacetone for 3-(dimethylamino)acrylaldehyde, and 2-(4-fluorophenyl)acetyl chloride for 3,3-dimethylbutanoyl chloride. H NMR (400 MHz, DMSO-$d_6$/Deuterium Oxide) δ ppm 7.65-7.68 (m, 2H), 7.14-7.38 (m, 7H), 6.93-6.99 (m, 1H), 3.65 (s, 2H), 2.66 (d, J=0.6 Hz, 3H), 2.53 (s, 3H); MS (ESI) m/z 375.1 (M+H)+.

Example 97

N-[3-(3-fluorophenyl)-7-methylpyrazolo[1,5-a]pyrimidin-2-yl]-2-(4-methoxyphenyl)acetamide The title compound was prepared using the methods analogous to that described in Examples 1A-1D, substituting 1-fluoro-3-iodobenzene for 1-iodo-4-(trifluoromethoxy)benzene, 4-(dimethylamino)but-3-en-2-one for 3-(dimethylamino)acrylaldehyde, and 2-(4-methoxyphenyl)acetyl chloride for 3,3-dimethylbutanoyl chloride. $^1$H NMR (500 MHz, DMSO-$d_6$/Deuterium Oxide) δ ppm 8.55 (d, J=4.2 Hz, 1H), 7.53-7.57 (m, 1H), 7.49-7.53 (m, 1H), 7.19-7.35 (m, 3H), 7.12 (dd, J=4.3, 0.8 Hz, 1H), 7.05 (ddd, J=8.5, 2.3 Hz, 1H), 6.88-6.93 (m, 2H), 3.75 (s, 3H), 3.61 (s, 2H), 2.73 (s, 3H); MS (ESI) m/z 391.1 (M+H)+.

Example 98

2-(pyridin-3-yl)-N-{3-[4-(trifluoromethoxy)phenyl]pyrazolo[1,5-a]pyrimidin-2-yl}acetamide 3-Pyridylacetic acid hydrochloride (41.6 mg, 0.239 mmol) was suspended in dichloromethane (3.0 mL). Oxalyl chloride (24 μL, 0.28 mmol) and a drop of dimethylformamide were added and the mixture was stirred at ambient temperature for 90 minutes. The reaction mixture was concentrated under vacuum. To this residue was added a solution of the product from Example 1C (59 mg, 0.2 mmol) in pyridine (2.0 mL). The mixture was stirred at ambient temperature for 1 hour and then at 40° C. for 1 hour. The reaction mixture was concentrated under vacuum and purified by reverse-phase HPLC [Waters XBridge™ RP18 column, 5 μm, 30×100 mm, flow rate 40 mL/minute, 30-100% gradient of methanol in buffer (0.1 M aqueous ammonium bicarbonate, adjusted to pH 10 with ammonium hydroxide)] to afford 24 mg (29%) of the title compound. $^1$H NMR (400 MHz, CD$_3$OD) δ ppm 8.86 (d, J=5.8 Hz, 1H), 8.52-8.59 (m, 2H), 8.44-8.49 (m, 1H), 7.79-7.89 (m, 1H), 7.71-7.74 (m, 2H), 7.33-7.44 (m, 1H), 7.20-7.23 (m, 2H), 7.07 (dd, J=7.0, 4.1 Hz, 1H), 3.81 (s, 2H); MS (ESI) m/z 414 (M+H)+.

Example 99

1-[3-(4-chlorophenyl)pyrazolo[1,5-a]pyrimidin-2-yl]-3-(cyclohexylmethyl)urea

Example 99A 3-(4-chlorophenyl)pyrazolo[1,5-a]pyrimidin-2-amine

The title compound was prepared using the methods analogous to that described in Examples 1A-1C, substituting 1-chloro-4-iodobenzene for 1-iodo-4-(trifluoromethoxy)benzene. MS (APCI) m/z 245 [M+H]+.

Example 99B

Cyclohexanemethyl isocyanate (41 μL, 0.28 mmol) was added to a solution of the product from Example 99A (58 mg, 0.24 mmol) in pyridine (2.0 mL) and stirred at 45° C. for 66 h. The reaction mixture was concentrated under vacuum and purified by reverse-phase HPLC [Waters XBridge™ RP18 column, 5 μm, 30×100 mm, flow rate 40 mL/minute, 30-100% gradient of methanol in buffer (0.1 M aqueous ammonium bicarbonate, adjusted to pH 10 with ammonium hydroxide)] to afford 53 mg (58.2%) of the title compound. $^1$H NMR (400 MHz, CDCl$_3$) δ ppm 8.51 (dd, J=6.8, 1.8 Hz, 1H), 8.46 (dd, J=4.1, 1.8 Hz, 1H), 8.16-8.23 (m, 1H), 7.54-7.57 (m, 2H), 7.45-7.48 (m, 2H), 6.87 (s, 1H), 6.80 (dd, J=6.9, 4.1 Hz, 1H), 3.26 (t, J=6.3 Hz, 2H), 1.65-1.88 (m, 5H), 1.53-1.65 (m, 1H), 1.14-1.35 (m, 3H), 1.03 (qd, J=12.1, 3.0 Hz, 2H); MS (ESI) m/z 384 (M+H)+; Anal. calculated for C$_{20}$H$_{22}$ClN$_5$O: C, 62.47; H, 5.80; N, 18.17. Found C, 62.27; H, 5.53; N, 18.30.

Example 100

N-[3-(4-chlorophenyl)pyrazolo[1,5-a]pyrimidin-2-yl]-2-(pyridin-2-yl)acetamide

2-Pyridylacetic acid hydrochloride (44 mg, 0.25 mmol) and the product from Example 99A (62 mg, 0.25 mmol) were processed as described in Example 98 to afford 41 mg (45%) of the title compound. $^1$H NMR (400 MHz, CD$_3$OD) δ ppm 8.85 (dd, J=7.0, 1.7 Hz, 1H), 8.55 (dd, J=4.1, 1.7 Hz, 1H), 8.47-8.53 (m, 1H), 7.77-7.86 (m, 1H), 7.68-7.71 (m, 2H), 7.40-7.48 (m, 1H), 7.31-7.40 (m, 3H), 7.05 (dd, J=7.0, 4.1 Hz, 1H), 3.97 (s, 2H); MS (ESI) m/z 364 (M+H)+; Anal. calculated for C$_{19}$H$_{14}$ClN$_5$O: C, 62.73; H, 3.88; N, 19.25. Found C, 62.65; H, 3.65; N, 19.19.

Example 101

N-[3-(4-chlorophenyl)pyrazolo[1,5-a]pyrimidin-2-yl]-2-(pyridin-3-yl)acetamide

3-Pyridylacetic acid hydrochloride and the product from Example 99A were processed using method analogous to that described in Example 98 to afford the title compound. $^1$H NMR (400 MHz, CD$_3$OD) δ ppm 8.85 (dd, J=7.0, 1.8 Hz, 1H), 8.55 (dd, J=4.1, 1.8 Hz, 1H), 8.52-8.55 (m, 1H), 8.46-8.50 (m, 1H), 7.78-7.89 (m, 1H), 7.60-7.64 (m, 2H), 7.37-7.45 (m, 1H), 7.29-7.32 (m, 2H), 7.06 (dd, J=7.0, 4.1 Hz, 1H), 3.81 (s, 2H); MS (ESI) m/z 364 (M+H)+; Anal. calculated for C$_{19}$H$_{14}$ClN$_5$O.0.35H$_2$O: C, 61.66; H, 4.00; N, 18.92. Found C, 61.40; H, 3.70; N, 18.77.

Example 102

N-[3-(4-chlorophenyl)pyrazolo[1,5-a]pyrimidin-2-yl]-2-(pyridin-4-yl)acetamide

4-Pyridylacetic acid hydrochloride and the product from Example 99A were processed using method analogous to that described in Example 98 to afford the title compound. $^1$H NMR (400 MHz, CD$_3$OD) δ ppm 8.86 (dd, J=7.1, 1.6 Hz, 1H), 8.56 (dd, J=4.1, 1.8 Hz, 1H), 8.45-8.53 (m, 2H), 7.57-7.66 (m, 2H), 7.37-7.48 (m, 2H), 7.26-7.35 (m, 2H), 7.07 (dd, J=7.0, 4.1 Hz, 1H), 3.82 (s, 2H); MS (ESI) m/z 364 (M+H)+;

Anal. calculated for C$_{19}$H$_{14}$ClN$_5$O.0.25H$_2$O: C, 61.69; H, 3.97; N, 18.68. Found C, 61.59; H, 3.61; N, 18.68.

Example 103

1-[3-(4-chlorophenyl)pyrazolo[1,5-a]pyrimidin-2-yl]-3-(tetrahydro-2H-pyran-4-ylmethyl)urea 4-(Isocyanatomethyl)tetrahydropyran (Maybridge) and the product from Example 99A were processed using method analogous to that described in Example 99B to afford the title compound. $^1$H NMR (400 MHz, CDCl$_3$) δ ppm 8.51 (dd, J=6.9, 1.8 Hz, 1H), 8.47 (dd, J=4.1, 1.8 Hz, 1H), 8.21-8.31 (m, 1H), 7.54-7.56 (m, 2H), 7.46-7.49 (m, 2H), 6.89-6.90 (bs, 1H), 6.81 (dd, J=6.9, 4.1 Hz, 1H), 4.01 (dd, J=11.1, 3.6 Hz, 2H), 3.41 (td, J=11.7, 1.8 Hz, 2H), 3.33 (t, J=6.3 Hz, 2H), 1.84-1.95 (m, 1H), 1.69-1.75 (m, 2H), 1.42 (qd, J=12.3, 4.5 Hz, 2H); MS (ESI) m/z 386 (M+H)$^+$; Anal. calculated for C$_{19}$H$_{20}$ClN$_5$O$_2$: C, 59.14; H, 5.22; N, 18.15; Cl, 9.19. Found C, 58.96; H, 5.13; N, 17.99; Cl, 9.39.

Example 104

N-[3-(4-chlorophenyl)pyrazolo[1,5-a]pyrimidin-2-yl]-2-(2-hydroxyphenyl)acetamide The product from Example 99A (100 mg, 0.41 mmol), 2-hydroxyphenylacetic acid (124 mg, 0.82 mmol), 1-(3-dimethylaminopropyl)-3-ethylcarbodiimide hydrochloride (157 mg, 0.82 mmol), 1-hydroxybenzotriazole hydrate (100 mg, 0.65 mmol) were combined with pyridine (8 mL) and stirred at 35° C. for 18 hours. The reaction mixture was concentrated under vacuum and purified by reverse-phase HPLC [Waters XBridge™ RP18 column, 5 μm, 30×100 mm, flow rate 40 mL/minute, 5-95% gradient of acetonitrile in buffer (0.1 M aqueous ammonium bicarbonate, adjusted to pH 10 with ammonium hydroxide)] to afford 30 mg (19%) of the title compound. $^1$H NMR (400 MHz, DMSO-d$_6$) δ ppm 10.28-10.56 (bs, 1H), 9.09 (dd, J=6.9, 1.7 Hz, 1H), 8.62 (dd, J=4.1, 1.7 Hz, 1H), 7.70-7.73 (m, 2H), 7.30-7.34 (m, 2H), 7.11-7.16 (m, 2H), 6.72-6.81 (m, 2H), 6.65-6.72 (m, 1H), 3.57 (s, 2H); MS (ESI) m/z 379 (M+H)$^+$; Anal. calculated for C$_{20}$H$_{15}$ClN$_4$O$_2$.0.35H$_2$O: C, 62.37; H, 4.11; N, 14.55. Found C, 62.16; H, 3.87; N, 14.49.

Example 105

N-(3-tert-butylpyrazolo[1,5-a]pyrimidin-2-yl)-3-cyclopentylpropanamide

Example 105A 4-tert-butyl-1H-pyrazole-3,5-diamine

A mixture of tert-butylmalononitrile (5.01 g, 41.0 mmol) and hydrazine monohydrate (10.0 mL, 205 mmol) in 1-butanol (40 mL) was heated to reflux and stirred overnight (19 hours). The mixture was cooled to ambient temperature. Concentration afforded 6.33 g (100%) of the title compound. MS (DCI) m/z 155 (M+H)$^+$.

Example 105B 3-tert-butylpyrazolo[1,5-a]pyrimidin-2-amine

A mixture from Example 105A (2.61 g, 16.9 mmol), 3-dimethylaminoacrylaldehyde (2.0 mL, 20.0 mmol) and acetic acid (25 μL, 0.44 mmol) in ethanol (18 mL) was heated by microwave to 150° C. for 30 minutes. The mixture was cooled to ambient temperature and concentrated. Purification by silica gel chromatography (EtOAc, R$_f$=0.39) afforded 2.34 g (43%) of the title compound. MS (DCI) m/z 191 (M+H)$^+$.

Example 105C

N-(3-tert-butylpyrazolo[1,5-a]pyrimidin-2-yl)-3-cyclopentylpropanamide

A mixture from Example 105B (71.2 mg, 0.37 mmol) and 3-cyclopentylpropionyl chloride (94.4 mg, 0.59 mmol) in pyridine (2 mL) was stirred at ambient temperature for 5 h. The mixture was concentrated. Purification by reverse phase HPLC afforded 90.3 mg (77%) of the title compound. $^1$H NMR (300 MHz, DMSO-d$_6$): δ ppm 1.04-1.15 (m, 2H), 1.44-1.81 (m, 18H), 2.27-2.31 (m, 2H), 6.99 (dd, J=7.0, 3.9 Hz, 1H), 8.48 (dd, J=3.9, 1.9 Hz, 1H), 8.92 (dd, J=7.1, 1.7 Hz, 1H), 9.67 (br s, 1H); MS (DCI) m/z 315 (M+H)$^+$.

Example 106

N-(3-tert-butylpyrazolo[1,5-a]pyrimidin-2-yl)-3,3-dimethylbutanamide

The product from Example 105B and 3,3-dimethylbutanoyl chloride were processed using the method analogous to that described in Example 105C to afford the title compound. $^1$H NMR (300 MHz, DMSO-d$_6$): δ ppm 1.05 (s, 9H), 1.45 (s, 9H), 2.20 (s, 2H), 6.99 (dd, J=7.1, 4.1 Hz, 1H), 8.47 (dd, J=4.1, 1.7 Hz, 1H), 8.94 (dd, J=7.0, 1.9 Hz, 1H), 9.59 (br s, 1H); MS (DCI) m/z 289 (M+H)$^+$.

Example 107

2-(adamantan-1-yl)-N-(3-tert-butylpyrazolo[1,5-a]pyrimidin-2-yl)acetamide

The product from Example 105B and 1-adamantylacetyl chloride were processed using the method analogous to that described in Example 105C to afford the title compound. $^1$H NMR (300 MHz, DMSO-d$_6$): δ ppm 1.45 (s, 9H), 1.59-1.67 (m, 12H), 1.95 (br s, 3H), 2.06 (s, 2H), 6.98 (dd, J=6.8, 4.1 Hz, 1H), 8.47 (dd, J=4.1, 1.7 Hz, 1H), 8.95 (dd, J=7.0, 1.9 Hz, 1H), 9.56 (s, 1H); MS (DCI) m/z 367 (M+H)$^+$.

Example 108

1-[3-(4-chlorophenyl)pyrazolo[1,5-a]pyrimidin-2-yl]-3-cyclohexylurea

Cyclohexyl isocyante and the product from Example 99A were processed using the method analogous to that described in Example 99B to afford the title compound. $^1$H NMR (400 MHz, DMSO-d$_6$) δ ppm 9.04 (dd, J=6.9, 1.7 Hz, 1H), 8.56 (dd, J=4.1, 1.7 Hz, 1H), 8.50-8.52 (bs, 1H), 7.78-7.80 (m, 2H), 7.47-7.49 (m, 2H), 7.06 (dd, J=6.9, 4.1 Hz, 1H), 6.87 (d, J=7.6 Hz, 1H), 3.38-3.50 (m, 1H), 1.75-1.80 (m, 2H), 1.63-1.69 (m, 2H), 1.51-1.56 (m, 1H), 1.14-1.38 (m, 5H); MS (ESI) m/z 370 (M+H)$^+$.

Example 109

N-[3-(4-chlorophenyl)pyrazolo[1,5-a]pyrimidin-2-yl]-2-(3,5-dimethoxyphenyl)acetamide 3,5-Dimethoxyphenylacetic acid and the product from Example 99A were processed using the method analogous to that described in example 98 to afford 9 mg (8%) of the title compound. $^1$H NMR (400 MHz, DMSO-$d_6$) δ ppm 10.36-10.57 (bs, 1H), 9.10 (dd, J=6.9, 1.7 Hz, 1H), 8.62 (dd, J=4.1, 1.7 Hz, 1H), 7.66-7.70 (m, 2H), 7.29-7.32 (m, 2H), 7.14 (dd, J=6.9, 4.1 Hz, 1H), 6.47-6.56 (bs, 2H), 6.44 (s, 1H), 3.73 (s, 6H), 3.58 (s, 2H); MS (ESI) m/z 423 (M+H)$^+$.

Example 110

3,3-dimethyl-N-[3-(pyridin-3-yl)pyrazolo[1,5-a]pyrimidin-2-yl]butanamide

Example 110A 3-bromopyrazolo[1,5-a]pyrimidin-2-amine 3,5-Diamino-4-bromopyrazole (Settepani, J. A. Stokes, J. B. *J. Org. Chem.* 1968, 33, 2606) was processed using the method analogous to that described in Example 1C to afford the title compound. $^1$H NMR (300 MHz, DMSO-$d_6$) δ ppm 5.89 (s, 2H), 6.76 (dd, J=6.9, 4.2 Hz, 1H), 8.31 (dd, J=4.4, 1.6 Hz, 1H), 8.73 (dd, J=6.7, 1.6 Hz, 1H); MS (APCI) m/z 213/215 (M+H)$^+$.

Example 110B 3,3-dimethyl-N-[3-(pyridin-3-yl)pyrazolo[1,5-a]pyrimidin-2-yl]butanamide The product from Example 110A was processed using the method analogous to that described in Example 1D to provide the title compound. $^1$H NMR (500 MHz, DMSO-$d_6$) δ ppm 1.07 (s, 9H), 2.25 (s, 2H), 7.12 (dd, J=7.0, 4.0 Hz, 1H), 8.60 (dd, J=4.1, 1.7 Hz, 1H), 9.08 (dd, J=7.0, 1.5 Hz, 1H), 10.12 (s, 1H); MS (ESI) m/z 311/313 (M+H)$^+$.

Example 110C 3,3-dimethyl-N-[3-(pyridin-3-yl)pyrazolo[1,5-a]pyrimidin-2-yl]butanamide A suspension of the product from Example 110B (60 mg, 0.19 mmol), pyridine-3-boronic acid (31 mg, 0.25 mmol; Aldrich), dichlorobis(triphenylphosphine)palladium (II) (6.8 mg, 9.6 μmol; Aldrich) and 1.0 M sodium carbonate (1.1 mL) in 2-propanol (3.3 mL) was purged with nitrogen and then stirred at 100° C. for 2 hours in a sealed tube. The reaction mixture was cooled and partitioned between dichloromethane (2×50 mL) and 1.0 M sodium carbonate (100 mL). The combined organic extracts were dried (sodium sulfate) and concentrated under vacuum. The resulting residue was purified by reverse-phase HPLC [Waters XBridge™ RP18 column, 5 μm, 30×100 mm, flow rate 40 mL/minute, 30-100% gradient of methanol in buffer (0.1 M aqueous ammonium bicarbonate, adjusted to pH 10 with ammonium hydroxide)] to afford the title compound. $^1$H NMR (300 MHz, CD$_3$OD) δ ppm 9.24 (dd, J=2.0, 0.9 Hz, 1H), 8.98 (dd, J=7.0, 1.7 Hz, 1H), 8.88 (ddd, J=8.2, 2.1, 1.4 Hz, 1H), 8.70 (dd, J=4.2, 1.7 Hz, 1H), 8.68 (ddd, J=5.7, 1.3, 0.8 Hz, 1H), 8.08 (ddd, J=8.3, 5.7, 0.7 Hz, 1H), 7.20 (dd, J=7.0, 4.2 Hz, 1H), 2.37 (s, 2H), 1.09 (s, 9H); MS (ESI) m/z 310 (M+H)$^+$.

Example 111

N-{3-[(E)-2-(4-chlorophenyl)vinyl]pyrazolo[1,5-a]pyrimidin-2-yl}-3,3-dimethylbutanamide The product from Example 110B and trans-2-(4-chlorophenyl)vinylboronic acid were processed using the method analogous to that described in Example 110C to afford the title compound. H NMR (400 MHz, CD$_3$OD) δ ppm 8.80 (dd, J=7.0, 1.7 Hz, 1H), 8.60 (dd, J=4.1, 1.6 Hz, 1H), 7.65 (d, J=16.3 Hz, 1H), 7.47-7.50 (m, 2H), 7.31-7.34 (m, 2H), 7.19 (d, J=16.5 Hz, 1H), 7.03 (dd, J=7.0, 4.1 Hz, 1H), 2.41-2.41 (bs, 2H), 1.17 (s, 9H); MS (ESI) m/z 369 (M+H)$^+$.

Example 112

3-cyclopentyl-N-(3-isopropylpyrazolo[1,5-a]pyrimidin-2-yl)propanamide

Example 112A 2-isopropylmalononitrile

Malononitrile (3.96 g, 60 mmol) was added to an ice-cooled suspension of sodium hydride (60% dispersion, 2.42 g, 60 mmol) under nitrogen. The mixture was allowed to warm to room temperature, and 2-iodopropane (6.80 g, 40.0 mmol) was added with a THF (5 mL) rinse. The resulting dark mixture was allowed to stir at room temperature for 12 hours. The reaction mixture was quenched by addition of water (100 mL), and extracted with EtOAc (2×50 mL). The combined organic layer was concentrated under vacuum and the residue was purified by flash chromatography (silica gel, euted with hexanes-EtOAc 95:5-80:20) to provide the title compound. $^1$H NMR (300 MHz, CDCl$_3$) δ ppm 1.26 (d, J=6.8 Hz, 6H), 2.37 (hept of d, J=6.8, 5.4 Hz, 1H), 3.57 (d, J=5.4 Hz, 1H).

Example 112B

4-Isopropyl-1H-pyrazole-3,5-diamine

Hydrazine monohydrate (2.05 mL, 42 mmol) was added to a solution of the product from Example 112A (1.16 g, 10.7 mmol) in EtOH (15 mL). The reaction flask was evacuated and purged with nitrogen (3 cycles), then heated at 80° C. for 22 hours. The yellow solution was cooled to room temperature and concentrated under vacuum. Toluene (8 mL) was added to the residue, and the mixture was concentrated under vacuum to remove excess hydrazine (repeated twice more) to provide the title compound. MS (ESI) m/z 141 (M+H)$^+$.

Example 112C

3-Isopropylpyrazolo[1,5-a]pyrimidin-2-amine

Acetic acid (0.038 mL, 0.67 mmol) was added to a solution of 3-dimethylaminoacrylaldehyde (624 mg, 4.43 mmol) and the product from Example 112B (414 mg, 2.95 mmol) in ethanol (9 mL), and the reaction mixture was heated at 80° C. for 4 hours, then concentrated under vacuum to a dark oil. The residue was purified by flash chromatography (silica gel eluted with hexanes-EtOAc 50:50-0:100) to provide the title compound as a yellow solid. MS (ESI) m/z 177 (M+H)$^+$.

Example 112D 3-cyclopentyl-N-(3-isopropylpyrazolo[1,5-a]pyrimidin-2-yl)propanamide A solution of 3-cyclopentylpropionyl chloride (0.048 mL, 0.31 mmol) in CH$_2$Cl$_2$ (0.2 mL) was added to a stirring solution of the product from Example 112C (35 mg, 0.20 mmol) in pyridine (1.2 mL) in a 4 mL vial. The yellow solution was stirred at room temperature for 3 hours, and then concentrated under vacuum. The residue was dissolved in CH$_2$Cl$_2$ (3 mL) and concentrated under vacuum (repeated three times) to remove excess pyridine. The off-white solid residue was crystallized from 60% ethanol-water (8 mL) to provide the title compound. $^1$H NMR (300 MHz, CD$_3$OD) δ ppm 1.10-1.27 (m, 2H) 1.41 (d, J=7.1 Hz, 6H) 1.48-1.98 (m, 9H) 2.47 (t, J=7.6 Hz, 2H) 3.01-3.22 (m, 1H) 6.91 (dd, J=7.1, 4.1 Hz, 1H) 8.42 (dd, J=4.1, 2.0 Hz, 1H) 8.70 (dd, J=7.1, 1.7 Hz, 1H); MS (ESI) m/z 301 (M+H)$^+$; Anal. Calculated for C$_{17}$H$_{24}$N$_4$O: C, 67.97; H, 8.05; N, 18.65. Found: C, 68.03; H, 8.03; N, 18.60.

Example 113

N-(3-isopropylpyrazolo[1,5-a]pyrimidin-2-yl)-3,3-dimethylbutanamide

A solution of 3,3-dimethylbutanoyl chloride (0.043 mL, 0.31 mmol) in CH$_2$Cl$_2$ (0.2 mL) was added to a stirring solution of the product from Example 112C (35 mg, 0.20 mmol) in pyridine (1.2 mL) in a 4 mL vial. The yellow solution was stirred at room temperature for 3 hours, and then concentrated under vacuum. The residue was dissolved in CH$_2$Cl$_2$ (4 mL) and concentrated under vacuum to remove excess pyridine. The residue was crystallized from 60% ethanol-water (10 mL) to provide the title compound (40 mg). $^1$H NMR (300 MHz, CD$_3$OD) δ ppm 1.13 (s, 9H) 1.31-1.53 (m, 6H) 2.33 (s, 2H) 2.95-3.24 (m, 1H) 6.91 (dd, J=7.0, 4.2 Hz, 1H) 8.42 (dd, J=4.1, 2.0 Hz, 1H) 8.70 (dd, J=7.1, 1.7 Hz, 1H); MS (ESI) m/z 275 (M+H)$^+$; Anal. Calculated for C$_{15}$H$_{22}$N$_4$O: C, 65.67; H, 8.08; N, 20.42. Found: C, 65.74; H, 8.10; N, 20.46.

Example 114

N-[3-(4-chloro-3-methylphenyl)-5,7-dimethylpyrazolo[1,5-a]pyrimidin-2-yl]-3-cyclopropylpropanamide Example 114A Benzyl pent-4-enoate A suspension of K$_2$CO$_3$ (4.17 g, 30.2 mmol) and pent-4-enoic acid (3.01 g, 29.2 mmol) in DMF (25 mL) was stirred at room temperature for 5 minutes. Benzyl bromide (3.55 mL, 29.3 mmol) was added from a syringe over 3 minutes, and the resulting white suspension was stirred at room temperature for 23 hours, then diluted with water (150 mL) and extracted with EtOAc (3×50 mL). The combined extract was washed with saturated brine (30 mL) and concentrated under vacuum to leave the title compound. $^1$H NMR (300 MHz, CD$_3$OD) δ ppm 2.30-2.41 (m, 2H) 2.42-2.50 (m, 2H) 4.96 (dddd, J=10.2, 1.7, 1.4, 1.0 Hz, 1H) 5.03 (dq, J=17.3, 1.6 Hz, 1H) 5.11 (s, 2H) 5.82 (tdd, J=17.0, 10.4, 6.3 Hz, 1H) 7.25-7.38 (m, 5H).

Example 114B

Benzyl 3-cyclopropylpropanoate

N-Methyl-N-nitrosourea (6.4 g, 31 mmol) was added to an ice-cooled mixture of 10% aqueous NaOH (250 g, 625 mmol) and Et$_2$O (300 mL), and the mixture was stirred vigorously with ice cooling for 10 minutes. The ether layer was decanted into a dry, 1 L Erlenmeyer flask, and stirred with ice cooling as a solution of the product from Example 114A (3.00 g, 15.8 mmol) in ether (60 mL) was added. The yellow solution was stirred with ice cooling as Pd(OAc)$_2$ (30 mg, 0.134 mmol) was added. After 1 hour, acetic acid (0.5 mL) was added to consume any excess diazomethane, and the reaction mixture was concentrated under vacuum to a gray oil. The residue was dissolved in EtOAc (50 mL) and washed with saturated NaHCO$_3$(aq) (25 mL). The organic phase was concentrated under vacuum and the residue was purified by flash chromatography (silica gel, eluted with hexanes-EtOAc 100:0-90:10) to provide the title compound. $^1$H NMR (300 MHz, CD$_3$OD) δ ppm −0.02-0.06 (m, 2H) 0.40 (ddd, J=8.1, 5.8, 4.1 Hz, 2H) 0.62-0.78 (m, 1H) 1.51 (q, J=7.1 Hz, 2H) 2.45 (t, J=7.3 Hz, 2H) 5.11 (s, 2H) 7.24-7.40 (m, 5H).

Example 114C 3-cyclopropylpropanoic acid

10% Pd/C (17 mg) was added to a solution of the product from Example 114B (1.01 g, 4.94 mmol) in ethyl acetate (35 mL). The reaction flask was evacuated and purged with nitrogen (4 cycles) then with hydrogen (4 cycles) and the suspension was stirred at room temperature under hydrogen (1 atm) for 2 hours. The flask was evacuated and purged with nitrogen (4 cycles) and the mixture was filtered through diatomaceous earth with EtOAc (40 mL) rinse. The filtrate was concentrated under vacuum to provide the title compound in sufficient purity for use in the next step. $^1$H NMR (300 MHz, CDCl$_3$) δ ppm 0.03-0.11 (m, 2H) 0.45 (ddd, J=8.1, 5.8, 4.1 Hz, 2H) 0.64-0.83 (m, 1H) 1.54 (q, J=7.3 Hz, 2H) 2.46 (t, J=7.5 Hz, 2H).

Example 114D 3-cyclopropylpropanoyl chloride

The product from Example 114C (0.40 g, 3.50 mmol) was dissolved in thionyl chloride (6 mL, 82 mmol) and the solution was heated at 90° C. for 1 hour, then cooled to room temperature. The solution was distilled at atmospheric pressure to remove most of the excess SOCl$_2$, and then under vacuum (air bath 60-65 C/~15 mm) to provide the title compound as a colorless oil.

Example 114E

N-[3-(4-chloro-3-methylphenyl)-5,7-dimethylpyrazolo[1,5-a]pyrimidin-2-yl]-3-cyclopropylpropanamide A solution of the product from Example 114D (40.9 mg, 0.308 mmol) in CH$_2$Cl$_2$ (2 mL) was added to a stirring solution of the product from Example 47C (49.5 mg, 0.173 mmol) in pyridine (1.5 mL) at room temperature. The solution was stirred at room temperature for 1 hour, and then concentrated under vacuum. Methanol (2 mL) was added, and the mixture was concentrated under vacuum. The residue was crystallized from 60% EtOH-water (8 mL) to provide the title compound (52 mg). $^1$H NMR (300 MHz, CD$_3$OD) δ ppm 0.01-0.14 (m, 2H) 0.37-0.52 (m, 2H) 0.66-0.82 (m, 1H) 1.48-1.65 (m, 2H) 2.40 (s, 3H) 2.50 (t, J=7.0 Hz, 2H) 2.57 (s, 3H) 2.72 (s, 3H) 6.88 (s, 1H) 7.37 (d, J=8.1 Hz, 1H) 7.55 (dd, J=8.6, 1.5 Hz, 1H) 7.65 (d, J=1.0 Hz, 1H)); MS (ESI) m/z 383/385 (M+H)$^+$; Anal. Calculated for C$_{21}$H$_{23}$N$_4$OCl: C, 65.87; H, 6.05; N, 14.63. Found: C, 65.56; H, 6.08; N, 14.63.

Example 115

3,3-dimethyl-N-{3-[(E)-2-(6-methylpyridin-3-yl) vinyl]pyrazolo[1,5-a]pyrimidin-2-yl}butanamide

Example 115A (E)-2-methyl-5-(2-(4,4,5,5-tetramethyl-1,3,2-dioxaborolan-2-yl)vinyl)pyridine A dry 500-mL round-bottom flask was charged with carbonylchlorohydridotris(triphenylphosphine) ruthenium(II) (0.571 g, 0.600 mmol; Aldrich) and toluene (80 mL) under nitrogen. After pinacolborane (3.19 mL 22.00 mmol, Aldrich) and 5-ethynyl-2-methylpyridine (2.343 g, 20 mmol; WO2005090333) were added, the mixture was stirred at room temperature for 16 hours. The reaction mixture was extracted with ether. The organic extract was washed with water, dried over $MgSO_4$ and concentrated. The resulting material was purified by flash chromatography (silica gel, hexanes/ethyl acetate, 3:1) to afford the title compound. $^1$H NMR (300 MHz, $CDCl_3$) δ ppm 1.31 (s, 12H), 2.55 (s, 3H), 6.19 (d, J=19.0 Hz, 1H), 7.13 (d, J=8.0 Hz, 1H), 7.36 (d, J=18.0 Hz, 1H), 7.71 (dd, J=8.0, 2.0 Hz, 1H), 8.56 (d, J=2.0 Hz, 1H); MS (DCI/$NH_3$) m/z 246 $(M+H)^+$.

Example 115B 3,3-dimethyl-N-{3-[(E)-2-(6-methylpyridin-3-yl) vinyl]pyrazolo[1,5-a]pyrimidin-2-yl}butanamide The product from Example 115A and the product from Example 110B were processed as described in Example 110C. Purification by reverse-phase HPLC (Waters XBridge™ C18 5 μm OBD 30×100 mm column, flow rate 40 mL/minute, 5-95% gradient of acetonitrile in 0.1% trifluoroacetic acid over 15 minutes) afforded the title compound as the trifluoroacetic acid salt. $^1$H NMR (400 MHz, $CD_3OD$) δ ppm 8.87 (dd, J=6.9, 1.7 Hz, 1H), 8.73 (d, J=2.1 Hz, 1H), 8.67 (dd, J=4.2, 1.7 Hz, 1H), 8.60 (dd, J=8.5, 2.1 Hz, 1H), 7.86 (d, J=8.4 Hz, 1H), 7.80 (d, J=16.3 Hz, 1H), 7.55 (d, J=16.3 Hz, 1H), 7.11 (dd, J=6.9, 4.1 Hz, 1H), 2.76 (s, 3H), 2.43 (s, 2H), 1.16 (s, 9H); MS (ESI) m/z 350 $(M+H)^+$.

Example 116

2-(adamantan-1-yl)-N-[3-(2-naphthyl)pyrazolo[1,5-a]pyrimidin-2-yl]acetamide

The title compound was prepared using the method analogous to that described in Example 110A-110C, substituting 1-adamantylacetyl chloride for 3,3-dimethylbutanoyl chloride, and 2-naphthaleneboronic acid for pyridine-3-boronic acid. $^1$H NMR (400 MHz, DMSO-$d_6$) δ ppm 10.12-10.15 (bs, 1H), 9.13 (dd, J=6.9, 1.7 Hz, 1H), 8.65 (dd, J=4.0, 1.7 Hz, 1H), 8.26 (s, 1H), 7.83-8.00 (m, 4H), 7.46-7.54 (m, 2H), 7.15 (dd, J=6.9, 4.0 Hz, 1H), 2.11-2.12 (bs, 2H), 1.87-1.90 (m, 3H), 1.60-1.63 (m, 9H), 1.50-1.55 (m, 3H); MS (ESI) m/z 437 $(M+H)^+$.

Example 117

N-[3-(4-chlorophenyl)pyrazolo[1,5-a]pyrimidin-2-yl]-3-methyl-3-phenylbutanamide

Example 117A 3-methyl-3-phenylbutanoyl chloride

3-Methyl-3-phenylbutanoic acid (1.78 g, 10.0 mmol) was dissolved in thionyl chloride (5 mL, 68.5 mmol). The reaction mixture was heated at reflux for 6 hours. Concentration of the reaction mixture provided the title compound (1.93 g, 98%), which was used without additional purification.

Example 117B

N-[3-(4-chlorophenyl)pyrazolo[1,5-a]pyrimidin-2-yl]-3-methyl-3-phenylbutanamide

To the product from Example 117A (82 mg, 0.42 mmol) was added a solution of the product from Example 99A (59 mg, 0.2 mmol) in pyridine (2.0 mL). The mixture was stirred at ambient temperature for 1 hour and then at 40° C. for 1 hour. The reaction mixture was concentrated under vacuum and purified by reverse-phase HPLC [Waters XBridge™ RP18 column, 5 μm, 30×100 mm, flow rate 40 mL/minute, 30-100% gradient of methanol in buffer (0.1 M aqueous ammonium bicarbonate, adjusted to pH 10 with ammonium hydroxide)] to afford the title compound. $^1$H NMR (300 MHz, DMSO-$d_6$) δ ppm 10.13-10.16 (bs, 1H), 9.09 (dd, J=7.0, 1.7 Hz, 1H), 8.60 (dd, J=4.1, 1.7 Hz, 1H), 7.68-7.72 (m, 2H), 7.40-7.45 (m, 4H), 7.27-7.35 (m, 2H), 7.15-7.22 (m, 1H), 7.12 (dd, J=7.0, 4.1 Hz, 1H), 2.70 (s, 2H), 1.41 (s, 6H); MS (ESI) m/z 405 $(M+H)^+$; Anal. calculated for $C_{23}H_{21}ClN_4O \cdot 0.1H_2O$: C, 67.93; H, 5.25; N, 13.78. Found C, 67.65; H, 5.08; N, 13.61.

Example 118

3-cyclopropyl-N-(3-isopropylpyrazolo[1,5-a]pyrimidin-2-yl)propanamide

A solution of the product from Example 114D (100 mg, 0.754 mmol) in $CH_2Cl_2$ (0.5 mL) was added to a stirring solution of the product from Example 112C (109 mg, 0.62 mmol) in pyridine (1.0 mL) at room temperature. The solution was stirred at room temperature for 2 hours, and then quenched by addition of methanol (0.5 mL). After 30 minutes, the solution was concentrated under vacuum, and the residue was purified by flash chromatography (silica gel, eluted with EtOAc), followed by crystallization from 80% EtOH-water to provide the title compound. $^1$H NMR (300 MHz, $CD_3OD$) δ ppm 0.07-0.18 (m, 2H) 0.40-0.53 (m, 2H) 0.71-0.89 (m, 1H) 1.41 (d, J=7.1 Hz, 6H) 1.63 (q, J=7.2 Hz, 2H) 2.55 (t, J=7.5 Hz, 2H) 3.14 (hept, J=7.1 Hz, 1H) 6.91 (dd, J=7.0, 4.2 Hz, 1H) 8.42 (dd, J=4.1, 1.7 Hz, 1H) 8.70 (dd, J=7.1, 1.7 Hz, 1H) MS (ESI) m/z 273 $(M+H)^+$; Anal. Calculated for $C_{15}H_{20}N_4O$: C, 66.15; H, 7.40; N, 20.57. Found: C, 66.39; H, 7.28; N, 20.26.

Example 119

3-cyclopentyl-N-[3-(pyridin-3-yl)pyrazolo[1,5-a] pyrimidin-2-yl]propanamide

The title compound was prepared using the methods analogous to that described in Examples 110A-110C, substituting 3-cyclopentylpropionyl chloride for 3,3-dimethylbutanoyl chloride. $^1$H NMR (400 MHz, DMSO-$d_6$) δ ppm 10.14-10.50 (bs, 1H), 9.12 (dd, J=6.9, 1.7 Hz, 1H), 8.93 (d, J=2.2 Hz, 1H), 8.64 (dd, J=4.1, 1.7 Hz, 1H), 8.45 (dd, J=4.7, 1.6 Hz, 1H), 8.10 (ddd, J=7.9, 1.8 Hz, 1H), 7.44 (ddd, J=8.0, 4.8, 0.7 Hz, 1H), 7.16 (dd, J=6.9, 4.1 Hz, 1H), 2.35 (t, J=7.4 Hz, 2H), 1.66-1.79 (m, 3H), 1.46-1.60 (m, 6H), 1.04-1.11 (m, 2H); MS (ESI) m/z 336 $(M+H)^+$.

Example 120

3-cyclopentyl-N-{3-[4-(trifluoromethoxy)phenyl]pyrazolo[1,5-a]pyrimidin-2-yl}propanamide The title compound was prepared using the methods analogous to that described in Examples 1A-1D, substituting 3-cyclopentylpropionyl chloride for 3,3-dimethylbutanoyl chloride. $^1$H NMR (400 MHz, DMSO-$d_6$) δ ppm 10.21-10.22 (m, 1H), 9.11 (dd, J=6.9, 1.7 Hz, 1H), 8.63 (dd, J=4.1, 1.7 Hz, 1H), 7.87-7.90 (m, 2H), 7.40-7.43 (m, 2H), 7.15 (dd, J=6.9, 4.1 Hz, 1H), 2.35 (t, J=7.3 Hz, 2H), 1.70-1.74 (m, 3H), 1.45-1.58 (m, 6H), 1.03-1.11 (m, 2H); MS (ESI) m/z 419 (M+H)$^+$; Anal. calculated for $C_{21}H_{21}F_3N_4O_2$: C, 60.28; H, 5.06; N, 13.39; F, 13.62. Found C, 60.35; H, 5.06; N, 13.17; F, 13.37.

Example 121

(±)-exo-2-bicyclo[2.2.1]hept-2-yl-N-(3-tert-butylpyrazolo[1,5-a]pyrimidin-2-yl)acetamide

Example 121A (±)-exo-2-(bicyclo[2.2.1]heptan-2-yl)acetyl chloride

2-Norbornaneacetic acid (2.0 mL, 13.8 mL) was dissolved in thionyl chloride (6 mL, 82 mmol) and the reaction mixture was heated at reflux for 6 hours. Concentration of the reaction mixture afforded the title compound (2.32 g, 97%), which was used without further purification.

Example 121B (±)-exo-2-bicyclo[2.2.1]hept-2-yl-N-(3-tert-butylpyrazolo[1,5-a]pyrimidin-2-yl)acetamide The product from Example 105B and the product from Example 121A were processed using the method analogous to that described in Example 105C to afford the title compound. $^1$H NMR (300 MHz, DMSO-$d_6$): δ ppm 1.07-1.23 (m, 4H), 1.31-1.54 (m, 12H), 11.82-2.28 (m, 5H), 6.99 (dd, J=7.1, 4.0 Hz, 1H), 8.48 (dd, J=4.0, 2.0 Hz, 1H), 8.92 (dd, J=7.1, 2.0 Hz, 1H), 9.65 (s, 1H); MS (DCI) m/z 327 (M+H)$^+$.

Example 122

3-cyclopentyl-N-(3-isopropyl-5,7-dimethylpyrazolo[1,5-a]pyrimidin-2-yl)propanamide

Example 122A

3-Isopropyl-5,7-dimethylpyrazolo[1,5-a]pyrimidin-2-amine

A solution of acetylacetone (1034 mg, 10.33 mmol) and the product from Example 112B (965 mg, 6.88 mmol) in acetic acid (5 mL) was heated at 115° C. for 90 minutes, and then cooled to room temperature. Hydroxylamine hydrochloride (520 mg) was added, and the solution was stirred at room temperature for 14 hours, and then concentrated under vacuum. The residue was purified by HPLC (30×100 mm XBridge column eluted with 0.1 M aqueous $(NH_4)_2CO_3$-MeOH, 60:40-0:100 over 15 min) to provide the title compound. MS (DCI/NH$_3$) m/z 205 (M+H)$^+$.

Example 122B 3-cyclopentyl-N-(3-isopropyl-5,7-dimethylpyrazolo[1,5-a]pyrimidin-2-yl)propanamide A solution of 3-cyclopentylpropanoyl chloride (0.049 mL, 0.323 mmol) in $CH_2Cl_2$ (0.5 mL) was added to a stirring solution of the product from Example 122A (60 mg, 0.294 mmol) in pyridine (2.5 mL). After 1 hour, methanol (2 mL) was added and the yellow solution was concentrated under vacuum. The residue was purified by flash chromatography (silica gel eluted with hexanes-EtOAc, 80:20-50:50) to provide the title compound. $^1$H NMR (300 MHz, CD$_3$OD) δ ppm 1.12-1.27 (m, 2H) 1.38 (d, J=6.8 Hz, 6H) 1.49-1.96 (m, 9H) 2.40-2.51 (m, 2H) 2.53 (s, 3H) 2.63 (s, 3H) 3.01-3.21 (m, 1H) 6.73 (s, 1H); MS (ESI) m/z 329 (M+H)$^+$.

Example 123

N-(3-tert-butylpyrazolo[1,5-a]pyrimidin-2-yl)-2-(4-fluorophenyl)acetamide

The product from Example 105B and 4-fluorophenylacetyl chloride were processed using the method analogous to that described in Example 105C to afford the title compound. $^1$H NMR (300 MHz, DMSO-$d_6$) δ ppm 1.38 (s, 9H), 3.63 (s, 2H), 6.99 (dd, J=7.1, 4.1 Hz, 1H), 7.13-7.18 (m, 2H), 7.31-7.41 (m, 2H), 8.48 (dd, J=4.1, 1.7 Hz, 1H), 8.91 (dd, J=7.1, 1.7 Hz, 1H), 9.94 (s, 1H); MS (DCI) m/z 327 (M+H)$^+$.

Example 124

(±)-exo-2-bicyclo[2.2.1]hept-2-yl-N-{3-[4-(trifluoromethoxy)phenyl]pyrazolo[1,5-a]pyrimidin-2-yl}acetamide The title compound was prepared using the methods analogous to that described in Examples 1A-1D, substituting the product from Example 121A for 3,3-dimethylbutanoyl chloride. $^1$H NMR (400 MHz, DMSO-$d_6$) δ ppm 10.19-10.22 (bs, 1H), 9.11 (dd, J=6.9, 1.8 Hz, 1H), 8.63 (dd, J=4.0, 1.8 Hz, 1H), 7.82-7.93 (m, 2H), 7.36-7.46 (m, 2H), 7.15 (dd, J=7.0, 4.1 Hz, 1H), 2.28 (dd, J=13.9, 8.2 Hz, 1H), 2.12-2.22 (m, 2H), 1.93-2.01 (bs, 1H), 1.79-1.91 (m, 1H), 1.26-1.53 (m, 4H), 1.00-1.20 (m, 4H); MS (ESI) m/z 431 (M+H)$^+$; Anal. calculated for $C_{22}H_{21}F_3N_4O_2$: C, 61.39; H, 4.92; N, 13.02. Found C, 61.40; H, 4.85; N, 12.87.

Example 125 methyl 2-[(3-cyclopentylpropanoyl)amino]pyrazolo[1,5-a]pyrimidine-3-carboxylate

Example 125A

Methyl 2-aminopyrazolo[1,5-a]pyrimidine-3-carboxylate

Acetic acid (0.013 mL, 0.221 mmol) was added to a mixture of methyl 3,5-diamino-1H-pyrazole-4-carboxylate (689 mg, 4.41 mmol, prepared as described in J. Prakt. Chem. 1965, 27, 239-250) and 3-dimethylaminoacrylaldehyde (531 mg, 5.36 mmol) in EtOH (9 mL), and the mixture was heated at reflux for 22 hours, and then cooled to room temperature.

The slurry was concentrated under vacuum, and the residue was dissolved in hot methanol (20 mL), allowed to cool to room temperature, then filtered and dried to provide the title compound, in sufficient purity for use in the next step. MS (ESI) m/z 193 (M+H)+.

Example 125B methyl 2-[(3-cyclopentylpropanoyl)amino]pyrazolo [1,5-a]pyrimidine-3-carboxylate A solution of 3-cyclopentylpropionyl chloride (0.58 mL, 3.8 mmol) in $CH_2Cl_2$ (0.5 mL) was added to a suspension of the product from Example 125A (300 mg, 1.56 mmol) in pyridine (5 mL) at room temperature. After 4 hours, methanol (10 mL) was added to quench the excess acyl chloride, and the mixture was stirred for 15 minutes, and then concentrated under vacuum. The residue was crystallized from 86% methanol-water (24 mL) to provide the title compound. $^1$H NMR (300 MHz, DMSO-$d_6$) δ ppm 1.01-1.22 (m, 2H) 1.39-1.69 (m, 6H) 1.68-1.88 (m, 3H) 2.46-2.54 (m, 2H) 3.81 (s, 3H) 7.25 (dd, J=6.9, 4.2 Hz, 1H) 8.75 (dd, J=4.4, 1.6 Hz, 1H) 9.18 (dd, J=6.9, 1.8 Hz, 1H) 10.04 (s, 1H); MS (ESI) m/z 317 (M+H)+; Anal. Calculated for $C_{16}H_{20}N_4O_3$: C, 60.75; H, 6.37; N, 17.71. Found: C, 60.71; H, 5.85; N, 17.48.

Example 126

N-(3-tert-butylpyrazolo[1,5-a]pyrimidin-2-yl)-3-methyl-3-phenylbutanamide

The product from Example 105B and the product from Example 117A were processed using the method analogous to that described in Example 105C to afford the title compound. $^1$H NMR (300 MHz, DMSO-$d_6$) δ ppm 1.39 (s, 9H), 1.45 (s, 6H), 2.65 (s, 2H), 6.97 (dd, J=7.1, 4.1 Hz, 1H), 7.15-7.19 (m, 1H), 7.28-7.33 (m, 2H), 7.42-7.44 (m, 2H), 8.46 (dd, J=4.1, 1.7 Hz, 1H), 8.91 (dd, J=7.0, 1.9 Hz, 1H), 9.59 (s, 1H); MS (DCI) m/z 351 (M+H)+.

Example 127

N-(3-tert-butylpyrazolo[1,5-a]pyrimidin-2-yl)-2-(3,5-difluorophenyl)acetamide

The product from Example 105B and 3,5-difluorophenylacetyl chloride were processed using the method analogous to that described in Example 105C to afford the title compound. $^1$H NMR (300 MHz, DMSO-$d_6$) δ ppm 1.39 (s, 9H), 3.70 (s, 2H), 6.98-7.16 (m, 4H), 8.49 (dd, J=4.1, 1.7 Hz, 1H), 8.92 (dd, J=6.8, 1.7 Hz, 1H), 10.01 (s, 1H); MS (DCI) m/z 345 (M+H)+.

Example 128

N-[3-(3-fluorophenyl)pyrazolo[1,5-a]pyrimidin-2-yl]-3-methyl-3-phenylbutanamide

Example 128A 3-(3-fluorophenyl)pyrazolo[1,5-a]pyrimidin-2-amine

The title compound was prepared using methods analogous to that described in Examples 1A-1C, substituting 1-fluoro-3-iodobenzene for 1-iodo-4-(trifluoromethoxy)benzene. MS (APCI) m/z 229 [M+H]+.

Example 128B

The product from Example 128A and 3-methyl-3-phenylbutanoic acid were processed using method analogous to that described in Example 98 to afford the title compound. $^1$H NMR (300 MHz, DMSO-$d_6$) δ ppm 10.14-10.17 (bs, 1H), 9.10 (dd, J=6.9, 1.7 Hz, 1H), 8.63 (dd, J=4.1, 1.7 Hz, 1H), 7.53-7.63 (m, 2H), 7.37-7.45 (m, 3H), 7.24-7.36 (m, 2H), 7.05-7.20 (m, 3H), 2.71 (s, 2H), 1.41 (s, 6H); MS (APCI) m/z 389 (M+H)+; Anal. calculated for $C_{23}H_{21}FN_4O$: C, 71.12; H, 5.45; N, 14.42; F, 4.89. Found C, 71.00; H, 5.40; N, 14.52; F, 5.13.

Example 129

N-(3-tert-butylpyrazolo[1,5-a]pyrimidin-2-yl)-3-phenylpropanamide

The product from Example 105B and 3-phenylpropionyl chloride were processed using the method analogous to that described in Example 105C to afford the title compound. $^1$H NMR (300 MHz, DMSO-$d_6$) δ ppm 1.40 (s, 9H), 2.56-2.67 (m, 2H), 2.90 (t, J=7.6 Hz, 2H), 6.99 (dd, J=7.0, 3.9 Hz, 1H), 7.17-7.31 (m, 5H), 8.48 (dd, J=4.1, 1.7 Hz, 1H), 8.92 (dd, J=7.1, 1.7 Hz, 1H), 9.74 (s, 1H); MS (DCI) m/z 323 (M+H)+.

Example 130

N-(3-tert-butylpyrazolo[1,5-a]pyrimidin-2-yl)-2-cyclohexylacetamide

The product from Example 105B and 2-cyclohexylacetyl chloride were processed using the method analogous to that described in Example 105C to afford the title compound. $^1$H NMR (300 MHz, DMSO-$d_6$) δ ppm 0.92-1.03 (m, 2H), 1.11-1.29 (m, 3H), 1.44 (s, 9H), 1.59-1.81 (m, 6H), 2.18 (d, J=6.1 Hz, 2H), 6.99 (dd, J=7.1, 4.1 Hz, 1H), 8.47 (dd, J=4.1, 1.7 Hz, 1H), 8.92 (dd, J=7.1, 1.7 Hz, 1H), 9.64 (s, 1H); MS (DCI) m/z 315 (M+H)+.

Example 131

(±)-N-(3-tert-butylpyrazolo[1,5-a]pyrimidin-2-yl)-2-(1-methyl-2,3-dihydro-1H-inden-1-yl)acetamide Example 131A (±)-ethyl 2-(1-methyl-2,3-dihydro-1H-inden-1-yl)acetate To a suspension of NaH (1.8 g, 45.4 mmol, 60% dispersion in mineral oil) in 1,2-dimethoxythane (90 mL) at 0° C. was added slowly triethyl phosphonoactate (9.1 mL, 45.4 mmol). The resulting mixture was stirred for 15 minutes at 0° C., 15 minutes at room temperature, and then cooled to 0° C. A solution of 2,3-dihydro-1H-inden-1-one (3.0 g, 22.7 mmol) in 1,2-dimethoxythane (10 mL) was added and the resulting solution was stirred for 5 minutes at 0° C., warmed to room temperature and refluxed for overnight. The reaction mixture was cooled to room temperature and $H_2O$ (50 mL) was added. The aqueous layer was extracted with ethyl acetate (3×50 mL). The combined organic layers were washed with $H_2O$, brine, dried over $Na_2SO_4$, and filtered, and the solvent was evaporated under reduced pressure. The crude product was purified by flash chromatography (Hex-EtOAc, 0 to 10%) to obtain 3.1 g of mixture of (E)-ethyl 2-(2,3-dihydro-1H-inden- 1-ylidene)acetate as a mixture with ethyl 2-(1H-inden-3-yl) acetate (1:1) and 0.3 g of (Z)-ethyl 2-(2,3-dihydro-1H-inden-1-ylidene)acetate.

To a suspension of copper iodide (1.9 g, 9.9 mmol) in diethyl ether (10 mL) was added methyl lithium (12.4 mL, 19.8 mmol, 1.6M in diethyl ether) at 0° C. and the mixture was stirred for 10 min. The solvent was removed under reduced pressure at 0° C. and then $CH_2Cl_2$ (10 mL) was added. The reaction mixture was stirred for 5 minutes at 0° C., and then the solvent was removed again under reduced pressure at 0° C. To the residue was added pre-cooled $CH_2Cl_2$ (75 mL), cooled to −78° C., and then added trimethylsilyl chloride (1.3 mL, 9.9 mmol) and a solution of a mixture of (E)-ethyl 2-(2,3-dihydro-1H-inden-1-ylidene)acetate and ethyl 2-(1H-inden-3-yl)acetate (1:1 mixture, 1 g, 4.9 mmol) in $CH_2Cl_2$ (10 mL), successively. The resulted mixture was allowed to warm to room temperature and stirred overnight. The reaction was quenched by addition of a mixture of aqueous saturated $NH_4Cl$ and 28% $NH_4OH$ (1:1, 50 mL). The mixture was extracted with diethyl ether (3×50 mL) and the combined extracts were washed with water, dried ($Na_2SO_4$), filtered, and concentrated under reduced pressure. The crude product was purified by flash chromatography (Hexanes-EtOAc, 0 to 10%) to give 0.47 g of the title compound. Additionally, 0.17 g of unreacted ethyl 2-(1H-inden-3-yl) acetate was recovered. MS (DCI/$NH_3$) m/z 236 (M+$NH_4$)$^+$.

Example 131B (±)-2-(1-methyl-2,3-dihydro-1H-inden-1-yl)acetic acid

To a solution of the product from Example 131A (0.47 g, 2.1 mmol) in tetrahydrofuran (6 mL), water (3 mL), and methanol (6 mL) was added 5N NaOH aqueous solution (2.1 mL, 10.8 mmol). After stirring at room temperature for 4 hours, the reaction mixture was concentrated to half the volume, diluted with water (10 mL), washed with methylene chloride (10 mL), acidified to pH~2 with aqueous 3N HCl solution, and extracted with methylene chloride (3×15 mL). The combined organic extracts were washed with $H_2O$ (50 mL), brine (50 mL), dried over $MgSO_4$, filtered, and concentrates under reduced pressure to obtain 0.32 g of the title compound. MS (DCI/$NH_3$) m/z 208 (M+$NH_4$)$^+$ Example 131C (±)-N-(3-tert-butylpyrazolo[1,5-a]pyrimidin-2-yl)-2-(1-methyl-2,3-dihydro-1H-inden-1-yl)acetamide To a mixture from Example 131B (55 mg, 0.29 mmol) and the product from Example 105B (50 mg, 0.26 mmol) in tetrahydrofuran (10 mL), was added a solution of 1-propanephosphonic acid (50% w/w in ethyl acetate (0.5 mL, 0.8 mmol) followed by triethylamine (0.1 mL, 0.8 mmol). The reaction was stirred at 60° C. overnight. The reaction was quenched with 1M $NaHCO_3$ (10 mL). The aqueous layer was extracted with EtOAc (2×20 mL). The combined organic layers were dried over $Na_2SO_4$, filtered, and concentrated under reduced pressure. The residue was purified by column chromatography (SiO$_2$, 0-50% of EtOAc in hexanes) to obtain the title compound. $^1$H NMR (300 MHz, DMSO-d$_6$) δ ppm 1.38 (s, 3H), 1.43 (s, 9H), 1.81-1.93 (m, 1H), 2.32-2.46 (m, 2H), 2.58-2.71 (m, 1H), 2.81-2.95 (m, 2H), 6.99 (dd, J=7.1, 4.1 Hz, 1H), 7.09-7.31 (m, 4H), 8.47 (dd, J=4.1, 1.7 Hz, 1H), 8.93 (dd, J=7.0, 1.9 Hz, 1H), 9.67 (s, 1H); MS (ESI$^+$) m/z 363 (M+H)$^+$ Example 132

N-(3-tert-butylpyrazolo[1,5-a]pyrimidin-2-yl)-3-cyclohexylpropanamide

The product from Example 105B and 3-cyclohexylpropionyl chloride were processed using the method analogous to that described in Example 105C to afford the title compound. $^1$H NMR (300 MHz, DMSO-d$_6$) δ ppm 0.81-0.93 (m, 2H), 1.05-1.31 (m, 4H), 1.44-1.52 (m, 11H), 1.57-1.78 (m, 5H), 2.24-2.35 (m, 2H), 6.99 (dd, J=6.7, 4.0 Hz, 1H), 8.48 (dd, J=4.0, 1.6 Hz, 1H), 8.92 (dd, J=6.9, 1.8 Hz, 1H), 9.66 (s, 1H); MS (DCI) m/z 329 (M+H)$^+$; EA calculated for $C_{19}H_{28}N_4O$: C, 69.48; H, 8.59; N, 17.06. Found: C, 69.41; H, 8.33; N, 16.89.

Example 133

2-(cyclopentyloxy)-N-(3-isopropylpyrazolo[1,5-a]pyrimidin-2-yl)acetamide

Example 133A

Ethyl 2-(cyclopentyloxy)acetate

A solution of cyclopentanol (2.28 mL, 25.1 mmol) in THF (10 mL) was added dropwise with ice cooling to a suspension of sodium hydride (60% dispersion in oil, 1.054 g, 26.3 mmol) in THF (20 mL). The mixture was stirred with ice cooling under nitrogen for 30 minutes, and then a solution of ethyl bromoacetate (2.66 mL, 23.95 mmol) in THF (10 mL) was added dropwise, followed by a THF (10 mL) rinse. The reaction mixture was allowed to warm to room temperature and stirred for 20 hours. Water (60 mL) was added cautiously, and the resulting mixture was extracted with EtOAc (2×50 mL). The combined extract was washed with saturated brine (40 mL), dried (MgSO$_4$), filtered, and concentrated to provide the title compound, used directly in the next step.

Example 133B 2-(cyclopentyloxy)acetic acid

The product from Example 133A (2.56 g) was combined with MeOH (10 mL) and 40% aqueous KOH (8 mL) and water (8 mL) were added. The mixture was heated at reflux for 6 hours, and then cooled to room temperature. The mixture was concentrated under vacuum, and the residue was diluted with water (15 mL) and washed with hexanes (20 mL). The aqueous layer was cooled with ice and brought to pH<3 by addition of 10% HCl (30 mL). The resulting mixture was extracted with $CH_2Cl_2$ (3×20 mL). The combined extract was concentrated under vacuum to provide the title compound. $^1$H NMR (300 MHz, CDCl$_3$) δ ppm 1.52-1.83 (m, 8H) 4.05 (s, 2H) 4.06-4.12 (m, 1H).

Example 133C 2-(cyclopentyloxy)acetyl chloride

The product from Example 133B (0.33 g, 2.29 mmol) was taken up in thionyl chloride (4 mL, 54.8 mmol) and heated at 70° C. for 1 hour. The reaction mixture was cooled to room temperature and concentrated under vacuum. The residue was taken up in $CH_2Cl_2$ (5 mL) and concentrated again to remove excess thionyl chloride. This was repeated twice more. The residue was dissolved in $CH_2Cl_2$ (2.5 mL) to provide a solution of the title compound that was used for the next step.

Example 133D 2-(cyclopentyloxy)-N-(3-isopropylpyrazolo[1,5-a]pyrimidin-2-yl)acetamide The product from Example 133C (1.5 mL of solution in $CH_2Cl_2$) was added to a solution of the product from Example 112C (86 mg, 0.49 mmol) in pyridine (1.0 mL) in a 4 mL vial. The reaction mixture was stirred at room temperature for 2 h. Methanol (0.5 mL) was added, and the solution was stirred for 30 minutes and then concentrated under vacuum. The residue was purified by flash chromatography (silica gel, eluted with hexanes-EtOAc, 70:30-0:100) to provide the title compound. $^1$H NMR (300 MHz, $CDCl_3$) δ ppm 1.45 (d, J=7.1 Hz, 6H) 1.57-1.69 (m, 2H) 1.70-1.87 (m, 6H) 3.24 (hept, J=7.1 Hz, 1H) 4.10-4.13 (m, 1H) 4.11-4.12 (m, 2H) 6.72 (dd, J=6.8, 4.1 Hz, 1H) 8.39 (dd, J=4.1, 1.7 Hz, 1H) 8.58 (dd, J=6.8, 1.7 Hz, 1H) 8.60 (s, 1H); MS (ESI) m/z 303 (M+H)$^+$; Anal. Calculated for $C_{16}H_{22}N_4O_2$: C, 63.71; H, 7.44; N, 18.20. Found: C, 63.56; H, 7.33; N, 18.53.

Example 134

N-[3-(4-chloro-3-methylphenyl)-5,7-dimethylpyrazolo[1,5-a]pyrimidin-2-yl]-2-(cyclopentyloxy)acetamide The product from Example 133C (1.0 mL of solution in $CH_2Cl_2$) was added to a stirring solution of the product from Example 47C (51 mg, 0.178 mmol) in pyridine (1.4 mL). The reaction mixture was stirred at room temperature for 2 hours, and then quenched by addition of MeOH (0.5 mL). After 30 min, concentrated $NH_4OH$ (0.2 mL) was added, and the mixture was stirred at room temperature for 12 hours, and then concentrated under vacuum. The residue was purified by flash chromatography (silica gel, eluted with hexanes-EtOAc, 70:30-0:100) to provide the title compound. $^1$H NMR (300 MHz, $CD_3OD$) δ ppm 1.52-1.81 (m, 8H) 2.42 (s, 3H) 2.56 (s, 3H) 2.73 (d, J=1.0 Hz, 3H) 4.05-4.12 (m, 1H) 4.09 (s, 2H) 6.86-6.89 (q, J=1.0 Hz, 1H) 7.40 (d, J=8.5 Hz, 1H) 7.54 (dd, J=8.4, 1.9 Hz, 1H) 7.65 (d, J=1.9 Hz, 1H); MS (DCI/$NH_3$) m/z 413/415 (M+H)$^+$.

Example 135

3-cyclopentyl-N-[3-(3-fluorophenyl)pyrazolo[1,5-a]pyrimidin-2-yl]propanamide

The title compound was prepared using the methods analogous to that described in Examples 1A-1D, substituting 1-fluoro-3-iodobenzene for 1-iodo-4-(trifluoromethoxy)benzene, and 3-cyclopentylpropionyl chloride for 3,3-dimethylbutanoyl chloride. $^1$H NMR (400 MHz, DMSO-$d_6$) δ ppm 10.21-10.24 (bs, 1H), 9.11 (dd, J=6.9, 1.7 Hz, 1H), 8.65 (dd, J=4.1, 1.7 Hz, 1H), 7.67 (ddd, J=7.9, 1.1 Hz, 1H), 7.60 (ddd, J=11.1, 2.5, 1.7 Hz, 1H), 7.41-7.48 (m, 1H), 7.16 (dd, J=7.0, 4.1 Hz, 1H), 7.10 (dddd, J=9.1, 8.5, 2.7, 0.9 Hz, 1H), 2.35 (t, J=7.4 Hz, 2H), 1.66-1.81 (m, 3H), 1.46-1.66 (m, 6H), 1.00-1.17 (m, 2H); MS (APCI) m/z 353 (M+H)$^+$; Anal. calculated for $C_{20}H_{21}FN_4O$: C, 68.16; H, 6.01; N, 15.90; F, 5.39. Found C, 67.79; H, 5.86; N, 15.84; F, 5.64.

Example 136

(2E)-N-(3-tert-butylpyrazolo[1,5-a]pyrimidin-2-yl)-3-phenylacrylamide

The product from Example 105B and cinnamoyl chloride were processed using the method analogous to that described in Example 105C to afford the title compound. $^1$H NMR (300 MHz, DMSO-$d_6$) δ ppm 1.47 (s, 9H), 6.84 (d, J=14.9 Hz, 1H), 7.02 (dd, J=7.1, 4.1 Hz, 1H), 7.38-7.48 (m, 3H), 7.57-7.64 (m, 3H), 8.51 (dd, J=4.1, 1.7 Hz, 1H), 8.95 (dd, J=7.0, 1.9 Hz, 1H), 9.98 (s, 1H); MS (DCI) m/z 321 (M+H)$^+$; EA calculated for $C_{19}H_{20}N_4O$: C, 71.23; H, 6.29; N, 17.49. Found: C, 70.95; H, 6.06; N, 17.36.

Example 137

N-(3-tert-butylpyrazolo[1,5-a]pyrimidin-2-yl)-2-phenylacetamide

A mixture from Example 105B (103.8 mg, 0.55 mmol), phenylacetic acid (138.6 mg, 1.02 mmol) and 1-(3-dimethylaminopropyl)-3-ethylcarbodiimide HCL (206.7 mg, 1.08 mmol) in pyridine (1.5 mL) and DMF (1.5 mL) was stirred at ambient temperature for 5 hours. The mixture was concentrated. Purification by reverse phase HPLC afforded 123.7 mg (74%) of the title compound. $^1$H NMR (300 MHz, DMSO-$d_6$) δ ppm 1.39 (s, 9H), 3.63 (s, 2H), 6.99 (dd, J=7.1, 4.1 Hz, 1H), 7.23-7.34 (m, 5H), 8.48 (dd, J=4.1, 1.7 Hz, 1H), 8.91 (dd, J=7.1, 1.7 Hz, 1H), 9.93 (s, 1H); MS (DCI) m/z 309 (M+H)$^+$.

Example 138

2-(3,5-dimethoxyphenyl)-N-[3-(3-fluorophenyl)pyrazolo[1,5-a]pyrimidin-2-yl]acetamide 3,5-Dimethoxyphenylacetic acid and the product from Example 128A were processed as using the method analogous to that described in example 104 to afford the title compound. $^1$H NMR (300 MHz, DMSO-$d_6$) δ ppm 10.40-10.51 (bs, 1H), 9.11 (dd, J=7.0, 1.8 Hz, 1H), 8.65 (dd, J=4.1, 1.7 Hz, 1H), 7.59 (ddd, J=11.2, 2.6, 1.6 Hz, 1H), 7.52 (d, J=7.9 Hz, 1H), 7.26-7.34 (m, 1H), 7.16 (dd, J=7.0, 4.1 Hz, 1H), 7.02-7.09 (m, 1H), 6.46-6.54 (m, 2H), 6.38-6.43 (m, 1H), 3.67-3.77 (bs, 6H), 3.59-3.62 (bs, 2H); MS (ESI) m/z 407 (M+H)$^+$. Anal. calculated for $C_{22}H_{19}FN_4O_3$: C, 65.02; H, 4.71; N, 13.79. Found C, 64.80; H, 4.54; N, 13.77.

Example 139

3-cyclopentyl-N-[3-(4-fluoro-3-methylphenyl)-6-methylpyrazolo[1,5-a]pyrimidin-2-yl]propanamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and 3-cyclopentylpropionyl chloride for 3,3-dimethylbutanoyl chloride. $^1$H NMR (300 MHz, $CD_3OD$) δ ppm 1.01-1.27 (m, 2H), 1.49-1.88 (m, 9H), 2.29 (d, J=2.0 Hz, 3H), 2.39-2.48 (m, 2H), 2.40 (d, J=1.0 Hz, 3H), 7.25 (t, J=8.3 Hz, 1H), 7.42-7.50 (m, 2H), 8.48 (d, J=2.4 Hz, 1H), 8.66 (dq, J=2.4, 1.0 Hz, 1H); MS (DCI/$NH_3$) m/z 381 (M+H)$^+$.

Example 140

2-(4-fluorophenyl)-N-{3-[4-(trifluoromethoxy)phenyl]pyrazolo[1,5-a]pyrimidin-2-yl}acetamide

Example 140A

N-(3-bromopyrazolo[1,5-a]pyrimidin-2-yl)-2-(4-fluorophenyl)acetamide

The product from Example 110A and 4-fluorophenylacetic acid were processed using the method analogous to that described in Example 137 to provide the title compound. MS (APCI) m/z 349/351 (M+H)$^+$.

Example 140B 2-(4-fluorophenyl)-N-{3-[4-(trifluoromethoxy)phenyl]pyrazolo[1,5-a]pyrimidin-2-yl}acetamide The product from Example 140A and 4-trifluoromethoxyphenylboronic acid were processed using the method analogous to that described in example 110C to afford the title compound. $^1$H NMR (400 MHz, DMSO-d$_6$) δ ppm 10.29-10.76 (bs, 1H), 9.11 (dd, J=6.9, 1.7 Hz, 1H), 8.63 (dd, J=4.1, 1.7 Hz, 1H), 7.75-7.78 (m, 2H), 7.32-7.39 (m, 2H), 7.24-7.29 (m, 2H), 7.14-7.19 (m, 3H), 3.67 (s, 2H); MS (APCI) m/z 431 (M+H)$^+$. Anal. calculated for C$_{21}$H$_{14}$F$_4$N$_4$O$_2$: C, 58.61; H, 3.28; N, 13.02. Found C, 58.37; H, 2.91; N, 12.81.

Example 141

3,3-dimethyl-N-[3-(2-methylphenyl)pyrazolo[1,5-a]pyrimidin-2-yl]butanamide

O-tolylboronic acid and the product from Example 110B were processed using the method analogous to that described in example 110C to afford the title compound. $^1$H NMR (400 MHz, DMSO-d$_6$) δ ppm 9.86 (s, 1H), 9.07 (dd, J=6.9, 1.7 Hz, 1H), 8.49 (dd, J=4.0, 1.8 Hz, 1H), 7.21-7.29 (m, 2H), 7.14-7.20 (m, 2H), 7.05 (dd, J=7.0, 4.0 Hz, 1H), 2.15 (s, 3H), 2.07 (s, 2H), 0.87 (s, 9H); MS (APCI) m/z 323 (M+H)$^+$.

Example 142

2-(adamantan-1-yl)-N-{3-[4-(trifluoromethoxy)phenyl]pyrazolo[1,5-a]pyrimidin-2-yl}acetamide The title compound was prepared using the methods analogous to that described in Examples 1A-1D, substituting 1-adamantylacetyl chloride for 3,3-dimethylbutanoyl chloride. $^1$H NMR (400 MHz, DMSO-d$_6$) δ ppm 10.10-10.14 (bs, 1H), 9.12 (dd, J=6.9, 1.7 Hz, 1H), 8.62 (dd, J=4.1, 1.7 Hz, 1H), 7.86-7.89 (m, 2H), 7.39-7.42 (m, 2H), 7.14 (dd, J=6.9, 4.1 Hz, 1H), 2.09-2.10 (bs, 2H), 1.90-1.94 (m, 3H), 1.60-1.69 (m, 12H); MS (APCI) m/z 471 (M+H)$^+$.

Example 143

2-(cyclopentylthio)-N-[3-(4-fluoro-3-methylphenyl)-6-methylpyrazolo[1,5-a]pyrimidin-2-yl]acetamide

Example 143A

Ethyl 2-(cyclopentylthio)acetate

Solid K$_2$CO$_3$ (9.01 g, 65.2 mmol) was added to a stirring solution of ethyl bromoacetate (5.16 mL, 46.6 mmol) and cyclopentanethiol (4.97 mL, 46.6 mmol) in DMF (25 mL). The resulting suspension was warmed at 65° C. for 4 hours. The reaction mixture was cooled to room temperature, diluted with water (100 mL) and extracted with hexanes (3×50 mL). The combined extract was washed with saturated brine (30 mL) and concentrated under vacuum to provide the title compound. $^1$H NMR (300 MHz, CDCl$_3$) δ ppm 1.29 (t, J=7.1 Hz, 3H), 1.43-1.65 (m, 4H), 1.66-1.81 (m, 2H), 1.93-2.10 (m, 2H), 3.13-3.30 (m, 1H), 3.25 (s, 2H), 4.19 (q, J=7.1 Hz, 2H).

Example 143B 2-(cyclopentylthio)acetic acid

A solution of 20% aqueous KOH (14.8 g, 52.8 mmol) was added to a solution of the product from Example 143A (8.89 g, 46.7 mmol) in EtOH (30 mL), and the resulting mixture was heated at reflux for 3 hours. The reaction solution was cooled to room temperature and concentrated under vacuum. The residue was diluted with water (20 mL) and CH$_2$Cl$_2$ (50 mL) and cooled in ice as 37% HCl (15 mL) was added gradually with good stirring (final pH~2). The aqueous layer was separated and extracted with CH$_2$Cl$_2$ (50 mL) and the combined organic phase was washed with brine (30 mL), dried (Na$_2$SO$_4$), filtered, and concentrated under vacuum to provide the title compound. $^1$H NMR (300 MHz, CDCl$_3$) δ ppm 1.44-1.66 (m, 4H), 1.67-1.86 (m, 2H), 1.93-2.12 (m, 2H), 3.14-3.31 (m, 1H), 3.30 (s, 2H).

Example 143C 2-(cyclopentylthio)acetyl chloride

The product from Example 143B (6.56 g) was combined with thionyl chloride (50 mL, 685 mmol) and the reaction mixture was heated at 70° C. for 2 hours. The reaction mixture was concentrated under vacuum, and the residue was dissolved in CHCl$_3$ (50 mL) and concentrated again to remove excess thionyl chloride. The residue was distilled under vacuum (air bath 100-110° C./~10 mm) to provide the title compound, used directly for the next step.

Example 143D 2-(cyclopentylthio)-N-[3-(4-fluoro-3-methylphenyl)-6-methylpyrazolo[1,5-a]pyrimidin-2-yl]acetamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and the product from Example 143C for 3,3-dimethylbutanoyl chloride. $^1$H NMR (400 MHz, CD$_3$OD) δ ppm 1.44-1.64 (m, 4H), 1.65-1.81 (m, 2H), 1.98-2.08 (m, 2H), 2.29 (d, J=1.5 Hz, 3H), 2.40 (d, J=0.9 Hz, 3H), 3.21-3.34 (m, 1H), 3.41 (s, 2H), 7.26 (t, J=8.1 Hz, 1H), 7.40-7.60 (m, 2H), 8.48 (d, J=2.1 Hz, 1H), 8.60-8.70 (m, 1H); MS (ESI) m/z 399 (M+H)$^+$.

Example 144

N-{3-[(1E)-3,3-dimethylbut-1-en-1-yl]pyrazolo[1,5-a]pyrimidin-2-yl}-3,3-dimethylbutanamide 3,3-Dimethyl-1-butenylboronic acid (Aalenchem) and the product from Example 110B were processed using the method analogous to that described in Example 110C to provide the title compound. $^1$H NMR (500 MHz, DMSO-$d_6$) δ ppm 10.03-10.05 (bs, 1H), 9.00 (dd, J=6.9, 1.7 Hz, 1H), 8.57 (dd, J=4.1, 1.7 Hz, 1H), 7.03 (dd, J=6.9, 4.1 Hz, 1H), 6.75 (d, J=16.3 Hz, 1H), 6.23 (d, J=16.3 Hz, 1H), 2.26 (s, 2H), 1.09 (s, 9H), 1.07 (s, 9H); MS (ESI) m/z 315 (M+H)$^+$.

Example 145

3-cyclopentyl-N-[3-(1-ethylcyclohexyl)pyrazolo[1,5-a]pyrimidin-2-yl]propanamide

Example 145A 2-(Cyclohexylidene)malononitrile

Acetic acid was added at room temperature to a stirring mixture of malononitrile (2.65 mL, 42.1 mmol), cyclohexanone (5.03 g, 51.3 mmol) and NH$_4$OAc (6.49 g, 84 mmol) in toluene (200 mL). The resulting mixture was heated at reflux under a Dean-Stark trap for 2 hours (6 mL water collected), then cooled to room temperature. The mixture was concentrated under vacuum, and the residue was distilled under vacuum (air bath 110-130° C./~10 mm) to provide the title compound. $^1$H NMR (300 MHz, CDCl$_3$) δ ppm 1.61-1.74 (m, 2H), 1.81 (ddt, J=6.5, 6.2, 5.8 Hz, 4H), 2.66 (dd, J=6.5, 6.2 Hz, 4H).

Example 145B 2-(1-Vinylcyclohexyl)malononitrile

A solution of vinylmagnesium bromide (1 M in THF, 24 mL, 24 mmol) was added dropwise over 2 min to a solution of the product from Example 145A (730 mg, 4.99 mmol) in THF (8 mL) under nitrogen. The reaction mixture was stirred at room temperature for 13 hours, then quenched by cautious addition of saturated aqueous NH$_4$Cl (25 mL). The mixture was stirred vigorously for 10 minutes, and then diluted with water (10 mL). The aqeuous layer was separated and extracted with EtOAc (25 mL). The combined organic phase was concentrated under vacuum, and the residue was purified by flash chromatography (silica gel eluted with hexanes-EtOAc, 90:10-80:20) to provide the title compound. $^1$H NMR (300 MHz, CDCl$_3$) δ ppm 1.24-1.37 (m, 2H), 1.40-1.68 (m, 6H), 1.85-2.03 (m, 2H), 3.56 (s, 1H), 5.39 (d, J=17.4 Hz, 1H), 5.53 (d, J=10.7 Hz, 1H), 5.73 (dd, J=17.5, 10.7 Hz, 1H).

Example 145C 4-(1-Vinylcyclohexyl)-1H-pyrazole-3,5-diamine

Hydrazine monohydrate (0.098 mL, 1.69 mmol) was added to a solution of the product from Example 145B (295 mg, 1.69 mmol) in n-butanol (5 mL), and the mixture was heated at 100° C. under nitrogen for 36 hours. The reaction solution was cooled to room temperature and concentrated under vacuum. The residue was dilute with water (15 mL) and extracted with EtOAc (2×15 mL). The combined organic phase was dried (MgSO$_4$), filtered, and concentrated under vacuum to provide the title compound as an inseparable 1:1 mixture with 3,5-diamino-4-(1-ethylcyclohexyl)pyrazole, used directly in the next step.

Example 145D 3-(1-Vinylcyclohexyl)pyrazolo[1,5-a]pyrimidin-2-amine

Acetic acid (0.02 mL) was added to a solution of 3-(dimethylamino)acrylaldehyde (218 mg, 2.199 mmol) and the product from Example 145C (335 mg, 1.624 mmol) in EtOH (7 mL). The reaction mixture was heated at 90° C. for 2 hours, then cooled to room temperature and concentrated under vacuum. The residue was purified by HPLC (30×100 mm XBridge column eluted with 0.1 M aqueous (NH$_4$)$_2$CO$_3$-MeOH, 80:20-0:100 over 15 min) to provide the title compound. $^1$H NMR (300 MHz, CD$_3$OD) δ ppm 1.41-1.77 (m, 8H), 2.59-2.71 (m, 2H), 4.92 (d, J=17.4 Hz, 1H), 5.04 (d, J=10.7 Hz, 1H), 5.98 (dd, J=17.4, 10.7 Hz, 1H), 6.63 (dd, J=6.7, 4.2 Hz, 1H), 8.23 (dd, J=4.2, 1.8 Hz, 1H), 8.44 (dd, J=6.9, 1.8 Hz, 1H).

Example 145E 3-(1-Ethyllcyclohexyl)pyrazolo[1,5-a]pyrimidin-2-amine

A second-eluting component was isolated from the chromatographic purification described in Example 145D, and identified as the title compound. $^1$H NMR (300 MHz, CD$_3$OD) δ ppm 0.68 (t, J=7.5 Hz, 3H), 1.32-1.61 (m, 8H), 1.67 (q, J=7.4 Hz, 2H), 2.67-2.83 (m, 2H), 6.61 (dd, J=6.8, 4.0 Hz, 1H), 8.20 (dd, J=4.0, 2.0 Hz, 1H), 8.42 (dd, J=6.9, 1.8 Hz, 1H); MS (DCI/NH$_3$) m/z 245 (M+H)$^+$.

Example 145F 3-cyclopentyl-N-[3-(1-ethylcyclohexyl)pyrazolo[1,5-a]pyrimidin-2-yl]propanamide The product from Example 145E (44 mg, 0.180 mmol) was dissolved in pyridine (300 μL), and 3-cyclopentylpropionyl chloride (50 uL) was added at room temperature. The reaction mixture was stirred at room temperature for 2 hours, and then quenched by addition of methanol (0.5 mL). After 1 h, the solution was concentrated under vacuum and the residue was purified by HPLC (30×100 mm XBridge column eluted with aqueous 0.1 M (NH$_4$)$_2$CO$_3$-MeOH (60:40-0:100 over 15 min), followed by crystallization from 67% ethanol-water (6 mL). Recrystallization from EtOH (3 mL) provided the title compound. $^1$H NMR (300 MHz, CD$_3$OD) δ ppm 0.65 (t, J=7.5 Hz, 3H), 1.07-1.95 (m, 19H), 1.74 (q, J=7.5 Hz, 2H), 2.44 (t, J=7.6 Hz, 2H), 2.65-2.80 (m, 2H), 6.93 (dd, J=7.1, 4.1 Hz, 1H), 8.44 (dd, J=4.1, 1.9 Hz, 1H), 8.69 (dd, J=7.0, 1.9 Hz, 1H); MS (DCI/NH$_3$) m/z 369 (M+H)$^+$.

Example 146

(±)-exo-2-bicyclo[2.2.1]hept-2-yl-N-[3-(1-ethylcyclohexyl)pyrazolo[1,5-a]pyrimidin-2-yl]acetamide The product from Example 145E (44 mg, 0.180 mmol) was dissolved in pyridine (300 μL) and the product from Example 121A (50 μL) was added at room temperature. The reaction mixture was stirred at room temperature for 2 hours, and then quenched by addition of methanol (0.5 mL). After 1 hour, the solution was concentrated under vacuum and the residue purified by crystallization from EtOH (5 mL) to provide the title compound. $^1$H NMR (300 MHz, CD$_3$OD) δ ppm 0.65 (t, J=7.5 Hz, 3H), 1.10-1.63 (m, 16H), 1.74 (q, J=7.5 Hz, 2H), 1.93-2.15 (m, 2H), 2.19-2.43 (m, 3H), 2.66-2.80 (m, 2H), 6.93 (dd, J=7.1, 4.1 Hz, 1H), 8.44 (dd, J=3.9, 1.9 Hz, 1H), 8.68 (dd, J=7.1, 2.0 Hz, 1H); MS (DCI/NH$_3$) m/z 381 (M+H)$^+$.

Example 147

3,3-dimethyl-N-(3-{(E)-2-[4-(trifluoromethyl)phenyl]vinyl}pyrazolo[1,5-a]pyrimidin-2-yl)butanamide Trans-2-[4-(trifluoromethyl)phenyl]vinylboronic acid and the product from Example 110B were processed using the method analogous to that described in Example 110C to provide the title compound. $^1$H NMR (400 MHz, DMSO-d$_6$) δ ppm 10.27-10.28 (bs, 1H), 9.11 (dd, J=6.9, 1.7 Hz, 1H), 8.69 (dd, J=4.1, 1.7 Hz, 1H), 7.63-7.73 (m, 5H), 7.34 (d, J=16.5 Hz, 1H), 7.15 (dd, J=6.9, 4.1 Hz, 1H), 2.35 (s, 2H), 1.09 (s, 9H); MS (ESI) m/z 403 (M+H)$^+$.

Example 148 tert-butyl {3-[4-(trifluoromethoxy)phenyl]pyrazolo[1,5-a]pyrimidin-2-yl}carbamate

Example 148A tert-butyl 3-bromopyrazolo[1,5-a]pyrimidin-2-ylcarbamate

3-Bromopyrazolo[1,5-a]pyrimidine-2-carboxylic acid (1.95 g, 8.06 mmol; Art-Chem) was suspended in tert-butyl alcohol (75 mL). Triethylamine (1.35 mL, 9.67 mmol) and diphenylphosphoryl azide (2.09 mL, 9.67 mmol) was added and the mixture was stirred under refluxing condition for 4 hours. The reaction mixture was cooled to ambient temperature and concentrated under vacuum. The resulting residue was purified by reverse-phase HPLC [Waters XBridge™ RP18 column, 5 μm, 50×100 mm, flow rate 100 mL/minute, 20-75% gradient of methanol in buffer (0.1 M aqueous ammonium bicarbonate, adjusted to pH 10 with ammonium hydroxide)] to afford the title compound. MS (ESI) m/z 310/313 (M−H)$^−$.

Example 148B tert-butyl {3-[4-(trifluoromethoxy)phenyl]pyrazolo[1,5-a]pyrimidin-2-yl}carbamate The product from Example 148A and 4-trifluoromethoxyphenylboronic acid were processed using the method analogous to that described in example 110C to afford the title compound. $^1$H NMR (400 MHz, DMSO-d$_6$) δ ppm 9.52-9.54 (bs, 1H), 9.08 (dd, J=6.9, 1.7 Hz, 1H), 8.61 (dd, J=4.1, 1.7 Hz, 1H), 7.87-7.90 (m, 2H), 7.44-7.46 (m, 2H), 7.12 (dd, J=6.9, 4.1 Hz, 1H), 1.25 (s, 9H); MS (ESI) m/z 393 (M−H)$^−$.

Example 149

N-[3-(4-fluoro-3-methylphenyl)-6-methylpyrazolo[1,5-a]pyrimidin-2-yl]-3-methyl-3-phenylbutanamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and the product from Example 117A for 3,3-dimethylbutanoyl chloride. $^1$H NMR (300 MHz, DMSO-d$_6$) δ ppm 1.40 (s, 6H), 2.26 (d, J=1.6 Hz, 3H), 2.34 (s, 3H), 2.67 (s, 2H), 7.10-7.19 (m, 2H), 7.27-7.32 (m, 2H), 7.40-7.50 (m, 3H), 7.63 (dd, J=7.7, 1.8 Hz, 1H), 8.50 (d, J=2.0 Hz, 1H), 8.90-8.91 (m, 1H), 10.02 (s, 1H); MS (DCI) m/z 417 (M+H)$^+$.

Example 150

(±)-exo-2-bicyclo[2.2.1]hept-2-yl-N-[3-(4-fluoro-3-methylphenyl)-6-methylpyrazolo[1,5-a]pyrimidin-2-yl]acetamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and the product from Example 121A for 3,3-dimethylbutanoyl chloride. $^1$H NMR (300 MHz, DMSO-d$_6$) δ ppm 1.06-1.17 (m, 4H), 1.32-1.50 (m, 4H), 1.81-1.90 (m, 2H), 1.94-1.99 (m, 1H), 2.09-2.18 (m, 2H), 2.24-2.26 (m, 4H), 2.64 (s, 3H), 7.13-7.19 (m, 1H), 7.57-7.64 (m, 2H), 8.51 (d, J=2.0 Hz, 1H), 8.91 (dd, J=2.0, 1.2 Hz, 1H), 10.02 (s, 1H); MS (DCI) m/z 393 (M+H)$^+$.

Example 151

2-(adamantan-1-yl)-N-[3-(4-fluoro-3-methylphenyl)-6-methylpyrazolo[1,5-a]pyrimidin-2-yl]acetamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and 1-adamantylacetyl chloride for 3,3-dimethylbutanoyl chloride. $^1$H NMR (300 MHz, DMSO-d$_6$) δ ppm 1.55-1.69 (m, 12H), 1.89-1.95 (m, 3H), 2.07 (s, 2H), 2.26 (d, J=1.6 Hz, 3H), 2.34 (s, 3H), 7.13-7.19 (m, 1H), 7.57-7.64 (m, 2H), 8.50 (d, J=2.4 Hz, 1H), 8.92-8.93 (m, 1H), 9.94 (s, 1H); MS (DCI) m/z 433 (M+H)$^+$.

Example 152

N-(3-tert-butylpyrazolo[1,5-a]pyrimidin-2-yl)-2-(4-chlorophenyl)acetamide

The product from Example 105B and 4-chlorophenylacetic acid were processed using the method analogous to that described in Example 137 to afford the title compound. $^1$H NMR (300 MHz, DMSO-d$_6$) δ ppm 1.39 (s, 9H), 3.64 (s, 2H), 7.00 (dd, J=7.1, 4.0 Hz, 1H), 7.37-7.41 (m, 4H), 8.48 (dd, J=4.0, 1.6 Hz, 1H), 8.92 (dd, J=7.1, 1.6 Hz, 1H), 9.98 (s, 1H); MS (DCI) m/z 343 (M+H)$^+$.

Example 153

3-cyclopentyl-N-(3-{(E)-2-[4-(trifluoromethyl)phenyl]vinyl}pyrazolo[1,5-a]pyrimidin-2-yl)propanamide

Example 153A

N-(3-bromopyrazolo[1,5-a]pyrimidin-2-yl)-3-cyclopentylpropanamide

The product from Example 110A and 3-cyclopentylpropionyl chloride were processed using the method analogous to that described in Example 1D to provide the title compound. MS (APCI) m/z 337/339 (M+H)$^+$.

Example 153B 3-cyclopentyl-N-(3-{(E)-2-[4-(trifluoromethyl)phenyl]vinyl}pyrazolo[1,5-a]pyrimidin-2-yl)propanamide Trans-2-[4-(trifluoromethyl)phenyl]vinylboronic acid and the product from Example 153A were processed using the method analogous to that described in Example 110C to provide the title compound. $^1$H NMR (400 MHz, DMSO-d$_6$) δ ppm 10.32-10.34 (bs, 1H), 9.10 (dd, J=6.9, 1.7 Hz, 1H), 8.69 (dd, J=4.1, 1.7 Hz, 1H), 7.70 (s, 4H), 7.64 (d, J=16.3 Hz, 1H), 7.34 (d, J=16.2 Hz, 1H), 7.14 (dd, J=6.9, 4.1 Hz, 1H), 2.49 (t, J=7.9 Hz, 2H), 1.76-1.86 (m, 3H), 1.45-1.70 (m, 6H), 1.07-1.18 (m, 2H); MS (ESI) m/z 429 (M+H)$^+$.

Example 154

N-(3-tert-butylpyrazolo[1,5-a]pyrimidin-2-yl)-2-cyclopentylacetamide

The product from Example 105B and cyclopentylacetyl chloride were processed using the method analogous to that described in Example 105C to afford the title compound. $^1$H NMR (300 MHz, DMSO-d$_6$) δ ppm 1.13-1.24 (m, 2H), 1.45-1.65 (m, 13H), 1.71-1.82 (m, 2H), 2.19-2.28 (m, 3H), 6.99 (dd, J=7.1, 4.1 Hz, 1H), 8.48 (dd, J=3.9, 1.9 Hz, 1H), 8.92 (dd, J=7.0, 1.9 Hz, 1H), 9.64 (br s, 1H); MS (DCI) m/z 301 (M+H)$^+$.

Example 155

N-(3-tert-butylpyrazolo[1,5-a]pyrimidin-2-yl)-2-(4-methoxyphenyl)acetamide

The product from Example 105B and 4-methoxyphenylacetic acid were processed using the method analogous to that described in Example 137 to afford the title compound. $^1$H NMR (300 MHz, DMSO-d$_6$) δ ppm 1.39 (s, 9H), 3.55 (s, 2H), 3.74 (s, 3H), 6.87-6.97 (m, 2H), 6.99 (dd, J=7.1, 4.1 Hz, 1H), 7.23-7.26 (m, 2H), 8.47 (dd, J=3.9, 1.9 Hz, 1H), 8.91 (dd, J=7.0, 1.5 Hz, 1H), 9.87 (s, 1H); MS (DCI) m/z 339 (M+H)$^+$.

Example 156

3,3-dimethyl-N-(3-{[4-(trifluoromethoxy)phenyl]ethynyl}pyrazolo[1,5-a]pyrimidin-2-yl)butanamide Triethylamine (3 mL) was added to a mixture of bis(tri-t-butylphosphino)palladium (9.6 mg, 0.019 mmol; Strem), 1-ethynyl-4-trifluoromethoxybenzene (0.12 mL, 0.75 mmol), CuI (3.6 mg, 0.019 mmol) and the product from Example 110B (117 mg, 0.38 mmol) in anhydrous tetrahydrofuran (3 mL). The mixture was purged with a nitrogen stream for 2 minutes, and then stirred at 85° C. for 18 hours in a sealed tube. The reaction mixture was cooled and partitioned between dichloromethane (2×50 mL) and 1.0 M sodium carbonate (100 mL). The combined organic extracts were dried (sodium sulfate), filtered, and concentrated under vacuum. The resulting residue was purified by reverse-phase HPLC [Waters XBridge™ RP18 column, 5 μm, 30×100 mm, flow rate 40 mL/minute, 20-100% gradient of acetonitrile in buffer (0.1 M aqueous ammonium bicarbonate, adjusted to pH 10 with ammonium hydroxide)] to afford the title compound. $^1$H NMR (400 MHz, DMSO-d$_6$) δ ppm 10.34 (s, 1H), 9.12 (dd, J=6.9, 1.7 Hz, 1H), 8.65 (dd, J=4.1, 1.7 Hz, 1H), 7.58-7.60 (m, 2H), 7.41-7.44 (m, 2H), 7.17 (dd, J=6.9, 4.1 Hz, 1H), 2.29 (s, 2H), 1.07 (s, 9H); MS (APCI) m/z 417 (M+H)$^+$.

Example 157

N-[3-(4-chlorophenyl)pyrazolo[1,5-a]pyrimidin-2-yl]-3-cyclohexylpropanamide

The title compound was prepared using the methods analogous to that described in Examples 1A-1D, substituting 1-chloro-4-iodobenzene for 1-iodo-4-(trifluoromethoxy)benzene, and 3-cyclohexylpropionyl chloride for 3,3-dimethylbutanoyl chloride. $^1$H NMR (300 MHz, DMSO-d$_6$) δ ppm 0.80-0.91 (m, 2H), 1.09-1.25 (m, 4H), 1.42-1.49 (m, 2H), 1.16-1.75 (m, 5H), 2.34 (t, J=7.5 Hz, 2H), 7.14 (dd, J=6.9, 4.2 Hz, 1H), 7.45-7.49 (m, 2H), 7.78-7.81 (m, 2H), 8.62 (dd, J=4.2, 1.8 Hz, 1H), 9.09 (dd, J=7.1, 1.6 Hz, 1H), 10.19 (s, 1H); MS (DCI) m/z 383 (M+H)$^+$.

Example 158

(±)-exo-2-bicyclo[2.2.1]hept-2-yl-N-[3-(4-chlorophenyl)pyrazolo[1,5-a]pyrimidin-2-yl]acetamide The title compound was prepared using the methods analogous to that described in Examples 1A-1D, substituting 1-chloro-4-iodobenzene for 1-iodo-4-(trifluoromethoxy)benzene, and the product from Example 121A for 3,3-dimethylbutanoyl chloride. $^1$H NMR (300 MHz, DMSO-d$_6$) δ ppm 1.07-1.19 (m, 4H), 1.32-1.52 (m, 4H), 1.81-1.91 (m, 1H), 1.97-1.99 (m, 1H), 2.13-2.32 (m, 3H), 7.14 (dd, J=7.0, 4.2 Hz, 1H), 7.44-7.48 (m, 2H), 7.77-7.82 (m, 2H), 8.62 (dd, J=4.2, 1.9 Hz, 1H), 9.09 (dd, J=7.1, 1.7 Hz, 1H), 10.17 (s, 1H); MS (DCI) m/z 381 (M+H)$^+$.

Example 159

3-methyl-N-{7-methyl-3-[4-(trifluoromethoxy)phenyl]pyrazolo[1,5-a]pyrimidin-2-yl}-3-phenylbutanamide The title compound was prepared using the methods analogous to that described in Examples 1A-1D, substituting 4-(dimethylamino)but-3-en-2-one for 3-(dimethylamino)acrylaldehyde, and the product from Example 117A for 3,3-dimethylbutanoyl chloride. $^1$H NMR (300 MHz, DMSO-d$_6$) δ ppm 1.39 (s, 6H), 2.26 (d, J=1.6 Hz, 3H), 2.72-2.73 (m, 5H), 7.10 (d, J=4.4 Hz, 1H), 7.17 (t, J=7.1 Hz, 1H), 7.28-7.34 (m, 4H), 7.41-7.44 (m, 2H), 7.73-7.77 (m, 2H), 8.51 (d, J=4.0 Hz, 1H), 10.22 (s, 1H); MS (DCI) m/z 469 (M+H)$^+$.

Example 160

(±)-exo-2-bicyclo[2.2.1]hept-2-yl-N-{7-methyl-3-[4-(trifluoromethoxy)phenyl]pyrazolo[1,5-a]pyrimidin-2-yl}acetamide The title compound was prepared using the methods analogous to that described in Examples 1A-1D, substituting 4-(dimethylamino)but-3-en-2-one for 3-(dimethylamino)acrylaldehyde, and the product from Example 121A for 3,3-dimethylbutanoyl chloride. $^1$H NMR (300 MHz, DMSO-d$_6$) δ ppm 1.05-1.18 (m, 4H), 1.32-1.78 (m, 4H), 1.80-1.89 (m, 1H), 1.94-1.98 (m, 1H), 2.13-2.32 (m, 3H), 2.73 (s, 3H), 7.11 (d, J=4.4 Hz, 1H), 7.38-7.40 (m, 2H), 7.85-7.88 (m, 2H), 8.53 (d, J=4.4 Hz, 1H), 10.23 (s, 1H); MS (DCI) m/z 445 (M+H)$^+$.

Example 161

N-{3-[(1E)-3,3-dimethylbut-1-en-1-yl]pyrazolo[1,5-a]pyrimidin-2-yl}-2-(4-fluorophenyl)acetamide The product from Example 140A and 3,3-dimethyl-1-butenylboronic acid were processed using the method analogous to that described in Example 110C to provide the title compound. $^1$H NMR (400 MHz, DMSO-d$_6$) δ ppm 10.32-10.43 (bs, 1H), 8.99 (dd, J=7.0, 1.7 Hz, 1H), 8.56 (dd, J=4.1, 1.7 Hz, 1H), 7.37-7.43 (m, 2H), 7.13-7.21 (m, 2H), 7.04 (dd, J=7.0, 4.1 Hz, 1H), 6.63 (d, J=16.3 Hz, 1H), 6.08 (d, J=16.5 Hz, 1H), 3.70 (s, 2H), 1.01 (s, 9H); MS (APCI) m/z 353 (M+H)$^+$.

Example 162

2-(adamantan-1-yl)-N-[3-(4-chlorophenyl)pyrazolo[1,5-a]pyrimidin-2-yl]acetamide

The title compound was prepared using the methods analogous to that described in Examples 1A-1D, substituting 1-chloro-4-iodobenzene for 1-iodo-4-(trifluoromethoxy)benzene, and 1-adamantylacetyl chloride for 3,3-dimethylbutanoyl chloride. $^1$H NMR (300 MHz, DMSO-d$_6$) δ ppm 1.56-1.69 (m, 12H), 1.90-1.95 (m, 3H), 2.09 (s, 2H), 7.13 (dd, J=7.1, 4.0 Hz, 1H), 7.45-7.48 (m, 2H), 7.78-7.81 (m, 2H), 8.61 (dd, J=4.2, 1.8 Hz, 1H), 9.11 (dd, J=6.9, 1.8 Hz, 1H), 10.08 (s, 1H); MS (DCI) m/z 421 (M+H)$^+$.

Example 163

N-(3-tert-butylpyrazolo[1,5-a]pyrimidin-2-yl)-2-cyclohexylideneacetamide

The product from Example 105B and 2-cyclohexylideneacetic acid were processed using the method analogous to that described in Example 137 to afford the title compound. $^1$H NMR (300 MHz, DMSO-d$_6$) δ ppm 1.44 (s, 9H), 1.50-1.63 (m, 6H), 2.15-2.18 (m, 2H), 2.80-2.82 (m, 2H), 5.80 (br s, 1H), 6.98 (dd, J=6.8, 4.1 Hz, 1H), 8.48 (dd, J=4.1, 2.0 Hz, 1H), 8.91 (dd, J=7.1, 1.7 Hz, 1H), 9.58 (br s, 1H); MS (DCI) m/z 313 (M+H)$^+$.

Example 164

N-[3-(4-fluoro-3-methylphenyl)-6-methylpyrazolo[1,5-a]pyrimidin-2-yl]-4,4-dimethylpentanamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and 4,4-dimethylpentanoyl chloride for 3,3-dimethylbutanoyl chloride. $^1$H NMR (300 MHz, DMSO-d$_6$) δ ppm 0.88 (s, 9H), 1.46-1.51 (m, 2H), 2.25-2.30 (m, 5H), 2.35 (s, 3H), 7.14-7.21 (m, 1H), 7.60-7.64 (m, 2H), 8.52 (d, J=2.0 Hz, 1H), 8.92 (s, 1H), 10.08 (s, 1H); MS (DCI) m/z 369 (M+H)$^+$.

Example 165

N-(3-tert-butylpyrazolo[1,5-a]pyrimidin-2-yl)-3-[4-(trifluoromethyl)phenyl]propanamide The product from Example 105B and 4-(trifluoromethyl)hydrocinnamic acid were processed using the method analogous to that described in Example 137 to afford the title compound. $^1$H NMR (300 MHz, DMSO-d$_6$) δ ppm 1.36 (s, 9H), 2.61-2.73 (m, 2H), 3.00 (t, J=7.5 Hz, 2H), 6.99 (dd, J=7.1, 4.1 Hz, 1H), 7.78-7.51 (m, 2H), 7.63-7.66 (m, 2H), 8.48 (dd, J=4.1, 1.7 Hz, 1H), 8.91 (dd, J=7.1, 1.7 Hz, 1H), 9.75 (s, 1H); MS (DCI) m/z 391 (M+H)$^+$.

Example 166

N-(3-tert-butylpyrazolo[1,5-a]pyrimidin-2-yl)-2-(4-isopropylphenyl)acetamide

The product from Example 105B and 4-isopropylphenylacetic acid were processed using the method analogous to that described in Example 137 to afford the title compound. $^1$H NMR (300 MHz, DMSO-d$_6$) δ ppm 1.19 (d, J=6.7 Hz, 3H), 1.39 (s, 9H), 2.82-2.91 (m, 1H), 3.58 (s, 2H), 6.99 (dd, J=7.1, 4.0 Hz, 1H), 7.18-7.23 (m, 4H), 8.48 (dd, J=4.0, 2.0 Hz, 1H), 8.91 (dd, J=7.0, 2.0 Hz, 1H), 9.91 (s, 1H); MS (DCI) m/z 351 (M+H)$^+$.

Example 167

3,3-dimethyl-N-{3-[(1E)-prop-1-en-1-yl]pyrazolo[1,5-a]pyrimidin-2-yl}butanamide

The product from Example 110B and trans-1-propen-1-ylboronic acid were processed using the method analogous to that described in Example 110C to provide the title compound. $^1$H NMR (400 MHz, DMSO-d$_6$) δ ppm 9.99-10.02 (bs, 1H), 8.99 (dd, J=6.9, 1.7 Hz, 1H), 8.54 (dd, J=4.1, 1.7 Hz, 1H), 7.02 (dd, J=6.9, 4.1 Hz, 1H), 6.63 (dq, J=15.8, 6.6 Hz, 1H), 6.31 (dd, J=15.9, 2.0 Hz, 1H), 2.26 (s, 2H), 1.85 (dd, J=6.6, 1.7 Hz, 3H), 1.06 (s, 9H); MS (ESI) m/z 273 (M+H)$^+$.

Example 168

2-(4-fluorophenyl)-N-{5-methyl-3-[4-(trifluoromethoxy)phenyl]pyrazolo[1,5-a]pyrimidin-2-yl}acetamide

Example 168A

5-Methyl-3-(4-(trifluoromethoxy)phenyl)pyrazolo[1,5-a]pyrimidin-2-amine

The product from Example 1B (200 mg, 0.775 mmol) was charged to a microwave vial with a stir bar. A solution of 4-(dimethylamino)but-3-en-2-one (175 mg, 1.55 mmol) in ethanol (2 mL) was added, and the mixture was stirred at room temperature as acetic acid (25 ΞL, 0.437 mmol) was added. The solution was irradiated in the microwave at 150° C. for 35 minutes, then cooled to room temperature and finally to –10° C. The precipitate was removed by filtration, and the filtrate was concentrated under vacuum. The residue was purified by flash chromatography (silica gel eluted with hexanes-EtOAc, 70:30-40:60) to provide the title compound. $^1$H NMR (300 MHz, DMSO-d$_6$) δ ppm 2.47 (s, 3H), 5.71 (s, 2H), 6.69 (d, J=7.1 Hz, 1H), 7.39 (d, J=8.1 Hz, 2H), 7.87-7.98 (m, 2H), 8.62 (d, J=7.1 Hz, 1H).

Example 168B 2-(4-fluorophenyl)-N-{5-methyl-3-[4-(trifluoromethoxy)phenyl]pyrazolo[1,5-a]pyrimidin-2-yl}acetamide 4-Fluorophenylacetic acid (32 mg, 0.21 mmol) was added to a stirring solution of the product from Example 168A (20 mg, 0.065 mmol) in DMF (0.5 mL) and pyridine (0.5 mL). 1-(3-Dimethylaminopropyl)-3-ethylcarbodiimide hydrochloride (43 mg, 0.22 mmol) was added and stirring was continued at room temperature for 40 h. The reaction mixture was quenched by addition of MeOH (1 mL) and HOAc (0.1 mL) and stirred for 40 minutes. The solution was concentrated under vacuum, and the residue was purified by HPLC (30×100 mm XBridge column eluted with aqueous 0.1 M $(NH_4)_2CO_3$-MeOH, 60:40-0:100 over 15 min) to provide the title compound. $^1$H NMR (300 MHz, DMSO-$d_6$) δ ppm 2.56 (s, 3H), 3.65 (s, 2H), 7.03 (d, J=7.1 Hz, 1H), 7.15 (t, J=8.8 Hz, 2H), 7.25 (d, J=8.5 Hz, 2H), 7.29-7.40 (m, 2H), 7.76 (d, J=8.8 Hz, 2H), 8.94 (d, J=7.1 Hz, 1H), 10.42 (s, 1H); MS (DCI/NH$_3$) m/z 445 (M+H)$^+$.

Example 169

N-(3-tert-butylpyrazolo[1,5-a]pyrimidin-2-yl)-2-[(cis)-6,6-dichlorobicyclo[3.1.0]hex-2-yl]acetamide 2-(6,6-Dichlorobicyclo[3.1.0]hexan-2-yl)acetic acid (83 mg, 0.32 mmol, prepared as an exo,endo mixture as described in *Can. J. Chem.* 1981 57, 164-174) was added to a stirring solution of the product from Example 105B (42.1 mg, 0.221 mmol) in DMF (1 mL) and pyridine (1 mL). 1-(3-Dimethylaminopropyl)-3-ethylcarbodiimide hydrochloride (81 mg, 0.420 mmol) was added and the mixture was stirred at room temperature for 20 hours. The reaction was quenched by addition of MeOH (1 mL) and HOAc (0.1 mL) and stirred for 40 minutes. The solution was concentrated under vacuum, and the residue was purified by HPLC (30×100 mm XBridge column eluted with aqueous 0.1 M $(NH_4)_2CO_3$-MeOH, 60:40-0:100 over 15 min) to provide the title compound. $^1$H NMR (300 MHz, CD$_3$OD) δ ppm 1.47-1.73 (m, 1H), 1.53 (d, J=2.8 Hz, 9H), 1.77-2.32 (m, 5H), 2.42-3.14 (m, 3H), 6.95 (dd, J=7.1, 4.0 Hz, 1H), 8.46 (dd, J=4.0, 1.6 Hz, 1H), 8.69 (dd, J=6.9, 1.4 Hz, 1H); MS (DCI/NH$_3$) m/z 381/383/385 (M+H)$^+$.

Example 170

N-(3-tert-butylpyrazolo[1,5-a]pyrimidin-2-yl)-4,4-dimethylpentanamide

The product from Example 105B and 4,4-dimethylpentanoic acid were processed using the method analogous to that described in Example 137 to afford the title compound. $^1$H NMR (300 MHz, DMSO-$d_6$) δ ppm 0.89 (s, 9H), 1.44 (s, 9H), 1.48-1.53 (m, 2H), 2.23-2.27 (m, 2H), 6.99 (dd, J=7.1, 4.0 Hz, 1H), 8.48 (dd, J=4.0, 2.0 Hz, 1H), 8.92 (dd, J=6.9, 1.8 Hz, 1H), 9.69 (s, 1H); MS (DCI) m/z 303 (M+H)$^+$.

Example 171

N-(3-tert-butylpyrazolo[1,5-a]pyrimidin-2-yl)-2-[(1S,2S,5S)-6,6-dimethylbicyclo[3.1.1]hept-2-yl]acetamide The product from Example 105B and the product from Example 4B were processed using the method analogous to that described in Example 137 to afford the title compound. $^1$H NMR (300 MHz, DMSO-$d_6$) δ ppm 9.65-9.70 (bs, 1H), 8.92 (dd, J=6.3, 1.8 Hz, 1H), 8.48 (dd, J=4.1, 1.8 Hz, 1H), 6.99 (dd, J=6.7, 3.9 Hz, 1H), 2.52-2.59 (m, 1H), 2.25-2.47 (m, 3H), 1.78-2.00 (m, 5H), 1.48-1.52 (m, 1H), 1.45 (s, 9H), 1.15-1.21 (bs, 3H), 1.02-1.11 (bs, 3H), 0.91 (d, J=9.3 Hz, 1H); MS (DCI) m/z 355 (M+H)$^+$.

Example 172

(±)-N-(3-tert-butylpyrazolo[1,5-a]pyrimidin-2-yl)-2-(2,3-dihydro-1H-inden-1-yl)acetamide Example 172A (±)-ethyl 2-(2,3-dihydro-1H-inden-1-yl)acetate To a mixture of products from Example 131A (0.47 g, 2.3 mmol) in EtOH (20 mL) was added Pd/C (49.5 mg, 0.046 mmol). The reaction mixture was stirred under H$_2$ atmosphere using a balloon until the starting material completely consumed. The mixture was filtered and concentrated under reduced pressure to obtain 0.47 g of the title compound. MS (DCI/NH$_3$) m/z 222 (M+NH$_4$)$^+$.

Example 172B (±)-2-(2,3-dihydro-1H-inden-1-yl)acetic acid

Example 172 A and NaOH were reacted as described in Example 131B to provide the title compound. MS (DCI/NH$_3$) m/z 194 (M+NH$_4$)$^+$.

Example 172C (±)-N-(3-tert-butylpyrazolo[1,5-a]pyrimidin-2-yl)-2-(2,3-dihydro-1H-inden-1-yl)acetamide The product from Example 105B and the product from Example 172B were processed using the method analogous to that described in Example 137 to afford the title compound. $^1$H NMR (300 MHz, DMSO-$d_6$) δ ppm 9.76-9.84 (bs, 1H), 8.95 (dd, J=7.0, 1.8 Hz, 1H), 8.49 (dd, J=4.0, 1.8 Hz, 1H), 7.26-7.35 (m, 1H), 7.19-7.26 (m, 1H), 7.11-7.19 (m, 2H), 7.00 (dd, J=7.0, 4.0 Hz, 1H), 3.50-3.62 (m, 1H), 2.75-2.93 (m, 3H), 2.17-2.42 (m, 2H), 1.66-1.81 (m, 1H), 1.47 (s, 9H); MS (DCI) m/z 349 (M+H)$^+$.

Example 173

2-(cyclopentylsulfinyl)-N-[3-(4-fluoro-3-methylphenyl)-6-methylpyrazolo[1,5-a]pyrimidin-2-yl]acetamide Solid m-chloroperoxybenzoic acid (30 mg, about 50% titre, 0.10 mmol) was added to an ice-cooled solution of the product from Example 143D (37 mg, 0.093 mmol) in CHCl$_3$ (7 mL). The yellow solution was stirred with ice cooling for 15 minutes, then transferred to a test tube and washed with 20% Na$_2$CO$_3$ (4 mL). The organic phase was concentrated under vacuum, and the residue purified by HPLC (30×100 mm XBridge column eluted with aqueous 0.1 M $(NH_4)_2CO_3$-MeOH, 80:20-0:100 over 15 min), then by flash chromatography (silica gel eluted with EtOAc-MeOH, 100:0-80:20) to provide the title compound. $^1$H NMR (300 MHz, CDCl$_3$) δ ppm 1.38-1.54 (m, 1H), 1.64-1.86 (m, 4H), 1.90-2.23 (m, 3H), 2.30 (d, J=1.6 Hz, 3H), 2.38 (s, 3H), 3.34-3.49 (m, 2H), 3.88 (d, J=14.3 Hz, 1H), 7.22-7.31 (m, 1H), 7.34-7.48 (m, 2H), 8.39 (s, 1H), 8.42-8.55 (m, 1H), 9.51 (s, 1H); MS (ESI) m/z 415 (M+H)$^+$.

Example 174

2-(cyclopentylsulfonyl)-N-[3-(4-fluoro-3-methylphenyl)-6-methylpyrazolo[1,5-a]pyrimidin-2-yl]acetamide Solid m-chloroperoxybenzoic acid (80 mg, about 50% titre, 0.28 mmol) was added to an ice-cooled solution of the product from Example 143D (37 mg, 0.093 mmol) in CHCl$_3$ (7 mL). The yellow solution was stirred with ice cooling for 40 minutes, then washed with 20% Na$_2$CO$_3$ (15 mL). The organic phase was concentrated under vacuum, and the residue was purified by flash chromatography (silica gel, eluted with EtOAc) to provide the title compound. $^1$H NMR (300 MHz, CDCl$_3$) δ ppm 1.61-1.74 (m, 2H), 1.74-1.91 (m, 2H), 2.04-2.16 (m, 4H), 2.31 (d, J=1.7 Hz, 3H), 2.39 (s, 3H), 3.48-3.68 (m, 1H), 4.06 (s, 2H), 7.28 (t, J=7.8 Hz, 1H), 7.33-7.43 (m, 2H), 8.40 (s, 1H), 8.43-8.50 (m, 1H), 8.82 (s, 1H); MS (ESI) m/z 431 (M+H)$^+$.

Example 175

2-[(cis)-bicyclo[3.1.0]hex-2-yl]-N-(3-tert-butylpyrazolo[1,5-a]pyrimidin-2-yl)acetamide A solution of 2-(bicyclo[3.1.0]hexan-2-yl)acetic acid (67 mg, 0.478 mmol, prepared as an exo/endo mixture as described in *Can. J. Chem.* 1981 57, 164-174) in DMF (1 mL) and pyridine (1 mL) was added to the product from Example 105B (42.2 mg, 0.222 mmol) in a 4 mL vial with a stir bar. 1-(3-Dimethylaminopropyl)-3-ethylcarbodiimide hydrochloride (81 mg, 0.421 mmol) was added to the resulting solution and stirring was continued for 13 hours. Methanol (1 mL) was added, and the solution was stirred for 30 minutes, then concentrated under vacuum. The residue was diluted with water (15 mL) and extracted with CH$_2$Cl$_2$ (3×10 mL). The combined extract was concentrated under vacuum, and the residue was purified by HPLC (30×100 mm XBridge column eluted with aqueous 0.1M (NH$_4$)$_2$CO$_3$-MeOH, 80:20-0:100 over 15 min) to provide the title compound. $^1$H NMR (300 MHz, CD$_3$OD) δ ppm 0.13-0.45 (m, 2H), 0.83-1.49 (m, 4H), 1.52 (s, 9H), 1.61-1.98 (m, 2H), 2.18-2.73 (m, 3H), 6.94 (dd, J=7.0, 4.0 Hz, 1H), 8.45 (dd, J=4.0, 1.5 Hz, 1H), 8.68 (dd, J=7.0, 1.5 Hz, 1H); MS (DCI/NH$_3$) m/z 313 (M+H)$^+$.

Example 176

(±)-N-[3-(4-fluoro-3-methylphenyl)-6-methylpyrazolo[1,5-a]pyrimidin-2-yl]-2-phenylpropanamide The title compound was prepared using the methods analogous to that described in Examples 1A-1D, substituting 4-bromo-1-fluoro-2-methylbenzene for 1-iodo-4-(trifluoromethoxy)benzene, 3-(dimethylamino)-2-methylacrylaldehyde for 3-(dimethylamino)acrylaldehyde, and (±)-2-phenylpropionyl chloride for 3,3-dimethylbutanoyl chloride. $^1$H NMR (300 MHz, DMSO-d$_6$) δ ppm 1.40 (d, J=6.8 Hz, 3H), 2.12 (d, J=1.4 Hz, 3H), 2.34 (d, J=0.7 Hz, 3H), 3.92 (q, J=7.1 Hz, 1H), 6.94 (d, J=9.3 Hz, 1H), 7.28-7.51 (m, 7H), 8.51 (d, J=2.0 Hz, 1H), 8.90 (s, 1H), 10.31 (s, 1H); MS (DCI) m/z 389 (M+H)$^+$

Example 177 tert-butyl {3-[(E)-2-cyclohexylvinyl]pyrazolo[1,5-a]pyrimidin-2-yl}carbamate

The product from Example 148A and 2-cyclohexylethenylboronic acid were processed using the method analogous to that described in Example 110C to provide the title compound. $^1$H NMR (300 MHz, DMSO-d$_6$) δ ppm 9.38 (s, 1H), 8.96 (dd, J=6.9, 1.7 Hz, 1H), 8.53 (dd, J=4.1, 1.7 Hz, 1H), 7.00 (dd, J=6.9, 4.0 Hz, 1H), 6.58 (dd, J=16.1, 6.8 Hz, 1H), 6.30 (dd, J=16.1, 1.2 Hz, 1H), 2.04-2.14 (m, 1H), 1.58-1.84 (m, 5H), 1.46 (s, 9H), 1.07-1.41 (m, 5H); MS (ESI) m/z 341 (M–H)$^-$.

Example 178

N-(3-tert-butyl-6-methylpyrazolo[1,5-a]pyrimidin-2-yl)-3-cyclohexylpropanamide

Example 178A 3-tert-butyl-6-methylpyrazolo[1,5-a]pyrimidin-2-amine

A mixture from Example 105A (1.56 g, 10.1 mmol), 3-dimethylamino-2-methyl-2-propenal (1.63 g, 14.4 mmol) and acetic acid (25 μL, 0.44 mmol) in ethanol (10 mL) was heated by microwave to 150° C. for 30 minutes. The mixture was cooled to ambient temperature and concentrated. Purification by silica gel chromatography (EtOAc, R$^f$=0.53) afforded 1.66 g (80%) of the title compound. MS (DCI) m/z 205 (M+H)$^+$.

Example 178B

N-(3-tert-butyl-6-methylpyrazolo[1,5-a]pyrimidin-2-yl)-3-cyclohexylpropanamide

The product from Example 178A and 3-cyclohexylpropionyl chloride were processed using the method analogous to that described in Example 105C to afford the title compound. $^1$H NMR (300 MHz, DMSO-d$_6$) δ ppm 0.81-0.93 (m, 2H), 1.09-1.28 (m, 4H), 1.43-1.51 (m, 11H), 1.58-1.73 (m, 5H), 2.24-2.33 (m, 5H), 8.38 (d, J=2.0 Hz, 1H), 8.74 (s, 1H), 9.60 (br s, 1H); MS (DCI) m/z 343 (M+H)$^+$.

Example 179

N-(3-tert-butyl-6-methylpyrazolo[1,5-a]pyrimidin-2-yl)-3-cyclopentylpropanamide

The product from Example 178A and 3-cyclopentylpropionyl chloride were processed using the method analogous to that described in Example 105C to afford the title compound. $^1$H NMR (300 MHz, DMSO-d$_6$) δ ppm 1.04-1.15 (m, 2H), 1.43-1.81 (m, 18H), 2.26-2.30 (m, 5H), 8.38 (d, J=2.0 Hz, 1H), 8.75 (s, 1H), 9.62 (br s, 1H); MS (DCI) m/z 329 (M+H)$^+$.

Example 180

N-(3-tert-butyl-6-methylpyrazolo[1,5-a]pyrimidin-2-yl)-2-cyclohexylacetamide

The product from Example 178A and cyclohexylacetyl chloride were processed using the method analogous to that described in Example 105C to afford the title compound. $^1$H NMR (300 MHz, DMSO-d$_6$) δ ppm 0.91-1.03 (m, 2H), 1.11-1.30 (m, 3H), 1.43 (s, 9H), 1.59-1.80 (m, 6H), 2.16-2.18 (m, 2H), 2.29 (d, J=1.0 Hz, 1H), 8.38 (d, J=2.0 Hz, 1H), 8.75 (s, 1H), 9.58 (br s, 1H); MS (DCI) m/z 329 (M+H)$^+$.

Example 181

2-(4-fluorophenyl)-N-[3-(2-methoxypyrimidin-5-yl)pyrazolo[1,5-a]pyrimidin-2-yl]acetamide The product from Example 140A and 2-methoxypyrimidine-5-boronic acid were processed using the method analogous to that described in Example 110C to provide the title compound. $^1$H NMR (400 MHz, DMSO-d$_6$) δ ppm 10.69-10.71 (m, 1H), 9.12 (dd, J=6.9, 1.7 Hz, 1H), 8.74 (s, 2H), 8.62 (dd, J=4.1, 1.7 Hz, 1H), 7.30-7.35 (m, 2H), 7.12-7.17 (m, 3H), 3.94 (s, 3H), 3.69 (s, 2H); MS (ESI) m/z 379 (M+H)$^+$.

Example 182

N-(3-tert-butylpyrazolo[1,5-a]pyrimidin-2-yl)-2-[4-(trifluoromethyl)phenyl]acetamide The product from Example 105B and 2-(4-(trifluoromethyl)phenyl)acetic acid were processed using the method analogous to that described in Example 137 to afford the title compound. $^1$H NMR (400 MHz, DMSO-d$_6$/Deuterium Oxide) δ ppm 8.87 (dd, J=6.9, 1.0 Hz, 1H), 8.49 (dd, J=4.0, 1.8 Hz, 1H), 7.67-7.75 (m, 2H), 7.51-7.64 (m, 2H), 7.01 (dd, J=7.0, 4.0 Hz, 1H), 3.75-3.80 (bs, 2H), 1.39 (s, 9H); MS (ESI) m/z 377 (M+H)$^+$.

Example 183

N-(3-tert-butylpyrazolo[1,5-a]pyrimidin-2-yl)-2-(3,4-dichlorophenyl)acetamide

The product from Example 105B and 2-(3,4-dichlorophenyl)acetic acid were processed using the method analogous to that described in Example 137 to afford the title compound. $^1$H NMR (400 MHz, DMSO-d$_6$/Deuterium Oxide) δ ppm 8.87 (d, J=5.9 Hz, 1H), 8.49 (dd, J=4.0, 1.8 Hz, 1H), 7.59-7.62 (m, 2H), 7.32-7.36 (m, 1H), 7.01 (dd, J=7.0, 4.0 Hz, 1H), 3.67-3.70 (bs, 2H), 1.39 (s, 9H); MS (ESI) m/z 377, 379 (M+H)$^+$.

Example 184

N-(3-tert-butylpyrazolo[1,5-a]pyrimidin-2-yl)-2-(2,6-dichlorophenyl)acetamide

The product from Example 105B and 2-(2,6-dichlorophenyl)acetic acid were processed using the method analogous to that described in Example 137 to afford the title compound. $^1$H NMR (400 MHz, DMSO-d$_6$/Deuterium Oxide) δ ppm 8.89 (d, J=6.4 Hz, 1H), 8.49 (d, J=2.0 Hz, 1H), 7.46-7.52 (m, 2H), 7.35 (dd, J=7.9 Hz, 1H), 7.01 (dd, J=6.6, 3.9 Hz, 1H), 4.05-4.09 (bs, 2H), 1.48 (s, 9H); MS (ESI) m/z 377, 379 (M+H)$^+$.

Example 185

N-[3-(6-chloropyridin-3-yl)pyrazolo[1,5-a]pyrimidin-2-yl]-2-(4-fluorophenyl)acetamide The product from Example 140A and 2-chloropyridine-5-boronic acid were processed using the method analogous to that described in Example 110C to provide the title compound. $^1$H NMR (400 MHz, DMSO-d$_6$) δ ppm 10.48-10.92 (bs, 1H), 9.13 (dd, J=7.0, 1.7 Hz, 1H), 8.72 (d, J=1.9 Hz, 1H), 8.65 (dd, J=4.2, 1.7 Hz, 1H), 8.05 (dd, J=8.5, 2.2 Hz, 1H), 7.43 (d, J=8.3 Hz, 1H), 7.32-7.36 (m, 2H), 7.13-7.19 (m, 3H), 3.69 (s, 2H); MS (APCI) m/z 382 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

The invention claimed is:

1. A compound of formula (I)

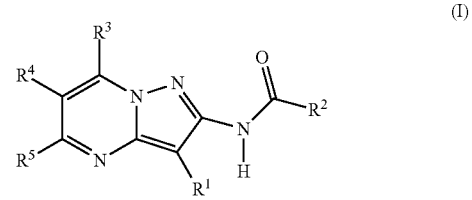

or a pharmaceutically acceptable salt, solvate, or salt of a solvate thereof, wherein R$^1$ is alkyl, alkenyl, alkynyl, haloalkyl, or G$^{1a}$; wherein each of the alkyl, alkenyl, haloalkyl, and alkynyl radicals is independently unsubstituted or substituted with 1, 2, or 3 substituents independently selected from the group consisting of OR$^{1a}$, NR$^{1b}$R$^{1c}$, N(R$^{1b}$)S(O)$_2$R$^{1d}$, SR$^{1a}$, SO$_2$R$^{1d}$, S(O)$_2$NR$^{1b}$R$^{1c}$, C(O)NR$^{1b}$R$^{1c}$, C(O)OR$^{1a}$, and G$^{1b}$;

R$^{1a}$, R$^{1b}$, and R$^{1c}$, at each occurrence, are each independently hydrogen, alkyl, haloalkyl, alkenyl, alkynyl, G$^{1b}$, or —(C$_1$-C$_6$ alkylenyl)-G$^{1b}$;

R$^{1d}$, at each occurrence, are each independently alkyl, haloalkyl, alkenyl, alkynyl, G$^{1b}$, or —(C$_1$-C$_6$ alkylenyl)-G$^{1b}$;

G$^{1a}$ and G$^{1b}$, at each occurrence, are each independently cycloalkyl, cycloalkenyl, heterocycle, heteroaryl, or aryl;

R$^2$ is —C(R$^{2x}$)=C(R$^{2y}$)(R$^{2z}$), alkyl, haloalkyl, alkenyl, alkynyl, OR$^{2a}$, NR$^{2a}$R$^{2b}$, or G$^{2a}$, wherein the alkyl, haloalkyl, alkenyl, and alkynyl are each independently unsubstituted or substituted with 1, 2, or 3 substituents independently selected from the group consisting of OR$^{2a}$, NR$^{2b}$R$^{2c}$, SR$^{2a}$, S(O)R$^{2d}$, SO$_2$R$^{2d}$, and G$^{2b}$;

R$^{2x}$ is hydrogen, alkyl, or haloalkyl;

R$^{2y}$ and R$^{2z}$, together with the carbon atom to which they are attached, form a cycloalkyl or heterocycle ring;

R$^{2a}$, R$^{2b}$, and R$^{2c}$, at each occurrence, are each independently hydrogen, alkyl, haloalkyl, alkenyl, alkynyl, G$^{2b}$, or —(C$_1$-C$_6$ alkylenyl)-G$^{2b}$;

R$^{2d}$, at each occurrence, is independently alkyl, haloalkyl, alkenyl, alkynyl, G$^{2b}$, or —(C$_1$-C$_6$ alkylenyl)-G$^{2b}$;

G$^{2a}$ is cycloalkyl, cycloalkenyl, heterocycle, heteroaryl, or bicyclic aryl;

G$^{2b}$, at each occurrence, is each independently cycloalkyl, cycloalkenyl, heterocycle, heteroaryl, or aryl;

G$^{1a}$, G$^{1b}$, G$^{2a}$, and G$^{2b}$, and the ring formed by R$^{2y}$, R$^{2z}$, and the carbon atom to which they are attached, are each independently unsubstituted or substituted with 1, 2, 3, 4, or 5 substituents independently selected from the group consisting of halogen, alkyl, alkenyl, alkynyl, haloalkyl, oxo, NO$_2$, CN, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(C$_1$-C$_6$ alkylenyl)-OR$^f$, —(C$_1$-C$_6$ alkylenyl)-OC(O)R$^f$, —(C$_1$-C$_6$ alkylenyl)-OC(O)N(R$^f$)$_2$, —(C$_1$-C$_6$ alkylenyl)-S(O)$_2$R$^e$, —(C$_1$-C$_6$ alkylenyl)-S(O)$_2$N(R$^f$)$_2$, —(C$_1$-C$_6$ alkylenyl)-C(O)R$^f$, —(C$_1$-C$_6$ alkylenyl)-C(O)OR$^f$, —(C$_1$-C$_6$ alkylenyl)-C(O)N(R$^f$)$_2$, —(C$_1$-C$_6$ alkylenyl)-N(R$^f$)$_2$, —(C$_1$-C$_6$ alkylenyl)-N(R$^f$)C(O)R$^f$, —(C$_1$-C$_6$ alkylenyl)-N(R$^f$)S(O)$_2$R$^e$, —(C$_1$-C$_6$ alkylenyl)-N(R$^f$)C(O)O(R$^e$), —(C$_1$-C$_6$ alkylenyl)-N(R$^f$)C(O)N(R$^f$)$_2$, and —(C$_1$-C$_6$ alkylenyl)-CN;

R$^f$, at each occurrence, is independently hydrogen, C$_1$-C$_4$ alkyl, C$_1$-C$_4$ haloalkyl, —(C$_1$-C$_6$ alkylenyl)-OR$^g$, G$^{1c}$, or —(C$_1$-C$_6$ alkylenyl)-G$^{1c}$;

R$^e$, at each occurrence, is independently C$_1$-C$_4$ alkyl, C$_1$-C$_4$ haloalkyl, —(C$_1$-C$_6$ alkylenyl)-OR$^g$, G$^{1c}$, or —(C$_1$-C$_6$ alkylenyl)-G$^{1c}$;

R$^g$, at each occurrence, is independently hydrogen, C$_1$-C$_4$ alkyl, C$_1$-C$_4$ haloalkyl, monocyclic cycloalkyl, or —(C$_1$-C$_6$ alkylenyl)-(monocyclic cycloalkyl); wherein the monocyclic cycloakyl, alone or as part of the group, is optionally substituted with 1, 2, 3, 4, or 5 substituents independently selected from the group consisting of alkyl, haloalkyl, oxo, OH, and alkoxy;

G$^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy; and R$^3$, R$^4$, and R$^5$ are each independently hydrogen, halogen, alkyl, or haloalkyl.

2. The compound according to claim 1 or a pharmaceutically acceptable salt, solvate, or salt of a solvate thereof, wherein R$^3$, R$^4$, and R$^5$ are each independently hydrogen or alkyl.

3. The compound according to claim 1 or a pharmaceutically acceptable salt, solvate, or salt of a solvate thereof, wherein R$^1$ is alkyl, alkenyl, alkynyl, haloalkyl, or G$^{1a}$; wherein each of the alkyl, alkenyl, and alkynyl radicals is independently unsubstituted or substituted with one substituent selected from the group consisting of N(R$^{1b}$)S(O)$_2$R$^{1d}$, C(O)NR$^{1b}$R$^{1c}$, C(O)OR$^{1a}$, and G$^{1b}$.

4. The compound according to claim 1 or a pharmaceutically acceptable salt, solvate, or salt of a solvate thereof, wherein R$^1$ is haloalkyl, optionally substituted alkyl, optionally substituted alkenyl, or optionally substituted alkynyl.

5. The compound according to claim 1 or a pharmaceutically acceptable salt, solvate, or salt of a solvate thereof, wherein R$^1$ is haloalkyl, optionally substituted alkyl, optionally substituted alkenyl, or optionally substituted alkynyl, and R$^2$ is haloalkyl or optionally substituted alkyl.

6. The compound according to claim 1 or a pharmaceutically acceptable salt, solvate, or salt of a solvate thereof, wherein R$^1$ is haloalkyl, optionally substituted alkyl, optionally substituted alkenyl, or optionally substituted alkynyl, and R$^2$ is alkyl or alkenyl, each substituted with a G$^{2b}$ group.

7. The compound according to claim 6 or a pharmaceutically acceptable salt, solvate, or salt of a solvate thereof, wherein G$^{2b}$ is cycloalkyl, heteroaryl, or aryl, each of which is optionally substituted.

8. The compound according to claim 6 or a pharmaceutically acceptable salt, solvate, or salt of a solvate thereof, wherein G$^{2b}$ is optionally substituted aryl.

9. The compound according to claim 8, or a pharmaceutically acceptable salt, solvate, or salt of a solvate thereof, wherein R$^1$ is haloalkyl or unsubstituted alkyl.

10. The compound according to claim 8, or a pharmaceutically acceptable salt, solvate, or salt of a solvate thereof, wherein R$^1$ is alkyl, alkenyl, or alkynyl, each of which is independently substituted with a G$^{1b}$ group.

11. The compound according to claim 10 or a pharmaceutically acceptable salt, solvate, or salt of a solvate thereof, wherein G$^{1b}$ is cycloalkyl, heteroaryl, or aryl, each of which is optionally substituted.

12. The compound according to claim 10 or a pharmaceutically acceptable salt, solvate, or salt of a solvate thereof, wherein G$^{1b}$ is optionally substituted phenyl.

13. The compound according to claim 12 or a pharmaceutically acceptable salt, solvate, or salt of a solvate thereof, wherein R$^3$, R$^4$, and R$^5$ are each independently hydrogen or alkyl.

14. The compound according to claim 1 or a pharmaceutically acceptable salt, solvate, or salt of a solvate thereof, wherein R$^1$ is G$^{1a}$.

15. The compound according to claim 1 or a pharmaceutically acceptable salt, solvate, or salt of a solvate thereof, wherein R$^1$ is G$^{1a}$, and R$^2$ is haloalkyl or optionally substituted alkyl.

16. The compound according to claim 1 or a pharmaceutically acceptable salt, solvate, or salt of a solvate thereof, wherein R$^1$ is G$^{1a}$, and R$^2$ is alkyl or alkenyl, each substituted with a G$^{2b}$ group.

17. The compound according to claim 16 or a pharmaceutically acceptable salt, solvate, or salt of a solvate thereof, wherein G$^{2b}$ is cycloalkyl, heteroaryl, or aryl, each of which is optionally substituted.

18. The compound according to claim 16 or a pharmaceutically acceptable salt, solvate, or salt of a solvate thereof, wherein G$^{2b}$ is optionally substituted aryl.

19. The compound according to claim 18 or a pharmaceutically acceptable salt, solvate, or salt of a solvate thereof, wherein G$^{1a}$ is heterocycle, cycloalkyl, aryl, or heteroaryl, each of which is optionally substituted.

20. The compound according to claim 18 or a pharmaceutically acceptable salt, solvate, or salt of a solvate thereof, wherein G$^{1a}$ is optionally substituted monocyclic cycloalkyl.

21. The compound according to claim 20 or a pharmaceutically acceptable salt, solvate, or salt of a solvate thereof, wherein R$^3$, R$^4$, and R$^5$ are each independently hydrogen or alkyl.

22. The compound according to claim 18 or a pharmaceutically acceptable salt, solvate, or salt of a solvate thereof, wherein G$^{1a}$ is optionally substituted aryl.

23. The compound according to claim 22 or a pharmaceutically acceptable salt, solvate, or salt of a solvate thereof, wherein R$^3$, R$^4$, and R$^5$ are each independently hydrogen or alkyl.

24. The compound according to claim 14, or a pharmaceutically acceptable salt thereof, wherein:

G$^{1a}$ is phenyl that is unsubstituted or substituted with 1, 2, 3, 4, or 5 substituents independently selected from the group consisting of alkyl, halogen, haloalkyl, —C(O)OR$^f$, —C(O)N(R$^f$)$_2$, —(C$_1$-C$_6$ alkylenyl)-C(O)OR$^f$, and —OR$^f$; and R$^f$, at each occurrence, is independently hydrogen, C$_1$-C$_4$ alkyl, or C$_1$-C$_4$.

25. The compound according to claim 24, or a pharmaceutically acceptable salt thereof, wherein R$^3$, R$^4$, and R$^5$ are each independently hydrogen or C$_1$-C$_6$ alkyl.

26. The compound according to claim 24, or a pharmaceutically acceptable salt thereof, wherein $R^2$ is unsubstituted alkyl.

27. The compound according to claim 24, or a pharmaceutically acceptable salt thereof, wherein $R^2$ is alkyl substituted with a substituent selected from the group consisting of $OR^{2a}$, $SR^{2a}$, $S(O)R^{2d}$, and $S(O)R^{2d}$.

28. The compound according to claim 24, or a pharmaceutically acceptable salt thereof, wherein $R^2$ is alkyl or alkenyl, each of which is substituted with a $G^{2b}$ group.

29. The compound according to claim 24, or a pharmaceutically acceptable salt thereof, wherein:

$R^2$ is alkyl or alkenyl, each of which is substituted with a $G^{2b}$ group;

$G^{2b}$ is phenyl that unsubstituted or substituted with 1, 2, 3, 4, or 5 substituents independently selected from the group consisting of halogen, alkyl, alkenyl, alkynyl, haloalkyl, oxo, $NO_2$, CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —($C_1$-$C_6$ alkylenyl)-$OR^f$, —($C_1$-$C_6$ alkylenyl)-$OC(O)R^f$, —($C_1$-$C_6$ alkylenyl)-$OC(O)N(R^f)_2$, —($C_1$-$C_6$ alkylenyl)-$S(O)_2R^e$, —($C_1$-$C_6$ alkylenyl)-$S(O)_2N(R^f)_2$, —($C_1$-$C_6$ alkylenyl)-$C(O)R^f$, —($C_1$-$C_6$ alkylenyl)-$C(O)OR^f$, —($C_1$-$C_6$ alkylenyl)-$C(O)N(R^f)_2$, —($C_1$-$C_6$ alkylenyl)-$N(R^f)_2$, —($C_1$-$C_6$ alkylenyl)-$N(R^f)C(O)R^f$, —($C_1$-$C_6$ alkylenyl)-$N(R^f)S(O)_2R^e$, —($C_1$-$C_6$ alkylenyl)-$N(R^f)C(O)O(R^e)$, —($C_1$-$C_6$ alkylenyl)-$N(R^f)C(O)N(R^f)_2$, and —($C_1$-$C_6$ alkylenyl)-CN;

$R^f$, at each occurrence, is independently hydrogen, $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^e$, at each occurrence, is independently $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^g$, at each occurrence, is independently hydrogen, $C_1$-$C_4$ alkyl, $C_1$-$C_4$ haloalkyl, monocyclic cycloalkyl, or —($C_1$-$C_6$ alkylenyl)-(monocyclic cycloalkyl); wherein the monocyclic cycloakyl, alone or as part of the group, is optionally substituted with 1, 2, 3, 4, or 5 substituents independently selected from the group consisting of alkyl, haloalkyl, oxo, OH, and alkoxy; and $G^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy.

30. The compound according to claim 24, or a pharmaceutically acceptable salt thereof, wherein:

$R^2$ is alkyl or alkenyl, each of which is substituted with a $G^{2b}$ group;

$G^{2b}$ is cycloalkyl that unsubstituted or substituted with 1, 2, 3, 4, or 5 substituents independently selected from the group consisting of halogen, alkyl, alkenyl, alkynyl, haloalkyl, oxo, $NO_2$, CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —($C_1$-$C_6$ alkylenyl)-$OR^f$, —($C_1$-$C_6$ alkylenyl)-$OC(O)R^f$, —($C_1$-$C_6$ alkylenyl)-$OC(O)N(R^f)_2$, —($C_1$-$C_6$ alkylenyl)-$S(O)_2R^e$, —($C_1$-$C_6$ alkylenyl)-$S(O)_2N(R^f)_2$, —($C_1$-$C_6$ alkylenyl)-$C(O)R^f$, —($C_1$-$C_6$ alkylenyl)-$C(O)OR^f$, —($C_1$-$C_6$ alkylenyl)-$C(O)N(R^f)_2$, —($C_1$-$C_6$ alkylenyl)-$N(R^f)_2$, —($C_1$-$C_6$ alkylenyl)-$N(R^f)C(O)R^f$, —($C_1$-$C_6$ alkylenyl)-$N(R^f)S(O)_2R^e$, —($C_1$-$C_6$ alkylenyl)-$N(R^f)C(O)O(R^e)$, —($C_1$-$C_6$ alkylenyl)-$N(R^f)C(O)N(R^f)_2$, and —($C_1$-$C_6$ alkylenyl)-CN;

$R^f$, at each occurrence, is independently hydrogen, $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^e$, at each occurrence, is independently $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^g$, at each occurrence, is independently hydrogen, $C_1$-$C_4$ alkyl, $C_1$-$C_4$ haloalkyl, monocyclic cycloalkyl, or —($C_1$-$C_6$ alkylenyl)-(monocyclic cycloalkyl); wherein the monocyclic cycloakyl, alone or as part of the group, is optionally substituted with 1, 2, 3, 4, or 5 substituents independently selected from the group consisting of alkyl, haloalkyl, oxo, OH, and alkoxy; and $G^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy.

31. The compound according to claim 24 or a pharmaceutically acceptable salt thereof, wherein:

$R^2$ is alkyl or alkenyl, each of which is substituted with a $G^{2b}$ group;

$G^{2b}$ is heteroaryl that unsubstituted or substituted with 1, 2, 3, 4, or 5 substituents independently selected from the group consisting of halogen, alkyl, alkenyl, alkynyl, haloalkyl, oxo, $NO_2$, CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —($C_1$-$C_6$ alkylenyl)-$OR^f$, —($C_1$-$C_6$ alkylenyl)-$OC(O)R^f$, —($C_1$-$C_6$ alkylenyl)-$OC(O)N(R^f)_2$, —($C_1$-$C_6$ alkylenyl)-$S(O)_2R^e$, —($C_1$-$C_6$ alkylenyl)-$S(O)_2N(O_2$, —($C_1$-$C_6$ alkylenyl)-$C(O)R^f$, —($C_1$-$C_6$ alkylenyl)-$C(O)OR^f$, —($C_1$-$C_6$ alkylenyl)-$C(O)N(R^f)_2$, —($C_1$-$C_6$ alkylenyl)-$N(R^f)_2$, —($C_1$-$C_6$ alkylenyl)-$N(R^f)C(O)R^f$, —($C_1$-$C_6$ alkylenyl)-$N(R^f)S(O)_2R^e$, —($C_1$-$C_6$ alkylenyl)-$N(R^f)C(O)O(R^e)$, —($C_1$-$C_6$ alkylenyl)-$N(R^f)C(O)N(R^f)_2$, and —($C_1$-$C_6$ alkylenyl)-CN;

$R^f$, at each occurrence, is independently hydrogen, $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^e$, at each occurrence, is independently $C_1$-$C_4$ alkyl, $C_1$-$C_4$ haloalkyl, —($C_1$-$C_6$ alkylenyl)-$OR^g$, $G^{1c}$, or —($C_1$-$C_6$ alkylenyl)-$G^{1c}$;

$R^g$, at each occurrence, is independently hydrogen, $C_1$-$C_4$ alkyl, $C_1$-$C_4$ haloalkyl, monocyclic cycloalkyl, or —($C_1$-$C_6$ alkylenyl)-(monocyclic cycloalkyl); wherein the monocyclic cycloakyl, alone or as part of the group, is optionally substituted with 1, 2, 3, 4, or 5 substituents independently selected from the group consisting of alkyl, haloalkyl, oxo, OH, and alkoxy; and $G^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy.

32. The compound according to claim 4, or a pharmaceutically acceptable salt thereof, wherein $R^1$ is unsubstituted alkyl.

33. The compound according to claim 32, or a pharmaceutically acceptable salt thereof, wherein $R^3$, $R^4$, and $R^5$ are each independently hydrogen or $C_1$-$C_6$ alkyl.

34. The compound according to claim 32, or a pharmaceutically acceptable salt thereof, wherein $R^2$ is unsubstituted alkyl.

35. The compound according to claim 32, or a pharmaceutically acceptable salt thereof, wherein $R^2$ is alkyl or alkenyl, each of which is substituted with a $G^{2b}$ group.

36. The compound according to claim 32, or a pharmaceutically acceptable salt thereof, wherein:
  $R^2$ is alkyl or alkenyl, each of which is substituted with a $G^{2b}$ group;
  $G^{2b}$ is phenyl that unsubstituted or substituted with 1, 2, 3, 4, or 5 substituents independently selected from the group consisting of halogen, alkyl, alkenyl, alkynyl, haloalkyl, oxo, $NO_2$, CN, $-OR^f$, $-OC(O)R^f$, $-OC(O)N(R^f)_2$, $-S(O)_2R^e$, $-S(O)_2N(R^f)_2$, $-C(O)R^f$, $-C(O)OR^f$, $-C(O)N(R^f)_2$, $-N(R^f)_2$, $-N(R^f)C(O)R^f$, $-N(R^f)S(O)_2R^e$, $-N(R^f)C(O)O(R^e)$, $-N(R^f)C(O)N(R^f)_2$, $-(C_1-C_6\text{ alkylenyl})-OR^f$, $-(C_1-C_6\text{ alkylenyl})-OC(O)R^f$, $-(C_1-C_6\text{ alkylenyl})-OC(O)N(R^f)_2$, $-(C_1-C_6\text{ alkylenyl})-S(O)_2R^e$, $-(C_1-C_6\text{ alkylenyl})-S(O)_2N(R^f_-)_2$, $-(C_1-C_6\text{ alkylenyl})-C(O)R^f$, $-(C_1-C_6\text{ alkylenyl})-C(O)OR^f$, $-(C_1-C_6\text{ alkylenyl})-C(O)N(R^f)_2$, $-(C_1-C_6\text{ alkylenyl})-N(R^f)_2$, $-(C_1-C_6\text{ alkylenyl})-N(R^f)C(O)R^f$, $-(C_1-C_6\text{ alkylenyl})-N(R^f)S(O)_2R^e$, $-(C_1-C_6\text{ alkylenyl})-N(R^f)C(O)O(R^e)$, $-(C_1-C_6\text{ alkylenyl})-N(R^f)C(O)N(R^f)_2$, and $-(C_1-C_6\text{ alkylenyl})-CN$;
  $R^f$, at each occurrence, is independently hydrogen, $C_1-C_4$ alkyl, $C_1-C_4$ haloalkyl, $-(C_1-C_6\text{ alkylenyl})-OR^g$, $G^{1c}$, or $-(C_1-C_6\text{ alkylenyl})-G^{1c}$;
  $R^e$, at each occurrence, is independently $C_1-C_4$ alkyl, $C_1-C_4$ haloalkyl, $-(C_1-C_6\text{ alkylenyl})-OR^g$, $G^{1c}$, or $-(C_1-C_6\text{ alkylenyl})-G^{1c}$;
  $R^g$, at each occurrence, is independently hydrogen, $C_1-C_4$ alkyl, $C_1-C_4$ haloalkyl, monocyclic cycloalkyl, or $-(C_1-C_6\text{ alkylenyl})-(\text{monocyclic cycloalkyl})$; wherein the monocyclic cycloakyl, alone or as part of the group, is optionally substituted with 1, 2, 3, 4, or 5 substituents independently selected from the group consisting of alkyl, haloalkyl, oxo, OH, and alkoxy; and
  $G^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy.

37. The compound according to claim 32, or a pharmaceutically acceptable salt thereof, wherein:
  $R^2$ is alkyl or alkenyl, each of which is substituted with a $G^{2b}$ group;
  $G^{2b}$ is cycloalkyl that unsubstituted or substituted with 1, 2, 3, 4, or 5 substituents independently selected from the group consisting of halogen, alkyl, alkenyl, alkynyl, haloalkyl, oxo, $NO_2$, CN, $-OR^f$, $-OC(O)R^f$, $-OC(O)N(R^f)_2$, $-S(O)_2R^e$, $-S(O)_2N(R^f)_2$, $-C(O)R^f$, $-C(O)OR^f$, $-C(O)N(R^f)_2$, $-N(R^f)_2$, $-N(R^f)C(O)R^f$, $-N(R^f)S(O)_2R^e$, $-N(R^f)C(O)O(R^e)$, $-N(R^f)C(O)N(R^f)_2$, $-(C_1-C_6\text{ alkylenyl})-OR^f$, $-(C_1-C_6\text{ alkylenyl})-OC(O)R^f$, $-(C_1-C_6\text{ alkylenyl})-OC(O)N(R^f)_2$, $-(C_1-C_6\text{ alkylenyl})-S(O)_2R^e$, $-(C_1-C_6\text{ alkylenyl})-S(O)_2N(R^f)_2$, $-(C_1-C_6\text{ alkylenyl})-C(O)R^f$, $-(C_1-C_6\text{ alkylenyl})-C(O)OR^f$, $-(C_1-C_6\text{ alkylenyl})-C(O)N(R^f)_2$, $-(C_1-C_6\text{ alkylenyl})-N(R^f)_2$, $-(C_1-C_6\text{ alkylenyl})-N(R^f)C(O)R^f$, $-(C_1-C_6\text{ alkylenyl})-N(R^f)S(O)_2R^e$, $-(C_1-C_6\text{ alkylenyl})-N(R^f)C(O)O(R^e)$, $-(C_1-C_6\text{ alkylenyl})-N(R^f)C(O)N(R^f)_2$, and $-(C_1-C_6\text{ alkylenyl})-CN$;
  $R^f$, at each occurrence, is independently hydrogen, $C_1-C_4$ alkyl, $C_1-C_4$ haloalkyl, $-(C_1-C_6\text{ alkylenyl})-OR^g$, $G^{1c}$, or $-(C_1-C_6\text{ alkylenyl})-G^{1c}$;
  $R^e$, at each occurrence, is independently $C_1-C_4$ alkyl, $C_1-C_4$ haloalkyl, $-(C_1-C_6\text{ alkylenyl})-OR^g$, $G^{1c}$, or $-(C_1-C_6\text{ alkylenyl})-G^{1c}$;
  $R^g$, at each occurrence, is independently hydrogen, $C_1-C_4$ alkyl, $C_1-C_4$ haloalkyl, monocyclic cycloalkyl, or $-(C_1-C_6\text{ alkylenyl})-(\text{monocyclic cycloalkyl})$; wherein the monocyclic cycloakyl, alone or as part of the group, is optionally substituted with 1, 2, 3, 4, or 5 substituents independently selected from the group consisting of alkyl, haloalkyl, oxo, OH, and alkoxy; and
  $G^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy.

38. The compound according to claim 32 or a pharmaceutically acceptable salt thereof, wherein:
  $R^2$ is alkyl or alkenyl, each of which is substituted with a $G^{2b}$ group;
  $G^{2b}$ is heteroaryl that unsubstituted or substituted with 1, 2, 3, 4, or 5 substituents independently selected from the group consisting of halogen, alkyl, alkenyl, alkynyl, haloalkyl, oxo, $NO_2$, CN, $-OR^f$, $-OC(O)R^f$, $-OC(O)N(R^f)_2$, $-S(O)_2R^e$, $-S(O)_2N(R^f)_2$, $-C(O)R^f$, $-C(O)OR^f$, $-C(O)N(R^f)_2$, $-N(R^f)_2$, $-N(R^f)C(O)R^f$, $-N(R^f)S(O)_2R^e$, $-N(R^f)C(O)O(R^e)$, $-N(R^f)C(O)N(R^f)_2$, $-(C_1-C_6\text{ alkylenyl})-OR^f$, $-(C_1-C_6\text{ alkylenyl})-OC(O)R^f$, $-(C_1-C_6\text{ alkylenyl})-OC(O)N(R^f)_2$, $-(C_1-C_6\text{ alkylenyl})-S(O)_2R^e$, $-(C_1-C_6\text{ alkylenyl})-S(O)_2N(R^f)_2$, $-(C_1-C_6\text{ alkylenyl})-C(O)R^f$, $-(C_1-C_6\text{ alkylenyl})-C(O)OR^f$, $-(C_1-C_6\text{ alkylenyl})-C(O)N(R^f)_2$, $-(C_1-C_6\text{ alkylenyl})-N(R^f)_2$, $-(C_1-C_6\text{ alkylenyl})-N(R^f)C(O)R^f$, $-(C_1-C_6\text{ alkylenyl})-N(R^f)S(O)_2R^e$, $-(C_1-C_6\text{ alkylenyl})-N(R^f)C(O)O(R^e)$, $-(C_1-C_6\text{ alkylenyl})-N(R^f)C(O)N(R^f)_2$, and $-(C_1-C_6\text{ alkylenyl})-CN$;
  $R^f$, at each occurrence, is independently hydrogen, $C_1-C_4$ alkyl, $C_1-C_4$ haloalkyl, $-(C_1-C_6\text{ alkylenyl})-OR^g$, $G^{1c}$, or $-(C_1-C_6\text{ alkylenyl})-G^{1c}$;
  $R^e$, at each occurrence, is independently $C_1-C_4$ alkyl, $C_1-C_4$ haloalkyl, $-(C_1-C_6\text{ alkylenyl})-OR^g$, $G^{1c}$, or $-(C_1-C_6\text{ alkylenyl})-G^{1c}$;
  $R^g$, at each occurrence, is independently hydrogen, $C_1-C_4$ alkyl, $C_1-C_4$ haloalkyl, monocyclic cycloalkyl, or $-(C_1-C_6\text{ alkylenyl})-(\text{monocyclic cycloalkyl})$; wherein the monocyclic cycloakyl, alone or as part of the group, is optionally substituted with 1, 2, 3, 4, or 5 substituents independently selected from the group consisting of alkyl, haloalkyl, oxo, OH, and alkoxy; and
  $G^{1c}$, at each occurrence, is independently cycloalkyl, cycloalkenyl, heterocycle, heteroaryl, or aryl, each of which is independently unsubstituted or substituted with 1, 2, 3, 4, or 5 substituents independently selected from the group consisting of halogen, alkyl, alkenyl, alkynyl, haloalkyl, oxo, OH, alkoxy, and haloalkoxy.

39. The compound according to claim 1 or a pharmaceutically acceptable salt, solvate, or salt of a solvate thereof, wherein the compound is selected from the group consisting of:
  3,3-dimethyl-N-{3-[4-(trifluoromethoxy)phenyl]pyrazolo[1,5-a]pyrimidin-2-yl}butanamide;
  N-[3-(4-fluorophenyl)pyrazolo[1,5-a]pyrimidin-2-yl]-3,3-dimethylbutanamide;

3,3-dimethyl-N-{6-methyl-3-[3-(trifluoromethoxy)phenyl]pyrazolo[1,5-a]pyrimidin-2-yl}butanamide;
2-[(1S,2S,5S)-6,6-dimethylbicyclo[3.1.1]hept-2-yl]-N-{3-[4-(trifluoromethoxy)phenyl]pyrazolo[1,5-a]pyrimidin-2-yl}acetamide;
2-cyclopentyl-N-[3-(4-fluorobenzyl)-6-methylpyrazolo[1,5-a]pyrimidin-2-yl]acetamide;
N-[3-(4-chlorophenyl)pyrazolo[1,5-a]pyrimidin-2-yl]-2-phenylacetamide;
N-[3-(4-chlorophenyl)pyrazolo[1,5-a]pyrimidin-2-yl]-3-cyclopentylpropanamide;
2-(3-methoxyphenyl)-N-{6-methyl-3-[4-(trifluoromethoxy)phenyl]pyrazolo[1,5-a]pyrimidin-2-yl}acetamide;
2-(4-fluorophenyl)-N-{7-methyl-3-[4-(trifluoromethoxy)phenyl]pyrazolo[1,5-a]pyrimidin-2-yl}acetamide;
N-[3-(2,2-dimethylpropyl)pyrazolo[1,5-a]pyrimidin-2-yl]-3-phenylpropanamide;
3-cyclohexyl-N-[3-(2,2-dimethylpropyl)pyrazolo[1,5-a]pyrimidin-2-yl]propanamide;
N-[3-(3-fluoro-4-methylphenyl)-7-methylpyrazolo[1,5-a]pyrimidin-2-yl]-3,3-dimethylbutanamide;
N-[3-(3-fluoro-4-methylphenyl)-7-methylpyrazolo[1,5-a]pyrimidin-2-yl]-2-(4-methoxyphenyl)acetamide;
3-cyclohexyl-N-[3-(2,2-dimethylpropyl)-5,7-dimethylpyrazolo[1,5-a]pyrimidin-2-yl]propanamide;
N-[3-(2,2-dimethylpropyl)-5,7-dimethylpyrazolo[1,5-a]pyrimidin-2-yl]-3-phenylpropanamide;
N-[3-(2,2-dimethylpropyl)-5,7-dimethylpyrazolo[1,5-a]pyrimidin-2-yl]-2-(4-methoxyphenyl)acetamide;
3-cyclohexyl-N-[3-(2,2-dimethylpropyl)-6-methylpyrazolo[1,5-a]pyrimidin-2-yl]propanamide;
N-[3-(2,2-dimethylpropyl)-6-methylpyrazolo[1,5-a]pyrimidin-2-yl]-2-(4-methoxyphenyl)acetamide;
N-[3-(3-fluoro-4-methylphenyl)pyrazolo[1,5-a]pyrimidin-2-yl]-2-phenylacetamide;
3-cyclopentyl-N-[3-(3-fluoro-4-methylphenyl)-6-methylpyrazolo[1,5-a]pyrimidin-2-yl]propanamide;
2-(3,4-dimethoxyphenyl)-N-[3-(3-fluoro-4-methylphenyl)-5,7-dimethylpyrazolo[1,5-a]pyrimidin-2-yl]acetamide;
3,3-dimethyl-N-{3-[3-(trifluoromethoxy)phenyl]pyrazolo[1,5-a]pyrimidin-2-yl}butanamide;
3-cyclopentyl-N-[3-(4-fluorophenyl)pyrazolo[1,5-a]pyrimidin-2-yl]propanamide;
3-cyclohexyl-N-[3-(4-fluorophenyl)pyrazolo[1,5-a]pyrimidin-2-yl]propanamide;
N-[3-(4-fluorophenyl)-6-methylpyrazolo[1,5-a]pyrimidin-2-yl]-2-phenylacetamide;
N-[3-(4-fluorophenyl)-6-methylpyrazolo[1,5-a]pyrimidin-2-yl]-2-(3-methoxyphenyl)acetamide;
2-(4-chlorophenyl)-N-[3-(4-fluorophenyl)-6-methylpyrazolo[1,5-a]pyrimidin-2-yl]acetamide;
2-(4-fluorophenyl)-N-[3-(4-fluorophenyl)-7-methylpyrazolo[1,5-a]pyrimidin-2-yl]acetamide;
N-[3-(4-fluorophenyl)-5,7-dimethylpyrazolo[1,5-a]pyrimidin-2-yl]-3-phenylpropanamide;
N-[3-(4-fluoro-3-methylphenyl)pyrazolo[1,5-a]pyrimidin-2-yl]-3-phenylpropanamide;
N-[3-(4-fluoro-3-methylphenyl)pyrazolo[1,5-a]pyrimidin-2-yl]-2-(4-fluorophenyl)acetamide;
N-[3-(4-fluoro-3-methylphenyl)-5,7-dimethylpyrazolo[1,5-a]pyrimidin-2-yl]-2-(3-methoxyphenyl)acetamide;
N-[3-(4-fluoro-3-methylphenyl)-5,7-dimethylpyrazolo[1,5-a]pyrimidin-2-yl]-3,3-dimethylbutanamide;
2-cyclohexyl-N-[3-(4-fluoro-3-methylphenyl)-5,7-dimethylpyrazolo[1,5-a]pyrimidin-2-yl]acetamide;
3-cyclohexyl-N-[3-(4-fluoro-3-methylphenyl)-6-methylpyrazolo[1,5-a]pyrimidin-2-yl]propanamide;
N-[3-(2,2-dimethylpropyl)-7-methylpyrazolo[1,5-a]pyrimidin-2-yl]-2-(4-methoxyphenyl)acetamide;
3-cyclohexyl-N-[3-(2,2-dimethylpropyl)-7-methylpyrazolo[1,5-a]pyrimidin-2-yl]propanamide;
N-[3-(2,2-dimethylpropyl)-7-methylpyrazolo[1,5-a]pyrimidin-2-yl]-2-(3-methoxyphenyl)acetamide;
N-[3-(4-chlorophenyl)-6-methylpyrazolo[1,5-a]pyrimidin-2-yl]-2-(3,4-dimethoxyphenyl)acetamide;
N-[3-(4-chlorophenyl)-7-methylpyrazolo[1,5-a]pyrimidin-2-yl]-3,3-dimethylbutanamide;
N-[3-(4-chlorophenyl)-7-methylpyrazolo[1,5-a]pyrimidin-2-yl]-2-(3-methoxyphenyl)acetamide;
N-[3-(4-chlorophenyl)-5,7-dimethylpyrazolo[1,5-a]pyrimidin-2-yl]-2-cyclohexylacetamide;
N-[3-(4-chlorophenyl)-5,7-dimethylpyrazolo[1,5-a]pyrimidin-2-yl]-3-cyclopentylpropanamide;
N-[3-(4-chloro-3-methylphenyl)-6-methylpyrazolo[1,5-a]pyrimidin-2-yl]-3-phenylpropanamide;
N-[3-(4-chloro-3-methylphenyl)pyrazolo[1,5-a]pyrimidin-2-yl]-2-(4-fluorophenyl)acetamide;
N-[3-(4-chloro-3-methylphenyl)-7-methylpyrazolo[1,5-a]pyrimidin-2-yl]-3-cyclopentylpropanamide;
N-[3-(4-chloro-3-methylphenyl)-5,7-dimethylpyrazolo[1,5-a]pyrimidin-2-yl]-3-phenylpropanamide;
N-[3-(4-chloro-3-methylphenyl)-5,7-dimethylpyrazolo[1,5-a]pyrimidin-2-yl]-3-cyclohexylpropanamide;
N-[3-(3-chlorophenyl)-7-methylpyrazolo[1,5-a]pyrimidin-2-yl]-3-phenylpropanamide;
N-[3-(3-chlorophenyl)-6-methylpyrazolo[1,5-a]pyrimidin-2-yl]-2-(4-methoxyphenyl)acetamide;
N-[3-(3-chlorophenyl)-6-methylpyrazolo[1,5-a]pyrimidin-2-yl]-3,3-dimethylbutanamide;
N-[3-(3-chlorophenyl)-5,7-dimethylpyrazolo[1,5-a]pyrimidin-2-yl]-2-cyclohexylacetamide;
N-[3-(3-chlorophenyl)-5,7-dimethylpyrazolo[1,5-a]pyrimidin-2-yl]-2-cyclopentylacetamide;
N-[3-(3-chlorophenyl)-5,7-dimethylpyrazolo[1,5-a]pyrimidin-2-yl]-2-(3-methoxyphenyl)acetamide;
N-[3-(3-chlorophenyl)pyrazolo[1,5-a]pyrimidin-2-yl]-2-(2,5-dimethoxyphenyl)acetamide;
N-[3-(3-chlorophenyl)pyrazolo[1,5-a]pyrimidin-2-yl]-3-cyclopentylpropanamide;
N-[3-(3-chlorophenyl)pyrazolo[1,5-a]pyrimidin-2-yl]-2-phenylacetamide;
2-(4-chlorophenyl)-N-[3-(3-chlorophenyl)pyrazolo[1,5-a]pyrimidin-2-yl]acetamide;
N-{6-methyl-3-[4-(trifluoromethyl)phenyl]pyrazolo[1,5-a]pyrimidin-2-yl}-3-phenylpropanamide;
3-cyclopentyl-N-{3-[4-(trifluoromethyl)phenyl]pyrazolo[1,5-a]pyrimidin-2-yl}propanamide;
3-cyclopentyl-N-{5,7-dimethyl-3-[4-(trifluoromethyl)phenyl]pyrazolo[1,5-a]pyrimidin-2-yl}propanamide;
2-(4-chlorophenyl)-N-{5,7-dimethyl-3-[4-(trifluoromethyl)phenyl]pyrazolo[1,5-a]pyrimidin-2-yl}acetamide;
3,3-dimethyl-N-{6-methyl-3-[3-(trifluoromethyl)phenyl]pyrazolo[1,5-a]pyrimidin-2-yl}butanamide;
2-cyclopentyl-N-{3-[3-(trifluoromethyl)phenyl]pyrazolo[1,5-a]pyrimidin-2-yl}acetamide;
3-cyclohexyl-N-{7-methyl-3-[3-(trifluoromethyl)phenyl]pyrazolo[1,5-a]pyrimidin-2-yl}propanamide;
2-(2,5-dimethoxyphenyl)-N-{7-methyl-3-[3-(trifluoromethyl)phenyl]pyrazolo[1,5-a]pyrimidin-2-yl}acetamide;

2-(4-fluorophenyl)-N-{7-methyl-3-[3-(trifluoromethyl)phenyl]pyrazolo[1,5-a]pyrimidin-2-yl}acetamide;
N-[3-(3-chloro-4-methylphenyl)-7-methylpyrazolo[1,5-a]pyrimidin-2-yl]-3-cyclohexylpropanamide;
N-[3-(3-chloro-4-methylphenyl)-7-methylpyrazolo[1,5-a]pyrimidin-2-yl]-2-(4-chlorophenyl)acetamide;
N-[3-(4-fluorobenzyl)pyrazolo[1,5-a]pyrimidin-2-yl]-2-(4-methoxyphenyl)acetamide;
3-cyclopentyl-N-[3-(4-fluorobenzyl)-7-methylpyrazolo[1,5-a]pyrimidin-2-yl]propanamide;
N-[3-(3-chloro-4-methylphenyl)-6-methylpyrazolo[1,5-a]pyrimidin-2-yl]-2-(4-fluorophenyl)acetamide;
N-[3-(3-chloro-4-methylphenyl)-6-methylpyrazolo[1,5-a]pyrimidin-2-yl]-2-(2,5-dimethoxyphenyl)acetamide;
N-[3-(3-chloro-4-methylphenyl)-6-methylpyrazolo[1,5-a]pyrimidin-2-yl]-3-phenylpropanamide;
N-[3-(3-chloro-4-methylphenyl)pyrazolo[1,5-a]pyrimidin-2-yl]-3-cyclopentylpropanamide;
N-[3-(4-fluorobenzyl)-6-methylpyrazolo[1,5-a]pyrimidin-2-yl]-2-(4-methoxyphenyl)acetamide;
3-cyclohexyl-N-[3-(4-fluorobenzyl)-6-methylpyrazolo[1,5-a]pyrimidin-2-yl]propanamide;
N-{5,7-dimethyl-3-[3-(trifluoromethyl)phenyl]pyrazolo[1,5-a]pyrimidin-2-yl}-3-phenylpropanamide;
3-cyclohexyl-N-{7-methyl-3-[4-(trifluoromethyl)phenyl]pyrazolo[1,5-a]pyrimidin-2-yl}propanamide;
2-(4-methoxyphenyl)-N-{7-methyl-3-[4-(trifluoromethyl)phenyl]pyrazolo[1,5-a]pyrimidin-2-yl}acetamide;
2-(4-chlorophenyl)-N-[3-(3-fluorophenyl)pyrazolo[1,5-a]pyrimidin-2-yl]acetamide;
2-(4-fluorophenyl)-N-[3-(3-fluorophenyl)pyrazolo[1,5-a]pyrimidin-2-yl]acetamide;
2-cyclopentyl-N-[3-(3-fluorophenyl)-6-methylpyrazolo[1,5-a]pyrimidin-2-yl]acetamide;
2-(4-fluorophenyl)-N-[3-(3-fluorophenyl)-6-methylpyrazolo[1,5-a]pyrimidin-2-yl]acetamide;
N-[3-(3-fluorophenyl)-5,7-dimethylpyrazolo[1,5-a]pyrimidin-2-yl]-3-phenylpropanamide;
2-cyclohexyl-N-[3-(3-fluorophenyl)-5,7-dimethylpyrazolo[1,5-a]pyrimidin-2-yl]acetamide;
2-cyclopentyl-N-{3-[3-fluoro-4-(trifluoromethyl)phenyl]-6-methylpyrazolo[1,5-a]pyrimidin-2-yl}acetamide;
3-cyclopentyl-N-{3-[3-fluoro-4-(trifluoromethyl)phenyl]pyrazolo[1,5-a]pyrimidin-2-yl}propanamide;
3-cyclohexyl-N-(3-phenylpyrazolo[1,5-a]pyrimidin-2-yl)propanamide;
3-phenyl-N-(3-phenylpyrazolo[1,5-a]pyrimidin-2-yl)propanamide;
N-(7-methyl-3-phenylpyrazolo[1,5-a]pyrimidin-2-yl)-2-phenylacetamide;
3,3-dimethyl-N-(6-methyl-3-phenylpyrazolo[1,5-a]pyrimidin-2-yl)butanamide;
2-(4-chlorophenyl)-N-(6-methyl-3-phenylpyrazolo[1,5-a]pyrimidin-2-yl)acetamide;
2-cyclohexyl-N-(5,7-dimethyl-3-phenylpyrazolo[1,5-a]pyrimidin-2-yl)acetamide;
3-cyclopentyl-N-(5,7-dimethyl-3-phenylpyrazolo[1,5-a]pyrimidin-2-yl)propanamide;
N-(5,7-dimethyl-3-phenylpyrazolo[1,5-a]pyrimidin-2-yl)-2-(4-fluorophenyl)acetamide;
N-[3-(3-fluorophenyl)-7-methylpyrazolo[1,5-a]pyrimidin-2-yl]-2-(4-methoxyphenyl)acetamide;
2-(pyridin-3-yl)-N-{3-[4-(trifluoromethoxy)phenyl]pyrazolo[1,5-a]pyrimidin-2-yl}acetamide;
1-[3-(4-chlorophenyl)pyrazolo[1,5-a]pyrimidin-2-yl]-3-(cyclohexylmethyl)urea;
N-[3-(4-chlorophenyl)pyrazolo[1,5-a]pyrimidin-2-yl]-2-(pyridin-2-yl)acetamide;
N-[3-(4-chlorophenyl)pyrazolo[1,5-a]pyrimidin-2-yl]-2-(pyridin-3-yl)acetamide;
N-[3-(4-chlorophenyl)pyrazolo[1,5-a]pyrimidin-2-yl]-2-(pyridin-4-yl)acetamide;
1-[3-(4-chlorophenyl)pyrazolo[1,5-a]pyrimidin-2-yl]-3-(tetrahydro-2H-pyran-4-ylmethyl)urea;
N-[3-(4-chlorophenyl)pyrazolo[1,5-a]pyrimidin-2-yl]-2-(2-hydroxyphenyl)acetamide;
N-(3-tert-butylpyrazolo[1,5-a]pyrimidin-2-yl)-3-cyclopentylpropanamide;
N-(3-tert-butylpyrazolo[1,5-a]pyrimidin-2-yl)-3,3-dimethylbutanamide;
2-(adamantan-1-yl)-N-(3-tert-butylpyrazolo[1,5-a]pyrimidin-2-yl)acetamide;
1-[3-(4-chlorophenyl)pyrazolo[1,5-a]pyrimidin-2-yl]-3-cyclohexylurea;
N-[3-(4-chlorophenyl)pyrazolo[1,5-a]pyrimidin-2-yl]-2-(3,5-dimethoxyphenyl)acetamide;
3,3-dimethyl-N-[3-(pyridin-3-yl)pyrazolo[1,5-a]pyrimidin-2-yl]butanamide;
N-{3-[(E)-2-(4-chlorophenyl)vinyl]pyrazolo[1,5-a]pyrimidin-2-yl}-3,3-dimethylbutanamide;
3-cyclopentyl-N-(3-isopropylpyrazolo[1,5-a]pyrimidin-2-yl)propanamide;
N-(3-isopropylpyrazolo[1,5-a]pyrimidin-2-yl)-3,3-dimethylbutanamide;
N-[3-(4-chloro-3-methylphenyl)-5,7-dimethylpyrazolo[1,5-a]pyrimidin-2-yl]-3-cyclopropylpropanamide;
3,3-dimethyl-N-{3-[(E)-2-(6-methylpyridin-3-yl)vinyl]pyrazolo[1,5-a]pyrimidin-2-yl}butanamide;
2-(adamantan-1-yl)-N-[3-(2-naphthyl)pyrazolo[1,5-a]pyrimidin-2-yl]acetamide;
N-[3-(4-chlorophenyl)pyrazolo[1,5-a]pyrimidin-2-yl]-3-methyl-3-phenylbutanamide;
3-cyclopropyl-N-(3-isopropylpyrazolo[1,5-a]pyrimidin-2-yl)propanamide;
3-cyclopentyl-N-[3-(pyridin-3-yl)pyrazolo[1,5-a]pyrimidin-2-yl]propanamide;
3-cyclopentyl-N-{3-[4-(trifluoromethoxy)phenyl]pyrazolo[1,5-a]pyrimidin-2-yl}propanamide;
(±)-exo-2-bicyclo[2.2.1]hept-2-yl-N-(3-tert-butylpyrazolo[1,5-a]pyrimidin-2-yl)acetamide;
3-cyclopentyl-N-(3-isopropyl-5,7-dimethylpyrazolo[1,5-a]pyrimidin-2-yl)propanamide;
N-(3-tert-butylpyrazolo[1,5-a]pyrimidin-2-yl)-2-(4-fluorophenyl)acetamide;
(±)-exo-2-bicyclo[2.2.1]hept-2-yl-N-{3-[4-(trifluoromethoxy)phenyl]pyrazolo[1,5-a]pyrimidin-2-yl}acetamide;
N-(3-tert-butylpyrazolo[1,5-a]pyrimidin-2-yl)-3-methyl-3-phenylbutanamide;
N-(3-tert-butylpyrazolo[1,5-a]pyrimidin-2-yl)-2-(3,5-difluorophenyl)acetamide;
N-[3-(3-fluorophenyl)pyrazolo[1,5-a]pyrimidin-2-yl]-3-methyl-3-phenylbutanamide;
N-(3-tert-butylpyrazolo[1,5-a]pyrimidin-2-yl)-3-phenylpropanamide;
N-(3-tert-butylpyrazolo[1,5-a]pyrimidin-2-yl)-2-cyclohexylacetamide;
(±)-N-(3-tert-butylpyrazolo[1,5-a]pyrimidin-2-yl)-2-(1-methyl-2,3-dihydro-1H-inden-1-yl)acetamide;
N-(3-tert-butylpyrazolo[1,5-a]pyrimidin-2-yl)-3-cyclohexylpropanamide;

2-(cyclopentyloxy)-N-(3-isopropylpyrazolo[1,5-a]pyrimidin-2-yl)acetamide;
N-[3-(4-chloro-3-methylphenyl)-5,7-dimethylpyrazolo[1,5-a]pyrimidin-2-yl]-2-(cyclopentyloxy)acetamide;
3-cyclopentyl-N-[3-(3-fluorophenyl)pyrazolo[1,5-a]pyrimidin-2-yl]propanamide;
(2E)-N-(3-tert-butylpyrazolo[1,5-a]pyrimidin-2-yl)-3-phenylacrylamide;
N-(3-tert-butylpyrazolo[1,5-a]pyrimidin-2-yl)-2-phenylacetamide;
2-(3,5-dimethoxyphenyl)-N-[3-(3-fluorophenyl)pyrazolo[1,5-a]pyrimidin-2-yl]acetamide;
3-cyclopentyl-N-[3-(4-fluoro-3-methylphenyl)-6-methylpyrazolo[1,5-a]pyrimidin-2-yl]propanamide;
2-(4-fluorophenyl)-N-{3-[4-(trifluoromethoxy)phenyl]pyrazolo[1,5-a]pyrimidin-2-yl}acetamide;
3,3-dimethyl-N-[3-(2-methylphenyl)pyrazolo[1,5-a]pyrimidin-2-yl]butanamide;
2-(adamantan-1-yl)-N-{3-[4-(trifluoromethoxy)phenyl]pyrazolo[1,5-a]pyrimidin-2-yl}acetamide;
2-(cyclopentylthio)-N-[3-(4-fluoro-3-methylphenyl)-6-methylpyrazolo[1,5-a]pyrimidin-2-yl]acetamide;
N-{3-[(1E)-3,3-dimethylbut-1-en-1-yl]pyrazolo[1,5-a]pyrimidin-2-yl}-3,3-dimethylbutanamide;
3-cyclopentyl-N-[3-(1-ethylcyclohexyl)pyrazolo[1,5-a]pyrimidin-2-yl]propanamide;
(±)-exo-2-bicyclo[2.2.1]hept-2-yl-N-[3-(1-ethylcyclohexyl)pyrazolo[1,5-a]pyrimidin-2-yl]acetamide;
3,3-dimethyl-N-(3-{(E)-2-[4-(trifluoromethyl)phenyl]vinyl}pyrazolo[1,5-a]pyrimidin-2-yl)butanamide;
tert-butyl {3-[4-(trifluoromethoxy)phenyl]pyrazolo[1,5-a]pyrimidin-2-yl}carbamate;
N-[3-(4-fluoro-3-methylphenyl)-6-methylpyrazolo[1,5-a]pyrimidin-2-yl]-3-methyl-3-phenylbutanamide;
(±)-exo-2-bicyclo[2.2.1]hept-2-yl-N-[3-(4-fluoro-3-methylphenyl)-6-methylpyrazolo[1,5-a]pyrimidin-2-yl]acetamide;
2-(adamantan-1-yl)-N-[3-(4-fluoro-3-methylphenyl)-6-methylpyrazolo[1,5-a]pyrimidin-2-yl]acetamide;
N-(3-tert-butylpyrazolo[1,5-a]pyrimidin-2-yl)-2-(4-chlorophenyl)acetamide;
3-cyclopentyl-N-(3-{(E)-2-[4-(trifluoromethyl)phenyl]vinyl}pyrazolo[1,5-a]pyrimidin-2-yl)propanamide;
N-(3-tert-butylpyrazolo[1,5-a]pyrimidin-2-yl)-2-cyclopentylacetamide;
N-(3-tert-butylpyrazolo[1,5-a]pyrimidin-2-yl)-2-(4-methoxyphenyl)acetamide;
3,3-dimethyl-N-(3-{[4-(trifluoromethoxy)phenyl]ethynyl}pyrazolo[1,5-a]pyrimidin-2-yl)butanamide;
N-[3-(4-chlorophenyl)pyrazolo[1,5-a]pyrimidin-2-yl]-3-cyclohexylpropanamide;
(±)-exo-2-bicyclo[2.2.1]hept-2-yl-N-[3-(4-chlorophenyl)pyrazolo[1,5-a]pyrimidin-2-yl]acetamide;
3-methyl-N-{7-methyl-3-[4-(trifluoromethoxy)phenyl]pyrazolo[1,5-a]pyrimidin-2-yl}-3-phenylbutanamide;
(±)-exo-2-bicyclo[2.2.1]hept-2-yl-N-{7-methyl-3-[4-(trifluoromethoxy)phenyl]pyrazolo[1,5-a]pyrimidin-2-yl}acetamide;
N-{3-[(1E)-3,3-dimethylbut-1-en-1-yl]pyrazolo[1,5-a]pyrimidin-2-yl}-2-(4-fluorophenyl)acetamide;
2-(adamantan-1-yl)-N-[3-(4-chlorophenyl)pyrazolo[1,5-a]pyrimidin-2-yl]acetamide;
N-(3-tert-butylpyrazolo[1,5-a]pyrimidin-2-yl)-2-cyclohexylideneacetamide;
N-[3-(4-fluoro-3-methylphenyl)-6-methylpyrazolo[1,5-a]pyrimidin-2-yl]-4,4-dimethylpentanamide;
N-(3-tert-butylpyrazolo[1,5-a]pyrimidin-2-yl)-3-[4-(trifluoromethyl)phenyl]propanamide;
N-(3-tert-butylpyrazolo[1,5-a]pyrimidin-2-yl)-2-(4-isopropylphenyl)acetamide;
3,3-dimethyl-N-{3-[(1E)-prop-1-en-1-yl]pyrazolo[1,5-a]pyrimidin-2-yl}butanamide;
2-(4-fluorophenyl)-N-{5-methyl-3-[4-(trifluoromethoxy)phenyl]pyrazolo[1,5-a]pyrimidin-2-yl}acetamide;
N-(3-tert-butylpyrazolo[1,5-a]pyrimidin-2-yl)-2-[(cis)-6,6-dichlorobicyclo[3.1.0]hex-2-yl]acetamide;
N-(3-tert-butylpyrazolo[1,5-a]pyrimidin-2-yl)-4,4-dimethylpentanamide;
N-(3-tert-butylpyrazolo[1,5-a]pyrimidin-2-yl)-2-[(1S,2S,5S)-6,6-dimethylbicyclo[3.1.1]hept-2-yl]acetamide;
(±)—N-(3-tert-butylpyrazolo[1,5-a]pyrimidin-2-yl)-2-(2,3-dihydro-1H-inden-1-yl)acetamide;
2-(cyclopentylsulfinyl)-N-[3-(4-fluoro-3-methylphenyl)-6-methylpyrazolo[1,5-a]pyrimidin-2-yl]acetamide;
2-(cyclopentylsulfonyl)-N-[3-(4-fluoro-3-methylphenyl)-6-methylpyrazolo[1,5-a]pyrimidin-2-yl]acetamide;
2-[(cis)-bicyclo[3.1.0]hex-2-yl]-N-(3-tert-butylpyrazolo[1,5-a]pyrimidin-2-yl)acetamide;
(±)—N-[3-(4-fluoro-3-methylphenyl)-6-methylpyrazolo[1,5-a]pyrimidin-2-yl]-2-phenylpropanamide;
tert-butyl {3-[(E)-2-cyclohexylvinyl]pyrazolo[1,5-a]pyrimidin-2-yl}carbamate;
N-(3-tert-butyl-6-methylpyrazolo[1,5-a]pyrimidin-2-yl)-3-cyclohexylpropanamide;
N-(3-tert-butyl-6-methylpyrazolo[1,5-a]pyrimidin-2-yl)-3-cyclopentylpropanamide;
N-(3-tert-butyl-6-methylpyrazolo[1,5-a]pyrimidin-2-yl)-2-cyclohexylacetamide;
2-(4-fluorophenyl)-N-[3-(2-methoxypyrimidin-5-yl)pyrazolo[1,5-a]pyrimidin-2-yl]acetamide;
N-(3-tert-butylpyrazolo[1,5-a]pyrimidin-2-yl)-2-[4-(trifluoromethyl)phenyl]acetamide;
N-(3-tert-butylpyrazolo[1,5-a]pyrimidin-2-yl)-2-(3,4-dichlorophenyl)acetamide;
N-(3-tert-butylpyrazolo[1,5-a]pyrimidin-2-yl)-2-(2,6-dichlorophenyl)acetamide; and
N-[3-(6-chloropyridin-3-yl)pyrazolo[1,5-a]pyrimidin-2-yl]-2-(4-fluorophenyl)acetamide.

40. A pharmaceutical composition comprising a therapeutically effective amount of a compound of formula (I) according to claim 1 or a pharmaceutically acceptable salt, solvate, or salt of a solvate thereof, in combination with one or more pharmaceutically acceptable carriers.

\* \* \* \* \*